US010758532B2

(12) United States Patent
Kollins et al.

(10) Patent No.: US 10,758,532 B2
(45) Date of Patent: Sep. 1, 2020

(54) COMPOSITIONS, DEVICES, AND METHODS FOR TREATING OR PREVENTING HEADACHES

(71) Applicant: SATSUMA PHARMACEUTICALS, INC., South San Francisco, CA (US)

(72) Inventors: John Kollins, San Francisco, CA (US); Fumiyoshi Iwashima, San Francisco, CA (US); Detlef Albrecht, Saratoga, CA (US); Robert David Schultz, Raleigh, NC (US)

(73) Assignee: Satsuma Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 16/710,538

(22) Filed: Dec. 11, 2019

(65) Prior Publication Data
US 2020/0179378 A1 Jun. 11, 2020

Related U.S. Application Data

(60) Provisional application No. 62/847,607, filed on May 14, 2019, provisional application No. 62/799,635, filed on Jan. 31, 2019, provisional application No. 62/778,158, filed on Dec. 11, 2018.

(51) Int. Cl.
A61K 47/38 (2006.01)
A61K 47/26 (2006.01)
A61K 9/14 (2006.01)
A61M 15/08 (2006.01)
A61P 25/04 (2006.01)
A61K 31/4985 (2006.01)
A61K 9/00 (2006.01)

(52) U.S. Cl.
CPC ........ A61K 31/4985 (2013.01); A61K 9/0019 (2013.01); A61K 9/0043 (2013.01); A61K 9/14 (2013.01); A61K 47/26 (2013.01); A61K 47/38 (2013.01); A61M 15/08 (2013.01); A61P 25/04 (2018.01)

(58) Field of Classification Search
CPC .............. A61K 31/4985; A61K 9/0019; A61K 9/0043; A61K 9/14; A61K 47/26; A61K 47/38; A61P 25/04
USPC ...................................................... 514/250
See application file for complete search history.

(56) References Cited

U.S. PATENT DOCUMENTS

| | | | |
|---|---|---|---|
| 4,613,500 A | 9/1986 | Suzuki et al. | |
| 5,169,849 A | 12/1992 | Kiechel et al. | |
| 5,756,483 A | 5/1998 | Merkus | |
| 6,906,027 B2 | 6/2005 | Oki et al. | |
| 7,022,311 B1 | 4/2006 | Ohkuma et al. | |
| 7,638,138 B2 | 12/2009 | Oki et al. | |
| 8,062,670 B2 | 11/2011 | Baran, Jr. et al. | |
| 8,435,554 B2 | 5/2013 | Oki et al. | |
| 8,673,360 B2 | 3/2014 | Nagata et al. | |
| 8,710,092 B2 | 4/2014 | Zhang et al. | |
| 8,827,946 B2 | 9/2014 | Tsutsui et al. | |
| 9,101,539 B2 | 8/2015 | Nagata et al. | |
| 9,138,410 B2 | 9/2015 | Oki et al. | |
| 9,707,226 B2 | 7/2017 | Keegan et al. | |
| 2003/0044458 A1 | 3/2003 | Wright et al. | |
| 2005/0118272 A1 | 6/2005 | Besse et al. | |
| 2005/0158250 A1 | 7/2005 | Oki et al. | |
| 2006/0057213 A1 | 3/2006 | Larhrib et al. | |
| 2006/0147388 A1 | 7/2006 | Merkus et al. | |
| 2007/0253913 A1 | 11/2007 | Mohsen et al. | |
| 2008/0287451 A1 | 11/2008 | Cook et al. | |
| 2009/0163604 A1 | 6/2009 | Kakizawa et al. | |
| 2009/0217928 A1 | 9/2009 | Patton et al. | |
| 2010/0178331 A1 | 7/2010 | Nagata et al. | |
| 2011/0045088 A1 | 2/2011 | Tsutsui et al. | |
| 2011/0171141 A1 | 7/2011 | Kellerman et al. | |
| 2013/0095145 A1 | 4/2013 | Nagata et al. | |
| 2013/0129781 A1 | 5/2013 | Nagata et al. | |
| 2014/0179704 A1 | 6/2014 | Kellerman et al. | |
| 2015/0238412 A1 | 8/2015 | Kellerman et al. | |
| 2016/0228433 A1 | 8/2016 | Haruta et al. | |
| 2018/0036247 A1* | 2/2018 | Haruta | A61K 9/19 |
| 2019/0000753 A1 | 1/2019 | Narasimha et al. | |
| 2019/0091424 A1 | 3/2019 | Haruta | |
| 2019/0209463 A1 | 7/2019 | Hoekman et al. | |

FOREIGN PATENT DOCUMENTS

| | | |
|---|---|---|
| GB | 1592563 A | 7/1981 |
| JP | 2005520799 A | 7/2005 |
| JP | 2006519219 A | 8/2006 |
| JP | 2013126989 A | 6/2013 |
| WO | WO-9422445 A2 | 10/1994 |
| WO | WO-0027373 A1 | 5/2000 |
| WO | WO-2004073729 A1 | 9/2004 |
| WO | WO-2006016530 A1 | 2/2006 |
| WO | WO-2012105236 A1 | 8/2012 |

(Continued)

OTHER PUBLICATIONS

Gallagher, R. Michael, "Acute Treatment of Migraine With Dihydroergotamine Nasal Spray", Arch Neurol 1996;53:1285-1291.
Kellerman, Donald J. et al., "Assessment of the Consistency of Absorption of Dihydroergotamine Following Oral Inhalation: Pooled Results from Four Clinical Studies", Journal of Aerosol and Pulmonary Drug Delivery, 2013, vol. 26, No. 5, pp. 297-306.
Schran, Horst F. et al., "Bioequivalence and Safety of Subcutaneously and Intramuscularly Administered Dihydroergotamine in Healthy Volunteers", Current Therapeutic Research, Dec. 1994; vol. 55, No. 12, 8 pages.
Shrewsbury SB et al., "Safety, Tolerability and Comparative Bioavailability of a Novel Intranasal DHE Product (INP104)", Headache, presented at the American Headache Society 60th Annual Meeting, Jun. 28-Jul. 1, 2018, San Francisco, CA.
"Office Action dated Sep. 27, 2017 for U.S. Appl. No. 15/023,206".
"U.S. Appl. No. 15/023,206 Office Action dated Apr. 24, 2018".

(Continued)

Primary Examiner — Yevgeny Valenrod
(74) Attorney, Agent, or Firm — Wilson Sonsini Goodrich & Rosati

(57) ABSTRACT

Disclosed herein are pharmaceutical compositions, devices, their combinations, and their uses thereof for example in treating or preventing headaches.

35 Claims, 13 Drawing Sheets

(56) References Cited

FOREIGN PATENT DOCUMENTS

| WO | WO-2015044782 A2 | 4/2015 |
|---|---|---|
| WO | WO-2018025089 A2 | 2/2018 |
| WO | WO-2019065673 A1 | 4/2019 |

OTHER PUBLICATIONS

Anjilvel, et al. A multiple-path model of particle deposition in the rat lung. Fundamental and Applied Toxicology 28.1 (1995): 41-50.

Aurora SK, "OnabotulinumtoxinA for treatment of chronic migraine: pooled analyses of the 56-week PREEMPT clinical program", Headache. Oct. 2011;51(9):1358-73. doi: 10.1111/j.1526-4610.2011. 01990.x. Epub Aug. 29, 2011.

Berge, et al. Pharmaceutical salts. J Pharm Sci. Jan. 1977;66(1):1-19.

Ceolus™ basic information (Asahi Kasei's web site for pharmaceutical excipients), Obtained online on Sep. 17, 2015.

Detlef Albrecht et al., Pharmacokinetics and Safety of Intranasal Dihydroergotamine Powder (STS101), American Headache Society 61st Annual Scientific Meeting, Jul. 11-14, 2019, Philadelphia, PA.

Edwards KR et al., "Comparison of intravenous valproate versus intramuscular dihydroergotamine and metoclopramide for acute treatment of migraine headache", Headache. Nov.-Dec. 2001;41(10):976-80.

Fasiolo, Laura Tiozzo et al., "Opportunity and challenges of nasal powders:Drug formulation and delivery", European Journal of Pharmaceutical Sciences, 2017, 1-16.

Fumiyoshi Iwashima et al., "STS101 (Dry Powder Intranasal Dihydroergotamine) Drug-Device Combination Achieves Consistent and Robust Delivery Performance for Migraine Patients", presented at the International headache Conference, Sep. 5-8, 2019.

Humbert H et al., "Human pharmacokinetics of dihydroergotamine administered by nasal spray", Clin Pharmacol Ther. Sep. 1996;60(3):265-75.

International search report and written opinion dated Mar. 20, 2015 for PCT/IB2014/002706.

J. N. J. M. de Hoon et al., "Dihydroergotamine: discrepancy between arterial, arteriolar and pharmacokinetic data", J. Clin Pharmacol, 2001, 52, 45-51.

Kelsey Satterly et al., "Comparison of Early Plasma Exposure of DHE Following Delivery by Nasal, Oral Inhalation or Intravenous Administration", presented at the 2019 American Headache Society Annual Meeting Jul. 11-14, 2019, Philadelphia, PA.

Marttin, Emmeline et al. "Nasal Absorption of Dihydroergotamine from Liquid and Powder Formulations in Rabbits", Journal of Pharmaceutical Sciences, 1997, vol. 86, No. 7, 802-807.

Noveck, Robert J et al. "Assessing acute systemic effects of an inhaled drug with serial echocardiography: a placebo-controlled comparison of inhaled and intravenous dihydroergotamine." Drug design, development and therapy vol. 7 619-25. Jul. 24, 2013, doi:10.2147/DDDT.S44093.

Office action dated Jan. 30, 2017 for U.S. Appl. No. 15/023,206.

P-H. M. van der Kuy et al., "Bioavailability of intranasal formulations of dihydroergotamine", Eur J Clin Pharmacol, 1999, 55:677-680.

Price, et al. Multiple Path Particle Dosimetry model (MPPD v1.0): A model for human and rat airway particle dosimetry. RIVM Report 650010030. Published Dec. 11, 2002.

Robert O. Cook, PhD et al., "Reduced Adverse Event Profile of Orally Inhaled DHE (MAP0004) vs IV DHE: Potential Mechanism", Headache, 2009:49, 1423-1434.

S. Mellander and I. Nordenfelt, "Comparative Effects of Dihydroergotamine and Noradrenaline on Resistance Exchange and Capacitance Functions in the Peripheral Circulation", Clinical Science, 1970, 39, 183-201.

Shannon Storm, PhD et al., "Comparison of the Pharmacokinetics of STS101, an Intranasal Dry Powder Formulation of Dihydroergotamine, with Other Intranasal, Injectable, and Oral Inhaled DHE Formulations", IHC-PO-362, presented at the International Headache Conference, Sep. 5-8, 2019.

Shrewsbury SB et al., "STOP 301: Open-label Safety and Tolerability of Chronic Intermittent Usage for 24/52 Weeks of INP104 [Nasal Dihydroergotamine Mesylate (DHE) Administered by Precision Olfactory Delivery (POD) Device] in Migraine Headach)", Headache, presented at the 2019 American Headache Society Annual Meeting, Jul. 11-141, 2019, Philadelphia, PA.

Sieneke Labruijere et al., "Dihydroergotamine and sumatriptan in isolated human coronary artery, middle meningeal artery and saphenous", Cephalalgia, 2015, vol. 35(2), 182-189.

Silberstein SD et al., "Efficacy and safety of topiramate for the treatment of chronic migraine: a randomized, double-blind, placebo-controlled trial", Headache. Feb. 2007;47(2):170-80.

Stephen B. Shrewsbury, MB ChB, FFPM, Maha et al., "STOP 101: A Phase 1, Randomized, Open-Label, Comparative Bioavailability Study of INP104, Dihydroergotamine Mesylate (DHE) Administered Intranasally by a I123 Precision Olfactory Delivery (POD) Device, in Healthy Adult Subjects", Headache, 2019, 1-16.

Stephen D. Silberstein, MD et al., "Dihydroergotamine (DHE)—Then and Now: A Narrative Review", Headache, 2019, 1-18.

U.S. Appl. No. 15/023,206 Office Action dated Jan. 30, 2017.

U.S. Appl. No. 15/023206 Non-Final Office Action dated Aug. 27, 2019.

U.S. Appl. No. 16/414,350 Non-Final Office Action dated Jul. 10, 2019.

U.S. Appl. No. 16/414,350 Final Office Action dated Dec. 2, 2019.

W. H. Aellig, "Investigation of the Venoconstrictor Effect of 8' Hydroxydihydroergotamine, the Main Metabolite of Dihydroergotamine, in Man", European Journal of Clinical Pharmacology, 1984, 26:239-242.

Whyte, MD, Chad A., "Dihydroergotamine and its Use in Migraine With Posterior Fossa Symptoms", Headache, 2010:50, 1419-1423.

Wurm, M. et al., "Comparative Trial of the Peripheral Vascular Effects of Dihydroergotamine Administered via the Intranasal and Intramuscular Routes", Institut de Recherches Cardiovasculaires Royat, Sandoz Laboratories, Pharmaceutical Research Center, 426-427.

International Search Report and Written Opinion dated Apr. 8, 2020 for International Application Serial No. PCT/US2019/065647, (8 pages).

* cited by examiner

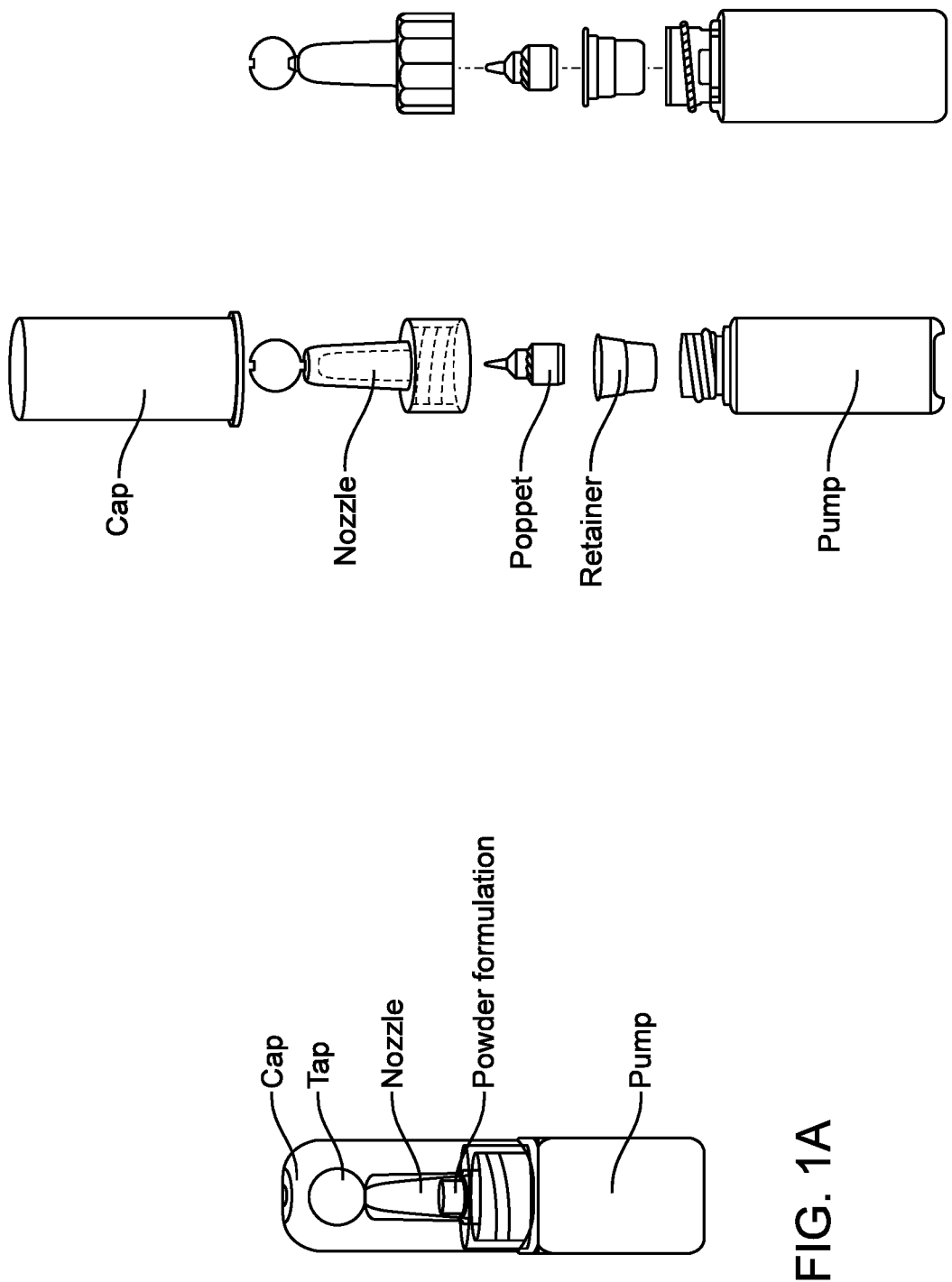

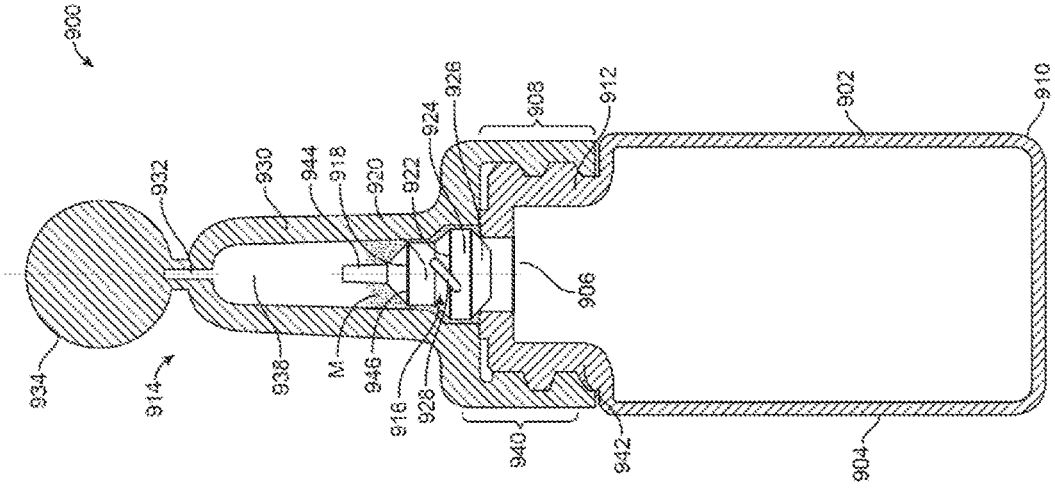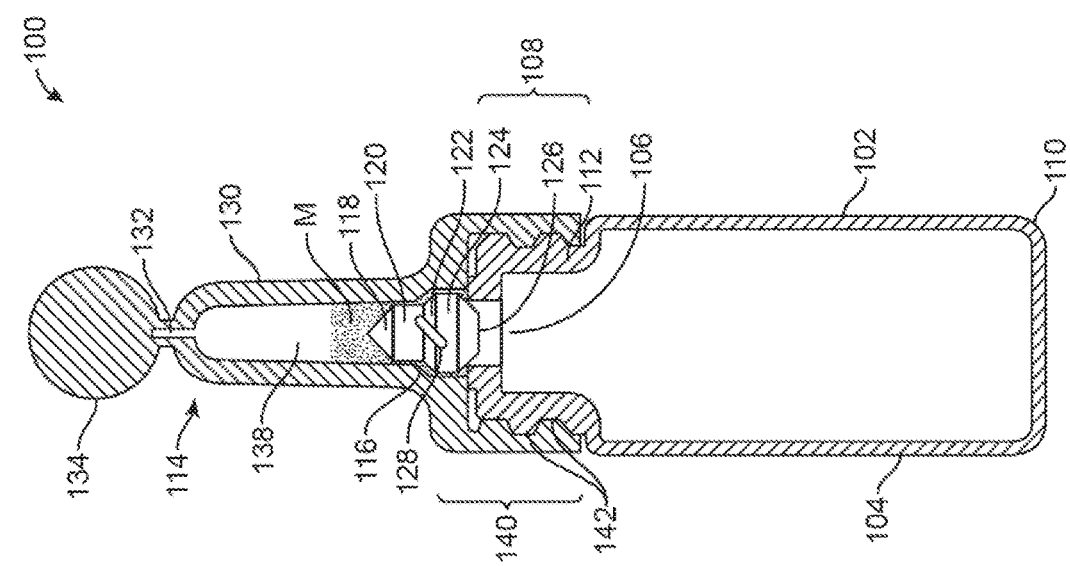

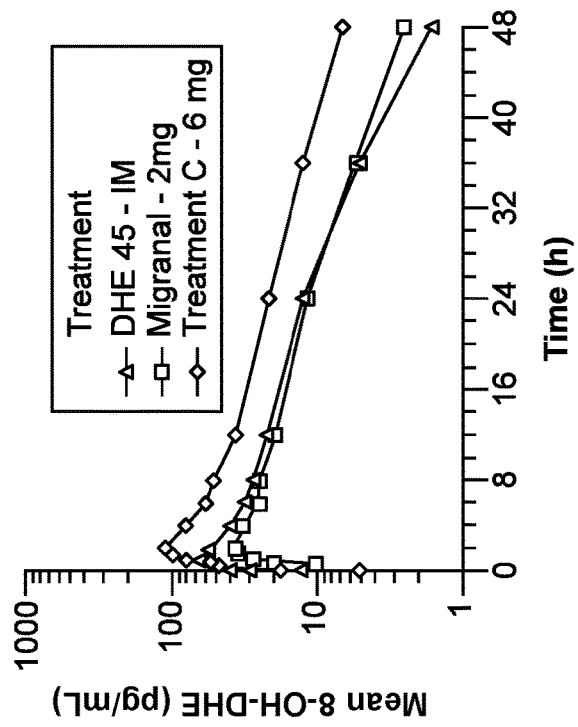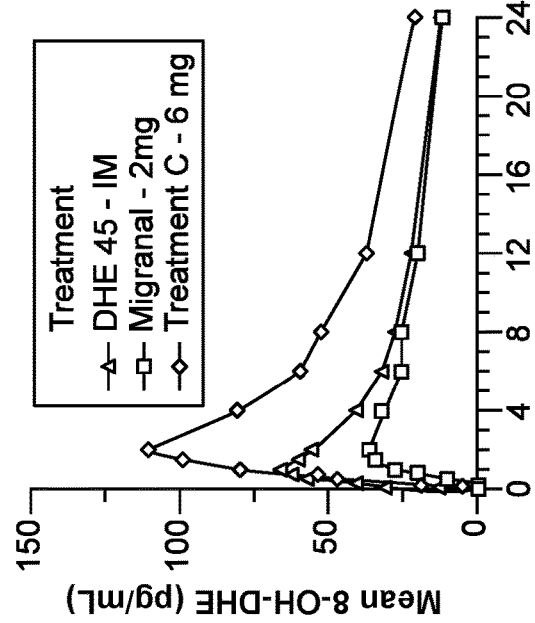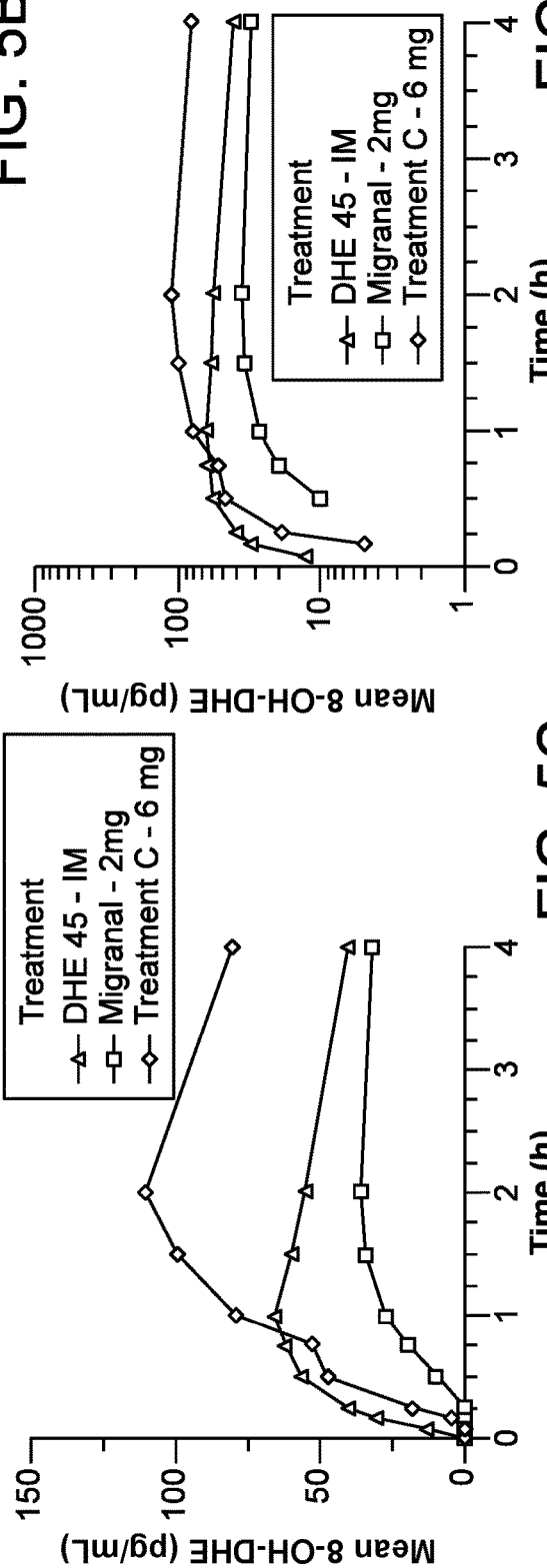

A total of 8 questions are listed in this assessment sheet. On the rating scale below, identify how much you are bothered by the BOLD symptom by placing a vertical line ( | ) on the line from "none" (left edge) to "worst imaginable" (right edge). This sheet will be filled out by each subject.

1. Please rate your overall nasal discomfort.
   none |—————————————————| worst imaginable 2. Please rate your nasal burning.
   none |—————————————————| worst imaginable 3. Please rate your nasal itching.
   none |—————————————————| worst imaginable 4. Please rate your nasal pain.
   none |—————————————————| worst imaginable 5. Please rate your nasal blockage or obstruction.
   none |—————————————————| worst imaginable 6. Please rate how much abnormal taste you experience.
   none |—————————————————| worst imaginable 7. Please rate how much runny nose you experience.
   none |—————————————————| worst imaginable 8. Please rate how much sneezing you experience.
   none |—————————————————| worst imaginable

FIG. 9

COMPOSITIONS, DEVICES, AND METHODS FOR TREATING OR PREVENTING HEADACHES

CROSS-REFERENCE

The present application claims the benefit of U.S. Provisional Patent Application No. 62/778,158 filed Dec. 11, 2018, U.S. Provisional Patent Application No. 62/799,635 filed Jan. 31, 2019, and U.S. Provisional Patent Application No. 62/847,607 filed May 14, 2019, the contents of each being hereby incorporated by reference in their entirety.

INCORPORATION BY REFERENCE

All publications, patents, and patent applications disclosed herein are incorporated by reference to the same extent as if each individual publication, patent, or patent application was specifically and individually indicated to be incorporated by reference. In the event of a conflict between a term disclosed herein and a term in an incorporated reference, the term herein controls.

BRIEF SUMMARY

The inventive embodiments provided in this Brief Summary are meant to be illustrative only and to provide an overview of selective embodiments disclosed herein. The Brief Summary, being illustrative and selective, does not limit the scope of any claim, does not provide the entire scope of inventive embodiments disclosed or contemplated herein, and should not be construed as limiting or constraining the scope of this disclosure or any claimed inventive embodiment.

In some of many aspects, provided herein is a method of treatment or prevention, comprising administering to a human subject a powdery pharmaceutical composition that comprises an active agent selected from the group consisting of a compound having a formula of:

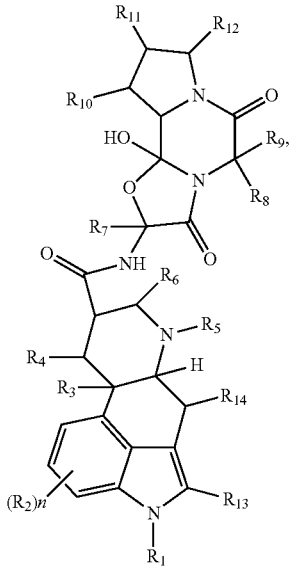

Formula (I)

a stereoisomer thereof, a pharmaceutically acceptable salt thereof, a complex thereof, a chelate thereof, a hydrate thereof, a polymorph thereof, an ion pair thereof, and any combination thereof, wherein said method produces in said human subject a time to reach a peak plasma concentration ($T_{max}$) of 90 minutes or longer for a metabolite of said active agent, as determined from measurement of a human plasma concentration of said metabolite by liquid chromatography-tandem mass spectrometry with automated extraction, and wherein:

$R_1$ is hydrogen, ($C_1$-$C_4$) alkyl, or ($C_1$-$C_4$) perfluoroalkyl;
each $R_2$ is independently hydrogen, halogen, alkyl, acyl, heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$, or —$CO_2R_{107}$;
$R_3$ and $R_4$ are independently hydrogen, deuterium, halogen, hydroxy, or methoxy;
$R_5$, $R_6$, and $R_7$ are independently hydrogen, ($C_1$-$C_3$) alkyl, or ($C_1$-$C_3$) perfluoroalkyl;
$R_8$ and $R_9$ are independently hydrogen, ($C_1$-$C_4$) alkyl, or benzyl;
$R_{10}$, $R_{11}$, $R_{12}$, and $R_{14}$ are independently hydrogen, halogen, —OH, ($C_1$-$C_4$) alkyl, —$CO_2R_{108}$, or —$CONR_{109}R_{110}$;
$R_{13}$ is hydrogen or halogen;
$R_{101}$-$R_{110}$ are independently hydrogen, halogen, alkyl, acyl, aryl, arylalkyl, heteroalkyl, heteroaryl, or heteroarylalkyl;
k is 0, 1, or 2; and
n is 0, 1, 2, or 3.

In some instances, said $T_{max}$ is at least about 2 hours. In some instances, a peak plasma concentration ($C_{max}$) of said metabolite is less than about 250 pg/ml, for example less than about 150 pg/ml. In some instances, a peak plasma concentration ($C_{max}$) of said metabolite is less than about 15%, for example less than about 10%, of a $C_{max}$ of said active agent measured following said administration to said human subject. In some instances, a plasma concentration of said metabolite is less than about 5% of a plasma concentration of said active agent measured within about 30 minutes following said administration to said human subject. In some instances, a plasma concentration of said metabolite is less than about 2% of a plasma concentration of said active agent measured within about 15 minutes following said administration to said human subject. In some instances, a reduced presence of said metabolite results in a reduced pharmacological effect from said metabolite in said human subject. In some instances, said reduced pharmacological effect is less than 20% binding activity at an adrenergic receptor (e.g., α[non-specific], α2A, α2B, α2C, β), dopaminergic (e.g., D: $D_1$, $D_2$, $D_3$), or serotonergic receptor (e.g., 5-HT receptor or subtypes: 5-$HT_{1A}$, 5-$HT_{1B}$, 5-$HT_{1D}$, 5-$HT_{2A}$, 5-$HT_{2C}$, 5-$HT_3$, 5-$HT_4$, 5-$HT_{5A}$, 5-$HT_6$, 5-$HT_7$) as measured by a radioligand competitive binding assay. In some instances, said reduced pharmacological effect in said human subject is In some instances, said reduced pharmacological effect in said human subject is manifested by: a reduced transcutaneous partial $O_2$ pressure as measured at the back of a foot, a reduced venous constrictive effect as determined using a venous occlusion mercury strain gauge, a less decreased diameter or compliance of a brachial artery wall, a decreased constrictive effect on a human coronary artery, meningeal artery, or saphenous vein, a less decreased venous diameter at a fixed occlusion pressure, a change in peripheral circulatory capacitance, or any combination thereof. In some instances, said $R_3$ and said $R_4$ are both hydrogen. In some instances, said active agent comprises dihydroergotamine or a pharmaceutically acceptable salt thereof. In some instances, said metabolite is of Formula (I) and wherein said $R_{12}$ is —OH. In some instances, said metabolite is 8'-hydroxy dihydroergotamine.

In some instances, said pharmaceutical composition comprises: about 1 mg to about 6 mg of said active agent, about 12 mg to about 19 mg of microcrystalline cellulose, about 0.1 mg to about 0.6 mg of a thickening agent, and about 6 mg to about 7 mg of a sugar alcohol. In some instances, said thickening agent is present in a weight amount that is about 10% of that of said active agent. In some instances, said thickening agent comprises hydroxypropyl methylcellulose. In some instances, said thickening agent comprises hydroxypropyl cellulose. In some instances, said thickening agent comprises carboxymethylcellulose. In some instances, said thickening agent is present in a spray dried particle dispersion. In some instances, said sugar alcohol comprises mannitol. In some instances, said sugar alcohol comprises sorbitol. In some instances, said sugar alcohol comprises galactitol. In some instances, said active agent is present in a spray-dried particle dispersion. In some instances, about 3 mg to about 13 mg of said microcrystalline cellulose is present in a spray-dried particle dispersion. In some instances, said microcrystalline cellulose is at least partially coated with said active agent. In some instances, said active agent is in an amorphous form. In some instances, said active agent is dihydroergotamine or a pharmaceutically acceptable salt thereof. In some instances, said pharmaceutical composition comprises said pharmaceutically acceptable salt of dihydroergotamine that is dihydroergotamine mesylate. In some instances, said pharmaceutical composition is a powdery pharmaceutical composition. In some instances, said administration is an intranasal administration. In some instances, said human subject experiences a relief of a migraine symptom (pain, photophobia, phonophobia, nausea, or any combination thereof) or a cranial autonomic symptom (conjunctival injection, eyelid oedema, miosis, ptosis, lacrimation, nasal congestion, rhinorrhoea, forehead/facial sweating, or any combination thereof) started within about 2 hours following said administration and lasting for up to 5 days. In some instances, said human subject experiences said relief started within about 45 minutes, about 30 minutes, or less following said administration. In some instances, said human subject experiences said relief sustained for up to 2 to 24 hours, 48 hours, 96 hours, or longer, following the start of a relief of a symptom after said administration. In some instances, said human subject is in a lying position. In some instances, said human subject is in a supine position. In some instances, said human subject is in a recovery position. In some instances, said human subject is in an upright position. In some instances, said method treats a headache. In some instances, said headache comprises a migraine. In some instances, said headache comprises a migraine headache with aura, a migraine headache without aura, a cluster migraine, cluster headache, post-traumatic headache, hemiplegic migraine, basilar migraine, episodic migraine, chronic migraine, refractory migraine, migraine attack (optionally when treatment is initiated at least 1-24 hours (e.g., 2 hours, 3 hours) after an onset of attack), migraine attack when treatment is initiated at the earliest premonitory sign or symptom, pediatric migraine, status migraine, chronic daily headache, a migraine attack with allodynia, menstrually-associated migraine, menstrual migraine, migraine-upon-awakening, or rapid-onset migraine. In some instances, said administration provides at least about a 10 percent higher dC/dT value compared to a dihydroergotamine liquid dosage form in a time period of $T_{0min}$ to $T_{15}$ min. In some instances, said administration provides a dC/dT value of at least about 1000 (pg/mL)/hr in a time period of $T_{0min}$ to $T_{15min}$. In some instances, said pharmaceutical composition is provided in a device configured for said administration to said human subject. In some instances, said device requires no priming or is a pre-primed device. In some instances, said device is actuatable with one hand. In some instances, said device is stored for about twelve months or less, at about 20° C. to about 25° C., and at about 60% relative humidity prior to actuating said device. In some instances, a reservoir housing said pharmaceutical composition in said device is free from metal or glass. In some instances, said device is free from metal or glass. In some instances, said administration requires less than about: 15, 10, 5, 4, 3, 2, 1, 0.5, or 0.25 minutes to deliver an effective dose of said active agent. In some instances, said pharmaceutical composition is in a single unit dose. In some instances, at least about 80% of said active agent is stable for a storage time period of at least about 60 days to about 3 years in a light-resistant closed container at a room temperature under one atmosphere with a relative humidity of less than about 50% outside said container, as measured by a liquid chromatography method. In some instances, said storage time period is at least about 1 year. In some instances, said administration is repeated about every 2-8 hours. In some instances, said administration is repeated about every 2-6 hours. In some instances, said administration is repeated for a time period of 1, 2, 3, 4, or 5 days. In some instances, said method further comprises monitoring a vital sign of said human subject. In some instances, said vital sign is at least one of blood pressure, heart rate, body temperature, respiration rate, oxygen saturation, or electrocardiogram. In some instances, said human subject performs said monitoring. In some instances, said monitoring comprises using an electronic device. In some instances, said electronic device is portable. In some instances, said electronic device is wearable. In some instances, said administration comprises delivering two or more doses of said pharmaceutical composition to said human subject, for example treating a cluster headache or cluster migraine. In some instances, said administration comprises delivering two or more doses of said pharmaceutical composition in two or more of said devices to said human subject. In some instances, each of said devices comprises a single unit dose of said pharmaceutical composition. In some instances, said two or more doses are administered in one of said device to said human subject. In some instances, said two or more doses are delivered successively to one or two nostrils of said human subject. In some instances, a first dose of said two or more doses is administered immediately sequential into two different nostrils of said human subject. In some instances, said sequential administrations are about 15 to about 60 seconds apart. In some instances, a first dose and a second dose of said two or more doses are separated by about: 1 hour, 2 hours, 2.5 hours, 3 hours, 3.5 hours, 4 hours, 5 hours, 6 hours, or longer.

In some aspects, provided herein is a method of treatment or prevention, comprising administering to a human subject a pharmaceutical composition that comprises an active agent selected from the group consisting of a compound having a formula of:

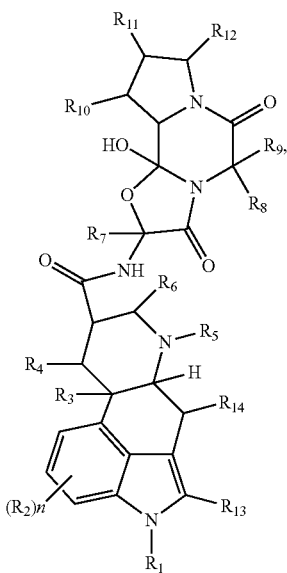

Formula (I)

a stereoisomer thereof, a pharmaceutically acceptable salt thereof, a complex thereof, a chelate thereof, a hydrate thereof, a polymorph thereof, an ion pair thereof, and any combination thereof, wherein said method produces in said human subject:
1) a $C_{max}$ of about 1 to about 2.5 ng/ml, or a plasma concentration of at least 1 ng/mL at about 10 minutes or shorter,
2) a $T_{max}$ of about 30 minutes or less, and
3) an AUC value selected from the group consisting of an $AUC_{0-30min}$ of about 500 to about 1000 h*pg/ml, an $AUC_{0-60min}$ of about 1000 to about 2000 h*pg/ml, an $AUC_{0-120min}$ of about 2000 to about 3000 h*pg/ml, an $AUC_{0-inf}$ of about 10000 to about 12000 h*pg/ml, and any combination thereof, as determined from measurement of a human plasma concentration of said active agent by liquid chromatography-tandem mass spectrometry with automated extraction, and wherein:

$R_1$ is hydrogen, $(C_1-C_4)$ alkyl, or $(C_1-C_4)$ perfluoroalkyl;
each $R_2$ is independently hydrogen, halogen, alkyl, acyl, heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$, or —$CO_2R_{107}$;
$R_3$ and $R_4$ are independently hydrogen, deuterium, halogen, hydroxy, or methoxy;
$R_5$, $R_6$, and $R_7$ are independently hydrogen, $(C_1-C_3)$ alkyl, or $(C_1-C_3)$ perfluoroalkyl;
$R_8$ and $R_9$ are independently hydrogen, $(C_1-C_4)$ alkyl, or benzyl;
$R_{10}$, $R_{11}$, $R_{12}$, and $R_{14}$ are independently hydrogen, halogen, —OH, $(C_1-C_4)$ alkyl, —$CO_2R_{108}$, or —$CONR_{109}R_{110}$;
$R_{13}$ is hydrogen or halogen;
$R_{101}$-$R_{110}$ are independently hydrogen, halogen, alkyl, acyl, aryl, arylalkyl, heteroalkyl, heteroaryl, or heteroarylalkyl;
k is 0, 1, or 2; and
n is 0, 1, 2, or 3.

In some instances, the method further provides a half-life of said active agent from about 12 hours to about 13 hours. In some instances, said $R_3$ and said $R_4$ are both hydrogen. In some instances, said active agent comprises dihydroergotamine or a pharmaceutically acceptable salt thereof. In some instances, wherein said $R_{12}$ is —OH. In some instances, said pharmaceutical composition comprises: about 1 mg to about 6 mg of said active agent, about 12 mg to about 19 mg of microcrystalline cellulose, about 0.1 mg to about 0.6 mg of a thickening agent, and about 6 mg to about 7 mg of a sugar alcohol. In some instances, said thickening agent is present in a weight amount that is about 10% of that of said active agent. In some instances, said thickening agent comprises hydroxypropyl methylcellulose. In some instances, said thickening agent comprises hydroxypropyl cellulose. In some instances, said thickening agent comprises carboxymethylcellulose. In some instances, said thickening agent is present in a spray dried particle dispersion. In some instances, said sugar alcohol comprises mannitol. In some instances, said sugar alcohol comprises sorbitol. In some instances, said sugar alcohol comprises galactitol. In some instances, said active agent is present in a spray-dried particle dispersion. In some instances, about 3 mg to about 13 mg of said microcrystalline cellulose is present in a spray-dried particle dispersion. In some instances, said microcrystalline cellulose is at least partially coated with said active agent. In some instances, said active agent is in an amorphous form. In some instances, said active agent is dihydroergotamine or a pharmaceutically acceptable salt thereof. In some instances, said pharmaceutical composition comprises said pharmaceutically acceptable salt of dihydroergotamine that is dihydroergotamine mesylate. In some instances, said pharmaceutical composition is a powdery pharmaceutical composition. In some instances, said administration is an intranasal administration. In some instances, said human subject experiences a relief of a migraine symptom (pain, photophobia, phonophobia, nausea, or any combination thereof) or a cranial autonomic symptom (conjunctival injection, eyelid oedema, miosis, ptosis, lacrimation, nasal congestion, rhinorrhoea, forehead/facial sweating, or any combination thereof) started within about 2 hours following said administration and lasting for up to 5 days. In some instances, said human subject experiences said relief started within about 45 minutes, about 30 minutes, or less following said administration. In some instances, said human subject experiences said relief sustained for up to 2 to 24 hours, 48 hours, 96 hours, or longer, following the start of a relief of a symptom after said administration. In some instances, said human subject is in a lying position. In some instances, said human subject is in a supine position. In some instances, said human subject is in a recovery position. In some instances, said human subject is in an upright position. In some instances, said method treats a headache. In some instances, said headache comprises a migraine. In some instances, said headache comprises a migraine headache with aura, a migraine headache without aura, a cluster migraine, cluster headache, post-traumatic headache, hemiplegic migraine, basilar migraine, episodic migraine, chronic migraine, refractory migraine, migraine attack (optionally when treatment is initiated at least 1-24 hours (e.g., 2 hours, 3 hours) after an onset of attack), migraine attack when treatment is initiated at the earliest premonitory sign or symptom, pediatric migraine, status migraine, chronic daily headache, a migraine attack with allodynia, menstrually-associated migraine, menstrual migraine, migraine-upon-awakening, or rapid-onset migraine. In some instances, said administration provides at least about a 10 percent higher dC/dT value compared to a dihydroergotamine liquid dosage form in a time period of $T_{0min}$ to $T_{15min}$. In some instances, said administration provides a dC/dT value of at least about 1000 (pg/mL)/hr in a time period of $T_{0min}$ to $T_{15min}$. In some instances, said pharmaceutical composition is provided in a device configured for said administration to said human subject. In some instances, said device requires no priming or is a pre-primed device. In some instances, said device is actuatable with one hand. In some instances, said device is stored for about twelve months or less, at about 20° C. to about 25° C., and at about 60% relative humidity prior to actuating said device. In some instances, a reservoir housing said pharmaceutical composition in said device is free from metal or glass. In some instances, said device is free from metal or glass. In some instances, said administration requires less than about: 15, 10, 5, 4, 3, 2, 1, 0.5, or 0.25 minutes to deliver an effective dose of said active agent. In some instances, said pharmaceutical composition is in a single unit dose. In some instances, at least about 80% of said active agent is stable for a storage time period of at least about 60 days to about 3 years in a light-resistant closed container at a room temperature under one atmosphere with a relative humidity of less than about 50% outside said container, as measured by a liquid chromatography method. In some instances, said storage time period is at least about 1 year. In some instances, said administration is repeated about every 2-8 hours. In some instances, said administration is repeated about every 2-6 hours. In some instances, said administration is repeated for a time period of 1, 2, 3, 4, or 5 days. In some instances, said method further comprises monitoring a vital sign of said human subject. In some instances, said vital sign is at least one of blood pressure, heart rate, body temperature, respiration rate, oxygen saturation, or electrocardiogram. In some instances, said human subject performs said monitoring. In some instances, said monitoring comprises using an electronic device. In some instances, said electronic device is portable. In some instances, said electronic device is wearable. In some instances, said administration comprises delivering two or more doses of said pharmaceutical composition to said human subject, for example treating a cluster headache or cluster migraine. In some instances, said administration comprises delivering two or more doses of said pharmaceutical composition in two or more of said devices to said human subject. In some instances, each of said devices comprises a single unit dose of said pharmaceutical composition. In some instances, said two or more doses are administered in one of said device to said human subject. In some instances, said two or more doses are delivered successively to one or two nostrils of said human subject. In some instances, a first dose of said two or more doses is administered immediately sequential into two different nostrils of said human subject. In some instances, said sequential administrations are about 15 to about 60 seconds apart. In some instances, a first dose and a second dose of said two or more doses are separated by about: 1 hour, 2 hours, 2.5 hours, 3 hours, 3.5 hours, 4 hours, 5 hours, 6 hours, or longer.

In some aspects, provided herein is a method of treatment or prevention, comprising administering to a human subject a pharmaceutical composition that comprises an active agent selected from the group consisting of a compound having a formula of:

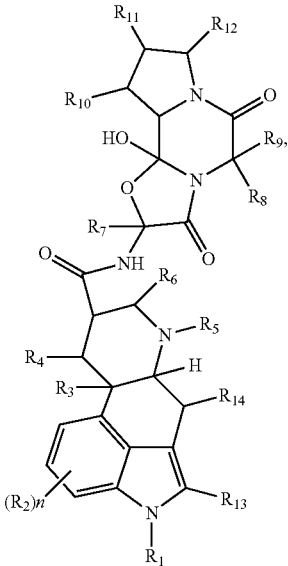

Formula (I)

a stereoisomer thereof, a pharmaceutically acceptable salt thereof, a complex thereof, a chelate thereof, a hydrate thereof, a polymorph thereof, an ion pair thereof, and any combination thereof, wherein said method produces an apparent clearance (CL/F) value of said active agent from about 100 L/hr to about 1000 L/hr following said administration to said human subject, and wherein:

$R_1$ is hydrogen, $(C_1$-$C_4)$ alkyl, or $(C_1$-$C_4)$ perfluoroalkyl;

each $R_2$ is independently hydrogen, halogen, alkyl, acyl, heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$, or —$CO_2R_{107}$;

$R_3$ and $R_4$ are independently hydrogen, deuterium, halogen, hydroxy, or methoxy;

$R_5$, $R_6$, and $R_7$ are independently hydrogen, $(C_1$-$C_3)$ alkyl, or $(C_1$-$C_3)$ perfluoroalkyl;

$R_8$ and $R_9$ are independently hydrogen, $(C_1$-$C_4)$ alkyl, or benzyl;

$R_{10}$, $R_{11}$, $R_{12}$, and $R_{14}$ are independently hydrogen, halogen, —OH, $(C_1$-$C_4)$ alkyl, —$CO_2R_{108}$, or —$CONR_{109}R_{110}$;

$R_{13}$ is hydrogen or halogen;

$R_{101}$-$R_{110}$ are independently hydrogen, halogen, alkyl, acyl, aryl, arylalkyl, heteroalkyl, heteroaryl, or heteroarylalkyl;

k is 0, 1, or 2; and n is 0, 1, 2, or 3.

In some instances, said CL/F value of said active agent is about 540 L/hr. In some instances, said $R_3$ and said $R_4$ are both hydrogen. In some instances, said active agent comprises dihydroergotamine or a pharmaceutically acceptable salt thereof. In some instances, wherein said $R_{12}$ is —OH. In some instances, said pharmaceutical composition comprises: about 1 mg to about 6 mg of said active agent, about 12 mg to about 19 mg of microcrystalline cellulose, about 0.1 mg to about 0.6 mg of a thickening agent, and about 6 mg to about 7 mg of a sugar alcohol. In some instances, said thickening agent is present in a weight amount that is about 10% of that of said active agent. In some instances, said thickening agent comprises hydroxypropyl methylcellulose. In some instances, said thickening agent comprises hydroxypropyl cellulose. In some instances, said thickening agent comprises carboxymethylcellulose. In some instances, said thickening agent is present in a spray dried particle dispersion. In some instances, said sugar alcohol comprises mannitol. In some instances, said sugar alcohol comprises sorbitol. In some instances, said sugar alcohol comprises galactitol. In some instances, said active agent is present in a spray-dried particle dispersion. In some instances, about 3 mg to about 13 mg of said microcrystalline cellulose is present in a spray-dried particle dispersion. In some instances, said microcrystalline cellulose is at least partially coated with said active agent. In some instances, said active agent is in an amorphous form. In some instances, said active agent is dihydroergotamine or a pharmaceutically acceptable salt thereof. In some instances, said pharmaceutical composition comprises said pharmaceutically acceptable salt of dihydroergotamine that is dihydroergotamine mesylate. In some instances, said pharmaceutical composition is a powdery pharmaceutical composition. In some instances, said administration is an intranasal administration. In some instances, said human subject experiences a relief of a migraine symptom (pain, photophobia, phonophobia, nausea, or any combination thereof) or a cranial autonomic symptom (conjunctival injection, eyelid oedema, miosis, ptosis, lacrimation, nasal congestion, rhinorrhoea, forehead/facial sweating, or any combination thereof) started within about 2 hours following said administration and lasting for up to 5 days. In some instances, said human subject experiences said relief started within about 45 minutes, about 30 minutes, or less following said administration. In some instances, said human subject experiences said relief sustained for up to 2 to 24 hours, 48 hours, 96 hours, or longer, following the start of a relief of a symptom after said administration. In some instances, said human subject is in a lying position. In some instances, said human subject is in a supine position. In some instances, said human subject is in a recovery position. In some instances, said human subject is in an upright position. In some instances, said method treats a headache. In some instances, said headache comprises a migraine. In some instances, said headache comprises a migraine headache with aura, a migraine headache without aura, a cluster migraine, cluster headache, post-traumatic headache, hemiplegic migraine, basilar migraine, episodic migraine, chronic migraine, refractory migraine, migraine attack (optionally when treatment is initiated at least 1-24 hours (e.g., 2 hours, 3 hours) after an onset of attack), migraine attack when treatment is initiated at the earliest premonitory sign or symptom, pediatric migraine, status migraine, chronic daily headache, a migraine attack with allodynia, menstrually-associated migraine, menstrual migraine, migraine-upon-awakening, or rapid-onset migraine. In some instances, said administration provides at least about a 10 percent higher dC/dT value compared to a dihydroergotamine liquid dosage form in a time period of $T_{0min}$ to $T_{15min}$. In some instances, said administration provides a dC/dT value of at least about 1000 (pg/mL)/hr in a time period of $T_{0min}$ to $T_{15min}$. In some instances, said pharmaceutical composition is provided in a device configured for said administration to said human subject. In some instances, said device requires no priming or is a pre-primed device. In some instances, said device is actuatable with one hand. In some instances, said device is stored for about twelve months or less, at about 20° C. to about 25° C., and at about 60% relative humidity prior to actuating said device. In some instances, a reservoir housing said pharmaceutical composition in said device is free from metal or glass. In some instances, said device is free from metal or glass. In some instances, said administration requires less than about: 15, 10, 5, 4, 3, 2, 1, 0.5, or 0.25 minutes to deliver an effective dose of said active agent. In some instances, said pharmaceutical composition is in a single unit dose. In some instances, at least about 80% of said active agent is stable for a storage time period of at least about 60 days to about 3 years in a light-resistant closed container at a room temperature under one atmosphere with a relative humidity of less than about 50% outside said container, as measured by a liquid chromatography method. In some instances, said storage time period is at least about 1 year. In some instances, said administration is repeated about every 2-8 hours. In some instances, said administration is repeated about every 2-6 hours. In some instances, said administration is repeated for a time period of 1, 2, 3, 4, or 5 days. In some instances, said method further comprises monitoring a vital sign of said human subject. In some instances, said vital sign is at least one of blood pressure, heart rate, body temperature, respiration rate, oxygen saturation, or electrocardiogram. In some instances, said human subject performs said monitoring. In some instances, said monitoring comprises using an electronic device. In some instances, said electronic device is portable. In some instances, said electronic device is wearable. In some instances, said administration comprises delivering two or more doses of said pharmaceutical composition to said human subject, for example treating a cluster headache or cluster migraine. In some instances, said administration comprises delivering two or more doses of said pharmaceutical composition in two or more of said devices to said human subject. In some instances, each of said devices comprises a single unit dose of said pharmaceutical composition. In some instances, said two or more doses are administered in one of said device to said human subject. In some instances, said two or more doses are delivered successively to one or two nostrils of said human subject. In some instances, a first dose of said two or more doses is administered immediately sequential into two different nostrils of said human subject. In some instances, said sequential administrations are about 15 to about 60 seconds apart. In some instances, a first dose and a second dose of said two or more doses are separated by about: 1 hour, 2 hours, 2.5 hours, 3 hours, 3.5 hours, 4 hours, 5 hours, 6 hours, or longer.

In some aspects, provided herein is a method of treatment or prevention, comprising administering to a human subject a pharmaceutical composition that comprises an active agent selected from the group consisting of a compound having a formula of:

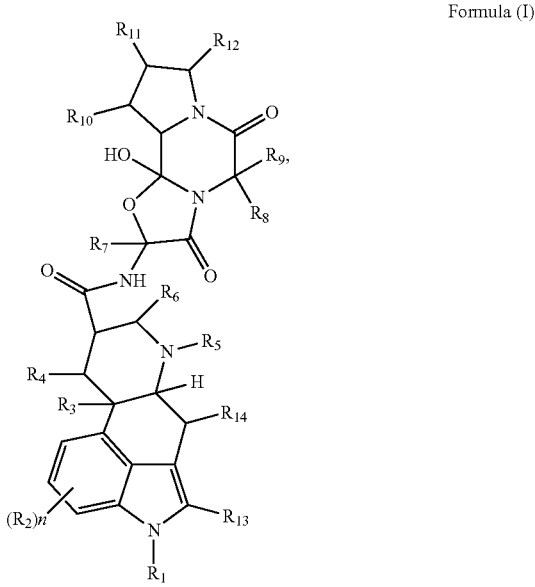

Formula (I)

a stereoisomer thereof, a pharmaceutically acceptable salt thereof, a complex thereof, a chelate thereof, a hydrate thereof, a polymorph thereof, an ion pair thereof, and any combination thereof, wherein said method produces a Visual Analog Scale score for measurement of a nasal symptom less than about 20 when measured within 24 hours following said administration to said human subject, wherein said Visual Analog Scale score is measured in a scale of 0 (none) to 100 (worst imaginable) based on each of the following nasal symptoms: nasal discomfort, nasal burning, nasal itching, nasal pain, nasal blockage or obstruction, abnormal taste, runny nose, and sneezing, and wherein:

$R_1$ is hydrogen, $(C_1-C_4)$ alkyl, or $(C_1-C_4)$ perfluoroalkyl;

each $R_2$ is independently hydrogen, halogen, alkyl, acyl, heteroalkyl, $-NO_2$, $-N_3$, $-OH$, $-S(O)_kR_{100}$, $-OR_{101}$, $-NR_{102}R_{103}$, $-CONR_{104}R_{105}$, $-CO_2R_{106}$, or $-CO_2R_{107}$;

$R_3$ and $R_4$ are independently hydrogen, deuterium, halogen, hydroxy, or methoxy;

$R_5$, $R_6$, and $R_7$ are independently hydrogen, $(C_1-C_3)$ alkyl, or $(C_1-C_3)$ perfluoroalkyl;

$R_8$ and $R_9$ are independently hydrogen, $(C_1-C_4)$ alkyl, or benzyl;

$R_{10}$, $R_{11}$, $R_{12}$, and $R_{14}$ are independently hydrogen, halogen, $-OH$, $(C_1-C_4)$ alkyl, $-CO_2R_{108}$, or $-CONR_{109}R_{110}$;

$R_{13}$ is hydrogen or halogen;

$R_{101}$-$R_{110}$ are independently hydrogen, halogen, alkyl, acyl, aryl, arylalkyl, heteroalkyl, heteroaryl, or heteroarylalkyl;

k is 0, 1, or 2; and n is 0, 1, 2, or 3.

In some instances, the method herein does not cause health normal subject clinically significant changes in vital signs, nasal mucosa integrity, and nasal irritation. In some instances, said Visual Analog Scale score is measured at about 4 hours following said administration. In some instances, said Visual Analog Scale score is measured at about 1 hour following said administration. In some instances, said Visual Analog Scale score is measured at about 15 minutes following said administration. In some instances, said Visual Analog Scale score is measured at about 5 minutes following said administration. In some instances, said Visual Analog Scale score is less than about 10. In some instances, said Visual Analog Scale score is less than about 5. In some instances, said Visual Analog Scale score is 0. In some instances, said $R_3$ and said $R_4$ are both hydrogen. In some instances, said active agent comprises dihydroergotamine or a pharmaceutically acceptable salt thereof. In some instances, wherein said $R_{12}$ is $-OH$. In some instances, said pharmaceutical composition comprises: about 1 mg to about 6 mg of said active agent, about 12 mg to about 19 mg of microcrystalline cellulose, about 0.1 mg to about 0.6 mg of a thickening agent, and about 6 mg to about 7 mg of a sugar alcohol. In some instances, said thickening agent is present in a weight amount that is about 10% of that of said active agent. In some instances, said thickening agent comprises hydroxypropyl methylcellulose. In some instances, said thickening agent comprises hydroxypropyl cellulose. In some instances, said thickening agent comprises carboxymethylcellulose. In some instances, said thickening agent is present in a spray dried particle dispersion. In some instances, said sugar alcohol comprises mannitol. In some instances, said sugar alcohol comprises sorbitol. In some instances, said sugar alcohol comprises galactitol. In some instances, said active agent is present in a spray-dried particle dispersion. In some instances, about 3 mg to about 13 mg of said microcrystalline cellulose is present in a spray-dried particle dispersion. In some instances, said microcrystalline cellulose is at least partially coated with said active agent. In some instances, said active agent is in an amorphous form. In some instances, said active agent is dihydroergotamine or a pharmaceutically acceptable salt thereof. In some instances, said pharmaceutical composition comprises said pharmaceutically acceptable salt of dihydroergotamine that is dihydroergotamine mesylate. In some instances, said pharmaceutical composition is a powdery pharmaceutical composition. In some instances, said administration is an intranasal administration. In some instances, said human subject experiences a relief of a migraine symptom (pain, photophobia, phonophobia, nausea, or any combination thereof) or a cranial autonomic symptom (conjunctival injection, eyelid oedema, miosis, ptosis, lacrimation, nasal congestion, rhinorrhoea, forehead/facial sweating, or any combination thereof) started within about 2 hours following said administration and lasting for up to 5 days. In some instances, said human subject experiences said relief started within about 45 minutes, about 30 minutes, or less following said administration. In some instances, said human subject experiences said relief sustained for up to 2 to 24 hours, 48 hours, 96 hours, or longer, following the start of a relief of a symptom after said administration. In some instances, said human subject is in a lying position. In some instances, said human subject is in a supine position. In some instances, said human subject is in a recovery position. In some instances, said human subject is in an upright position. In some instances, said method treats a headache. In some instances, said headache comprises a migraine. In some instances, said headache comprises a migraine headache with aura, a migraine headache without aura, a cluster migraine, cluster headache, post-traumatic headache, hemiplegic migraine, basilar migraine, episodic migraine, chronic migraine, refractory migraine, migraine attack (optionally when treatment is initiated at least 1-24 hours (e.g., 2 hours, 3 hours) after an onset of attack), migraine attack when treatment is initiated at the earliest premonitory sign or symptom, pediatric migraine, status migraine, chronic daily headache, a migraine attack with allodynia, menstrually-associated migraine, menstrual migraine, migraine-upon-awakening, or rapid-onset migraine. In some instances, said administration provides at least about a 10 percent higher dC/dT value compared to a dihydroergotamine liquid dosage form in a time period of $T_{0min}$ to $T_{15min}$. In some instances, said administration provides a dC/dT value of at least about 1000 (pg/mL)/hr in a time period of $T_{0min}$ to $T_{15min}$. In some instances, said pharmaceutical composition is provided in a device configured for said administration to said human subject. In some instances, said device requires no priming or is a pre-primed device. In some instances, said device is actuatable with one hand. In some instances, said device is stored for about twelve months or less, at about 20° C. to about 25° C., and at about 60% relative humidity prior to actuating said device. In some instances, a reservoir housing said pharmaceutical composition in said device is free from metal or glass. In some instances, said device is free from metal or glass. In some instances, said administration requires less than about: 15, 10, 5, 4, 3, 2, 1, 0.5, or 0.25 minutes to deliver an effective dose of said active agent. In some instances, said pharmaceutical composition is in a single unit dose. In some instances, at least about 80% of said active agent is stable for a storage time period of at least about 60 days to about 3 years in a light-resistant closed container at a room temperature under one atmosphere with a relative humidity of less than about 50% outside said container, as measured by a liquid chromatography method. In some instances, said storage time period is at least about 1 year. In some instances, said administration is repeated about every 2-8 hours. In some instances, said administration is repeated about every 2-6 hours. In some instances, said administration is repeated for a time period of 1, 2, 3, 4, or 5 days. In some instances, said method further comprises monitoring a vital sign of said human subject. In some instances, said vital sign is at least one of blood pressure, heart rate, body temperature, respiration rate, oxygen saturation, or electrocardiogram. In some instances, said human subject performs said monitoring. In some instances, said monitoring comprises using an electronic device. In some instances, said electronic device is portable. In some instances, said electronic device is wearable. In some instances, said administration comprises delivering two or more doses of said pharmaceutical composition to said human subject, for example treating a cluster headache or cluster migraine. In some instances, said administration comprises delivering two or more doses of said pharmaceutical composition in two or more of said devices to said human subject. In some instances, each of said devices comprises a single unit dose of said pharmaceutical composition. In some instances, said two or more doses are administered in one of said device to said human subject. In some instances, said two or more doses are delivered successively to one or two nostrils of said human subject. In some instances, a first dose of said two or more doses is administered immediately sequential into two different nostrils of said human subject. In some instances, said sequential administrations are about 15 to about 60 seconds apart. In some instances, a first dose and a second dose of said two or more doses are separated by about: 1 hour, 2 hours, 2.5 hours, 3 hours, 3.5 hours, 4 hours, 5 hours, 6 hours, or longer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative instances, in which the principles of the invention are utilized, and the accompanying drawings (also "figure" and "FIG." herein), of which:

FIG. 1A shows an exemplary device filled with a powder formulation. FIG. 1B shows different illustration styles of parts of an exemplary device without a formulation.

FIGS. 2A, 2B, and 2C show a cross-sectional view of additional exemplary delivery devices.

FIGS. 5A to 5D show mean 8'-OH-DHE plasma concentration over time in the treatments for Part 2 of the Clinical Phase 1 study described in Example 4, in a linear plot in the time course of 24 hours (FIG. 5A), in a log-linear plot in the time course of 48 hours (FIG. 5B), a linear plot in the time course of 0-4 hours (FIG. 5C), and a log-linear plot in the time course of 0-4 hours (FIG. 5D).

FIG. 9 shows an exemplary visual analog scale (VAS) for assessment of symptoms after the treatments.

DETAILED DESCRIPTION

Figure 2C:
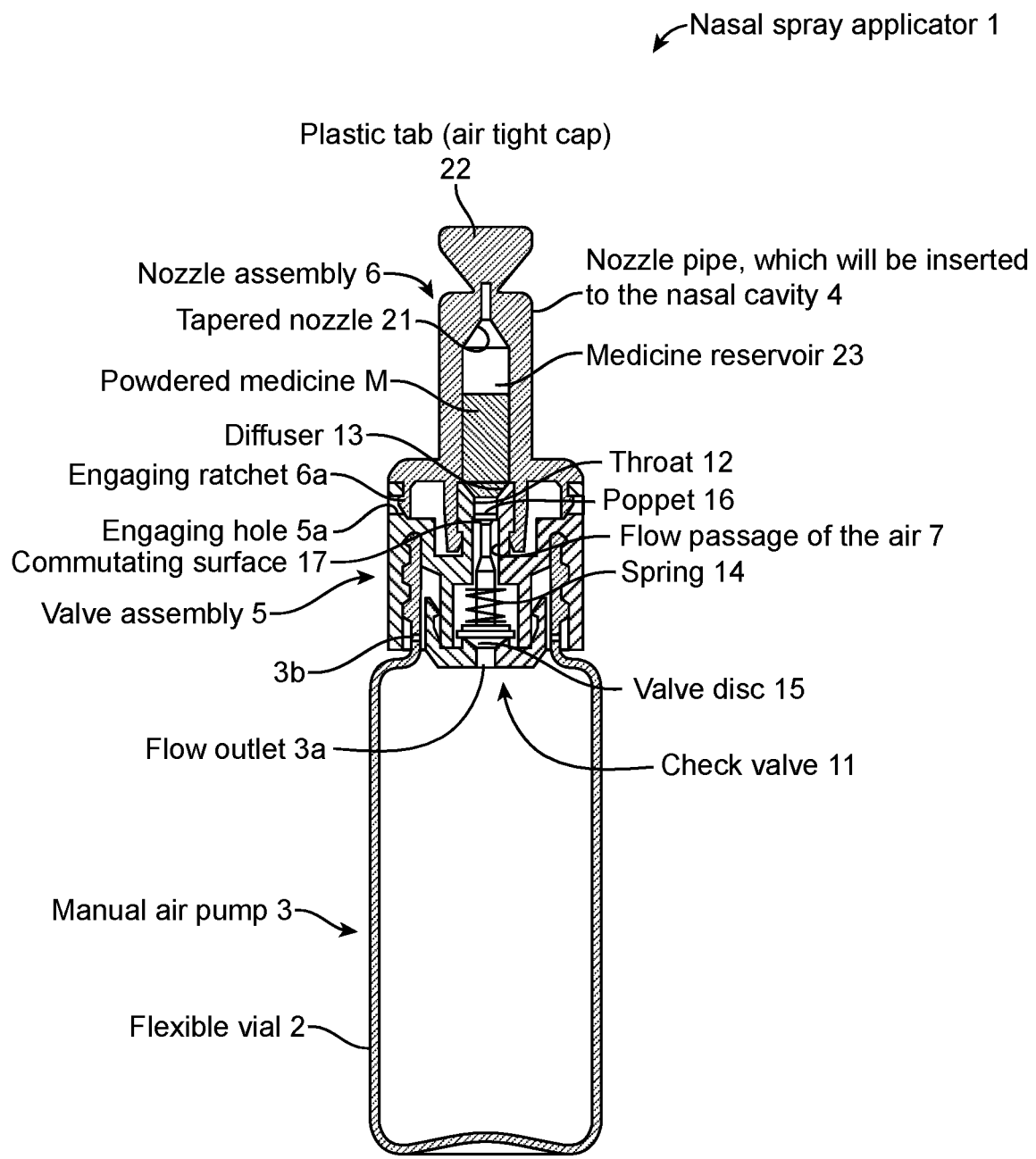

The present disclosure provides new methods of medical treatment or prevention (e.g., for headaches) resulting in unexpected superior pharmacokinetics compared to conventional methods. In some instances, the methods herein can produce a unique pharmacokinetic profile of a metabolite. In some instances, the methods herein can employ a drug-device combination, e.g., for intranasal delivery. In some instances, the methods can comprise delivering a pharmaceutical composition to a subject with a device disclosed herein, in one, two, or more doses. In some instances, such drug-device combination can consistently deliver clinical doses and have optimal aerodynamic particle size for nasal deposition with negligible respirable fine particle fraction that may deposit in the lung. In some instances, such drug-device combination can produce a consistent and robust delivery even with suboptimal actuation. In some instances, a device for delivery requires no priming or a pre-primed device. In some instances, the methods herein provide consistent and robust drug delivery performances. In some instances, the methods herein further comprise monitoring a vital sign of a subject who receives the treatment or prevention and may perform said monitoring himself/herself, for example with a portable or wearable electronic device. The present disclosure also provides new pharmaceutical compositions, for example an active agent such as dihydroergotamine mesylate with a selection of excipients in particular weight amounts. In some instances, the methods and/or compositions herein can satisfy the unmet need for a reliable non-parenteral form of dihydroergotamine.

Unless defined otherwise, all technical and scientific terms used herein have the same meaning as commonly understood by one of the ordinary skill in the art to which this invention belongs. Although any methods and materials similar or equivalent to those described herein can be used in the practice or testing of the compositions or unit doses herein, some methods and materials are now described. Unless mentioned otherwise, the techniques employed or contemplated herein are standard methodologies. The materials, methods and examples are illustrative only and not limiting.

The details of one or more inventive instances are set forth in the accompanying drawings, the claims, and the description herein. Other instances, features, objects, and advantages of the inventive instances disclosed and contemplated herein can be combined with any other instance unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some instances herein contemplate numerical ranges. When a numerical range is provided, unless otherwise indicated, the range includes the range endpoints. Unless otherwise indicated, numerical ranges include all values and subranges therein as if explicitly written out. Unless otherwise indicated, any numerical ranges and/or values herein can be at 80-120% of the numerical ranges and/or values. For example, the term "about" can mean the referenced numeric indication plus or minus 20% of that referenced numeric indication.

The term "subject" as used herein can refer to a mammal (e.g., a human, mouse, rat, guinea pig, dog, cat, horse, cow, pig, or non-human primate, such as a monkey, chimpanzee or baboon). In some instances, the subject is a human subject. In some instances, the subject is a human subject. In some instances, the subject is a healthy human subject. In some instances, the subject is a human in need of a treatment or prevention of a condition or disorder.

In some instances, improvement is calculated as the following:

$$\text{Improvement} = (|I-C|/C) \times D_1/D_c \times 100\%$$

I=Improved value from a present composition
C=Control value from a comparator or conventional composition
$D_1$=Dose of the present composition
$D_c$=Dose of the comparator or conventional composition Unless otherwise indicated, relative bioavailability (rBA) is equal to [(AUC of preparation with amorphous Active Pharmaceutical Ingredient/Dose of preparation with amorphous)/(AUC of preparation with 100% crystal/Dose of preparation of 100% crystal)×100%].

The term "dC/dT" as used herein can refer to change in an active agent concentration in plasma as a function of time or change in plasma concentration of an active agent during said time period or interval. It is calculated as dC/dT= (Plasma Concentration at T2−Plasma Concentration at T1)/ (Time point T2−Time point T1).

The term "pre-primed," as used herein can refer to a device, such as a nasal delivery device, which is capable of delivering a nasal dosage form to a human subject in need thereof, without the need to assemble the device, or with the first actuation of a pump of the device, i.e., without the need to prime (pumping the nasal spray or puff) the pump prior to dosing.

Pharmacokinetic data disclosed herein (e.g., $C_{max}$, $T_{max}$, $AUC_{0-t}$, $AUC_{0-180}$ minutes, $AUC_{0-inf}$, $T_{1/2}$) can be measured from a primate, for example a monkey such as a Cynomolgus monkey, after a composition disclosed herein is administered. Alternatively, the pharmacokinetic data disclosed herein (e.g., $C_{max}$, $T_{max}$, $AUC_{0-t}$, $AUC_{0-180}$ minutes, $AUC_{0-inf}$, $T_{1/2}$) can be measured from a human subject after a composition disclosed herein is administered. In some instances, an active agent such as dihydroergotamine, or a complex, chelate, salt, hydrate, polymorph, or ion pair thereof is administered at a rate such that a mean peak plasma concentration ($C_{max}$) of 8-hydroxy dihydroergotamine is higher than 10,000 pg/ml, a mean time to $C_{max}$ ($T_{max}$) of 8-hydroxy dihydroergotamine is 90 minutes or longer, or a combination thereof.

In some instances, the term "substantially" can mean 80-100% of a referred subject matter.

In some instances, an agglomerate can mean a loose accumulation of separate particles bonded by weak physical forces.

In some instances, an aggregate can mean a dense cluster of separate particles bonded by strong chemical or sinter forces.

Intranasal administration, as used herein can refer to administration whereby at least 90±10%, e.g., 95±5%, of the composition is administered to the nasal cavity as measured by multiple path particle dosimetry (MPPD) model analysis, a computational model used to estimate human airway particle dosimetry, or via an Andersen Cascade Impactor.

In a Markush group, any combination of members in the Markush group is contemplated.

Unless otherwise indicated, the term "thickening agent" can refer to an excipient that increases a particle size of an active agent and/or viscosity of a composition. In some instances, a thickening agent disclosed herein binds to an active agent and/or a carrier via a non-covalent interaction, e.g., hydrogen bonding or van der Waals force.

Unless otherwise indicated, "average particle size" can refer to a particle size distribution of a powder in its non-aggregated state. In some instances, an average particle size can refer to a mean particle size, for example calculated as a sum of size measurements of all measurable particles divided by a total number of particles measured. In some instances, an average particle size can refer to a median particle size, for example indicating that about 50% of all measurable particles measured have a particle size less than the defined median particle size value, and that about 50% of all measurable particles measured have a particle size greater than the defined median particle size value. In some instances, an average particle size can refer to a mode particle size, for example indicating the most frequently-occurring particle size value. In some instances, for spherical particles, an average particle size can be a measurement of a particle's diameter. In some instances, for non-spherical particles, an average particle size can be a measurement of longest or shortest diameters, perimeter, projected area, or by an equivalent spherical diameter. In some instances, an average particle diameter can be determined using a laser-diffraction particle size analyzer. In some instances, the particle size analyzer can be Mastersizer 2000 manufactured by Malvern Instruments Limited. In some instances, an average particle diameter can be an aerodynamic particle size, for example as measured by a Next Generation Impactor or Mercer Cascade Impactor.

Active Agents and Compositions

In some cases, an active agent disclosed herein can be a non-peptide/non-protein drug. In some instances, the active agent can be selected from the group consisting of ergot alkaloid, 5-hydroxytryptamine1 (5-HT$_1$) receptor agonist, CGRP antagonist, NK-1 receptor antagonist, antihistamine, antiemetic agent, decongestant, opioid receptor agonist, antibiotic, antifungal agent, sulfa drug, antituberculosis drug, antimicrobial agent, antiviral agent, hypnotic sedative, antiepileptic agent, narcotic analgesic, non-narcotic analgesic, sedative drug, psychotherapeutic agent, muscle relaxant, antiallergic agent, anti-rheumatic drug, cardiotonic drug, antiarrhythmic agent, antihypertensive agent, diuretic agent, coronary vasodilator, antidementia drug, brain activator, brain circulation ameliorating agent, antiparkinsonian agent, antihyperlipidemic drug, antiulcer drug, obesity drug, diabetic drug, hemostatic drug, antithrombotic agent, migraine drug, antitussive drug, expectorant, respiratory stimulant, asthma drug, antidiarrheal drug, nonsteroidal anti-inflammatory agent, antipodagric, therapeutic agent for urinary disease, drug for improving sexual function, agent for the uterus, steroid, prostaglandin, vitamin, antidote, therapeutic agent for heavy metal toxification, quit smoking agent, antianaphylactic agent, antitumor agent, immunostimulator, immunosuppressive drug, and any combination thereof. In some instances, the active agent can be selected from the group consisting of didanosine, zidovudine, lamivudine, acyatazanavir, nelfenavir, sanilvudine, emtricitabine, polyinosinic-polycytidylic acid, oseltamivir, zanamivir, valganciclovir, peramivir, laninamivir, favipiravir, amantadine, amphotericin B, miconazole, fluconazole, itraconazole, ketoconazole, ketamine, pentobarbital sodium, thiopental, amopentobarbital, hexobarbital, lidocaine, triazolam, zopiclone, zolpidem, eszopiclone, etizolam, clotiazepam, brotizolam, lormetazepam, estazolam, midazolam, nitrazepam, flunitrazepam, diazepam, chlordiazepoxide HCl, alprazolam, lorazepam, ethyl loflazepate, bromazepam, rilmazafone, chloral hydrate, carbamazepine, clonazepam, zonisamide, sodium valproate, phenytoin, phenobarbital, primidone, gabapentin, opium, morphine, ethylmorphine, oxycodone, hydrocodone, codeine, dihydrocodeine, fentanyl, remifentanil, droperidol, levorphanol, methadone, meperidine, pethidine, buprenorphine, butorphanol, tramadol, tapentadol, nalfurafine, pentazocine, nalbuphine hydrochloride, nalorphine, eptazocine, levallorphan, sulpyrine, aspirin, acetaminophen, ergotamine, dihydroergotamine, sumatriptan, eletriptan, zolmitriptan, rizatriptan, naratriptan, almotriptan, frovatriptan, avitriptan, lasmiditan, olcegepant, telcagepant, donepezil, suxamethonium, pancuronium, sildenafil, vardenafil, apomorphine, tadalafil, atropine, scopolamine, homatropine methylbromide, chlorpromazine, digitoxin, levomepromazine, thioridazine, acepromazine, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, progesterone, testosterone, dehydroepiandrosterone, estrogen, estradiol, levonorgestrel, protamine, leucovorin, dimercaprol, deferoxamine, sodium thiosulfate, mifepristone, risperidone, olanzapine, thalidomide, civamide, acyclovir, valacyclovir, famciclovir, penciclovir, lopinavir, ritonavir, saquinavir, vidarabine, idoxuridine, nifedipine, nimodipine, amiodarone, loratadine, tretinoin, carmustin, beraprost sodium, and any combination thereof.

In some instances, the active agent can be a small molecule drug, e.g., having a molecular weight of less than about 1000 grams/mole (g/mol), about 750 g/mol, or about 500 g/mol. In some instances, the active agent can be an anti-migraine drug. In some instances, the active agent can be an ergot alkaloid. In some instances, the active agent can be dihydroergotamine (DHE) or a pharmaceutically acceptable salt thereof, e.g., DHE mesylate. In some instances, the active agent can be indomethacin, midazolam, or phenobarbital. In some instances, the active agent can be indomethacin or a pharmaceutically acceptable salt thereof. In some instances, the active agent can be testosterone or a pharmaceutically acceptable salt thereof.

In some cases, an active agent disclosed herein can be a peptide or a peptide-related compound, wherein the peptide or peptide-related compound can have a molecular weight of about 10,000 Daltons (Da) or less, about 20,000 (Da) or less, about 30,000 (Da) or less, about 40,000 (Da) or less, or about 50,000 Daltons or less. In some instances, the active agent can be selected from the group consisting of insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, FK-506, octreotide, carperitide, pramlintide, lanreotide, eptifibatide, albiglutide, pasireotide, teriparatide, exenatide, liraglutide, emfuvirtide, ziconotide, ecallantide, mifamurtide, nesiritide, peglinesatide, afamelanotide, linaclotide, lixisenatide, teduglutide, bentiromide, cureletide diethylamine, degarelix, ghrelin, atrial natriuretic peptide, a peptide analog thereof, and any combination thereof.

In some instances, an active agent disclosed herein can be selected from the group consisting of a compound having a formula of:

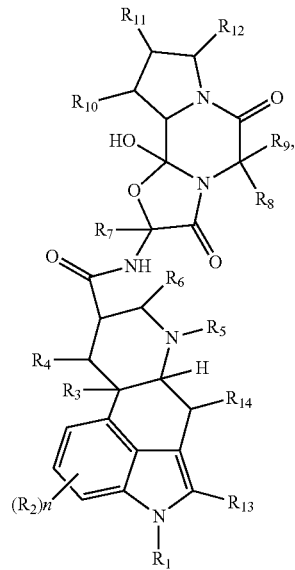

Formula (I)

a stereoisomer thereof, a pharmaceutically acceptable salt thereof, a complex thereof, a chelate thereof, a hydrate thereof, a polymorph thereof, an ion pair thereof, and any combination thereof, and
wherein:

$R_1$ is hydrogen, $(C_1-C_4)$ alkyl, or $(C_1-C_4)$ perfluoroalkyl;

each $R_2$ is independently hydrogen, halogen, alkyl, acyl, heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$, or —$CO_2R_{107}$;

$R_3$ and $R_4$ are independently hydrogen, deuterium, halogen, hydroxy, or methoxy;

$R_5$, $R_6$, and $R_7$ are independently hydrogen, $(C_1-C_3)$ alkyl, or $(C_1-C_3)$ perfluoroalkyl;

$R_8$ and $R_9$ are independently hydrogen, $(C_1-C_4)$ alkyl, or benzyl;

$R_{10}$, $R_{11}$, $R_{12}$, and $R_{14}$ are independently hydrogen, halogen, —OH, $(C_1-C_4)$ alkyl, —$CO_2R_{108}$, or —$CONR_{109}R_{110}$;

$R_{13}$ is hydrogen or halogen;

$R_{101}$-$R_{110}$ are independently hydrogen, halogen, alkyl, acyl, aryl, arylalkyl, heteroalkyl, heteroaryl, or heteroarylalkyl;

k is 0, 1, or 2; and n is 0, 1, 2, or 3.

In some instances, when present, each chiral center can be independently R, S, or racemic. In some instances, said $R_1$ is hydrogen. In some instances, said $R_2$ is hydrogen, or n is 0. In some instances, said $R_3$ and said $R_4$ are both hydrogen. In some instances, said $R_6$ is hydrogen. In some instances, said $R_8$ and said $R_7$ are both methyl. In some instances, said $R_8$ is hydrogen, and said $R_9$ is benzyl. In some instances, $R_{10}$, $R_{11}$, and $R_{12}$ are independently hydrogen or all hydrogen. In some instances, said $R_{13}$ is hydrogen. In some instances, said $R_{14}$ is hydrogen. In some instances, said active agent comprises dihydroergotamine or a pharmaceutically acceptable salt thereof. In some instances, a metabolite is of Formula (I) and wherein said $R_{12}$ is —OH. In some instances, said pharmacologically active metabolite is 8'-hydroxy dihydroergotamine. In some instances, said metabolite is pharmacologically active.

In some instances, a pharmaceutical composition disclosed herein can be a powdery pharmaceutical composition. In some instances, a pharmaceutical composition disclosed herein can be a liquid. In some instances, a pharmaceutical composition disclosed herein can be an aerosol.

In some instances, a pharmaceutical composition disclosed herein comprises: about 0.5 mg to about 10 or about 20 mg (e.g., about 1 mg to about 6 mg) of said active agent, about 12 mg to about 19 mg of microcrystalline cellulose, about 0.1 mg to about 0.6 mg of a thickening agent, and about 6 mg to about 7 mg of a sugar alcohol. In some instances, said thickening agent can be present in a weight amount that can be about: 20%, 15%, 10%, or 5% of that of said active agent. In some instances, said thickening agent comprises hydroxypropyl methylcellulose. In some instances, said thickening agent comprises hydroxypropyl cellulose. In some instances, said thickening agent comprises carboxymethylcellulose. In some instances, said thickening agent can be present in a spray dried particle dispersion. In some instances, said sugar alcohol comprises mannitol. In some instances, said sugar alcohol comprises sorbitol. In some instances, said sugar alcohol comprises galactitol. In some instances, said active agent can be present in a spray-dried particle dispersion. In some instances, about 3 mg to about 13 mg of said microcrystalline cellulose can be present in a spray-dried particle dispersion. In some instances, said microcrystalline cellulose can be at least partially coated with said active agent. In some instances, said active agent can be in an amorphous form. In some instances, said active agent can be dihydroergotamine or a pharmaceutically acceptable salt thereof. In some instances, said pharmaceutical composition comprises said pharmaceutically acceptable salt of dihydroergotamine that can be dihydroergotamine mesylate. In some instances, said dihydroergotamine or said pharmaceutically acceptable salt thereof can be present in about 0.5 or about 1 mg to about 10 or about 20 mg, such as about 3 mg to about 5.5 mg, for example about 3.9 mg to about 4.5 mg, said microcrystalline cellulose can be present in about 15 mg to about 16 mg, said hydroxypropyl methylcellulose can be present in about 0.4 mg to about 0.5 mg, and said mannitol can be present in about 6 mg. In some instances, said dihydroergotamine or said pharmaceutically acceptable salt thereof, said hydroxypropyl methylcellulose, and about 8 mg to about 9 mg of said microcrystalline cellulose are present in a spray-dried particle dispersion. In some instances, said dihydroergotamine or said pharmaceutically acceptable salt thereof can be present in about 0.5 or about 1 mg to about 10 or about 20 mg, such as about 4 mg to about 7 mg, for example about 5.2 mg to about 6 mg, said microcrystalline cellulose can be present in about 18 mg to about 19 mg, said hydroxypropyl methylcellulose can be present in about 0.6 mg, and said mannitol can be present in about 6 mg. In some instances, said dihydroergotamine or said pharmaceutically acceptable salt thereof, said hydroxypropyl methylcellulose, and about 10 mg to about 13 mg of said microcrystalline cellulose are present in a spray-dried particle dispersion.

In some cases, a pharmaceutical composition disclosed herein can comprise one, two, three, or more doses of an active agent (e.g., dihydroergotamine (DHE) or a pharmaceutically acceptable salt thereof) and one or more excipients at independently an amount of at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.3 mg, 1.5 mg, 2 mg, 2.5 mg, 2.6 mg, 3 mg, 3.5 mg, 4 mg, 4.5 mg, 5 mg, 5.2 mg, 5.5 mg, 6 mg, 6.5 mg, 7 mg, 7.5 mg, 8 mg, 8.5 mg, 9 mg, 9.5 mg, or 10 mg, per dose or in total. The composition may comprise a dihydroergotamine or a pharmaceutically acceptable salt thereof and one or more excipients at an amount of about 10-20 mg, about 20-30 mg, about 10-30 mg, about 1-20 mg, about 1-15 mg, about 0.1-20 mg, for example, about 0.1-10 mg, about 0.1-9 mg, about 0.1-8 mg, about 0.1-7 mg, about 0.1-6 mg, about 0.1-5 mg, about 0.1-4 mg, about 0.1-3 mg, about 0.1-2 mg, about 0.1-1 mg, about 0.1-0.8 mg, about 0.1-0.6 mg, about 0.1-0.5 mg, about 0.2-10 mg, about 0.2-9 mg, about 0.2-8 mg, about 0.2-7 mg, about 0.2-6 mg, about 0.2-5 mg, about 0.2-4 mg, about 0.2-3 mg, about 0.2-2 mg, about 0.2-1 mg, about 0.2-0.5 mg, about 0.5-10 mg, about 0.5-9 mg, about 0.5-8 mg, about 0.5-7 mg, about 0.5-6 mg, about 0.5-5 mg, about 0.5-4 mg, about 0.5-3 mg, about 0.5-2 mg, about 0.5-1 mg, about 1-10 mg, about 1-5 mg, about 1-4 mg, about 1-3 mg, about 1-2 mg, about 1.5-6 mg, about 1.3-5.2 mg, about 2-10 mg, about 2-9 mg, about 2-8 mg, about 2-7 mg, about 2-6 mg, about 2-5 mg, about 2-4 mg, about 2-3 mg, about 3-8 mg, about 3-9 mg, about 4-7 mg, about 4-8 mg, about 5-10 mg, about 5-9 mg, about 5-8 mg, about 5-7 mg, about 5-6 mg, about 6-10 mg, about 6-9 mg, about 6-8 mg, about 6-7 mg, about 7-10 mg, about 7-9 mg, about 7-8 mg, about 8-10 mg, about 8-9 mg, about 9-10 mg, about 10-15 mg, about 11-19 mg, about 12-18 mg, about 13-17 mg, about 14-16 mg, about 10-25 mg, about 5-15 mg, about 5-20 mg, or about 5-25 mg, per dose or in total.

In some aspects, provided herein is a pharmaceutical composition that comprises: about 1 mg to about 6 mg of dihydroergotamine or a pharmaceutically acceptable salt thereof, about 12 mg to about 19 mg of microcrystalline cellulose, about 0.1 mg to about 0.6 mg of a thickening agent, and about 6 mg to about 7 mg of a sugar alcohol. In some instances, said pharmaceutical composition can be a powdery pharmaceutical composition. In some instances, said thickening agent can be present in a weight amount that can be about 10% of that of said dihydroergotamine or said pharmaceutically acceptable salt thereof. In some instances, said thickening agent comprises hydroxypropyl methylcellulose. In some instances, said thickening agent comprises hydroxypropyl cellulose. In some instances, said thickening agent comprises carboxymethylcellulose. In some instances, said thickening agent can be present in a spray dried particle dispersion. In some instances, said sugar alcohol comprises mannitol. In some instances, said sugar alcohol comprises sorbitol. In some instances, said sugar alcohol comprises galactitol. In some instances, said dihydroergotamine or said pharmaceutically acceptable salt thereof can be present in a spray-dried particle dispersion. In some instances, about 3 mg to about 13 mg of said microcrystalline cellulose can be present in a spray-dried particle dispersion. In some instances, said microcrystalline cellulose can be at least partially coated with said dihydroergotamine or said pharmaceutically acceptable salt thereof. In some instances, said dihydroergotamine or said pharmaceutically acceptable salt thereof can be in an amorphous form. In some instances, the pharmaceutical composition comprises said pharmaceutically acceptable salt of dihydroergotamine that can be dihydroergotamine mesylate. In some instances, said dihydroergotamine or said pharmaceutically acceptable salt thereof can be present in about 1.3 mg to about 1.5 mg, said microcrystalline cellulose can be present in about 12 mg, said hydroxypropyl methylcellulose can be present in about 0.1 mg to about 0.2 mg, and said mannitol can be present in about 6 mg. In some instances, said dihydroergotamine or said pharmaceutically acceptable salt thereof, said hydroxypropyl methylcellulose, and about 2-4 mg of said microcrystalline cellulose are present in a spray-dried particle dispersion. In some instances, said dihydroergotamine or said pharmaceutically acceptable salt thereof can be present in about 2.6 mg to about 3 mg, said microcrystalline cellulose can be present in about 13 mg, said hydroxypropyl methylcellulose can be present in about 0.3 mg, and said mannitol can be present in about 6 mg. In some instances, said dihydroergotamine or said pharmaceutically acceptable salt thereof, said hydroxypropyl methylcellulose, and about 4 mg to about 7 mg of said microcrystalline cellulose are present in a spray-dried particle dispersion. In some instances, said dihydroergotamine or said pharmaceutically acceptable salt thereof can be present in about 3.9 mg to about 4.5 mg, said microcrystalline cellulose can be present in about 15 mg to about 16 mg, said hydroxypropyl methylcellulose can be present in about 0.4 mg to about 0.5 mg, and said mannitol can be present in about 6 mg. In some instances, said dihydroergotamine or said pharmaceutically acceptable salt thereof, said hydroxypropyl methylcellulose, and about 8 mg to about 9 mg of said microcrystalline cellulose are present in a spray-dried particle dispersion. In some instances, said dihydroergotamine or said pharmaceutically acceptable salt thereof can be present in about 5.2 mg to about 6 mg, said microcrystalline cellulose can be present in about 18 mg to about 19 mg, said hydroxypropyl methylcellulose can be present in about 0.6 mg, and said mannitol can be present in about 6 mg. In some instances, said dihydroergotamine or said pharmaceutically acceptable salt thereof, said hydroxypropyl methylcellulose, and about 10 mg to about 13 mg of said microcrystalline cellulose are present in a spray-dried particle dispersion. In some instances, at least about 80% of said dihydroergotamine or said pharmaceutically acceptable salt thereof can be stable for a storage time period of at least about 60 days to about 3 years in a light-resistant closed container at a room temperature under one atmosphere with a relative humidity of less than about 50% outside said container, as measured by a liquid chromatography method. In some instances, said storage time period can be at least about 1 year.

In some cases, disclosed herein is a pharmaceutical composition that comprises: about 1.5-6 mg of dihydroergotamine (DHE) or a pharmaceutically acceptable salt thereof, about 12-18 mg of microcrystalline cellulose (MCC), about 0.1-0.6 mg of hydroxypropyl methylcellulose (HPMC), and about 6-8 mg of mannitol. In some instances, the DHE or the pharmaceutically acceptable salt thereof can be present in particles, 90% of which have an aerodynamic particle size (APS) larger than 10 microns, for example as measured by Next Generation Impactor or Mercer Cascade Impactor. In some instances, the DHE or the pharmaceutically acceptable salt thereof can be present in particles, 95% of which have an aerodynamic particle size (APS) larger than 5 microns, for example as measured by Next Generation Impactor or Mercer Cascade Impactor. In some instances, the DHE or the pharmaceutically acceptable salt thereof can be in an amorphous form. In some instances, the DHE or the pharmaceutically acceptable salt thereof can be present in a spray-dried dispersion. In some instances, the pharmaceutically acceptable salt of DHE can be DHE mesylate. In some instances, about 2-10 mg of the microcrystalline cellulose (MCC) can be present in a spray-dried dispersion. In some instances, the MCC can be coated with the DHE or the pharmaceutically acceptable salt thereof. In some instances, the HPMC can be present in a spray dried dispersion. In some instances, the spray-dried dispersion takes about 25-40% w/w of the pharmaceutical composition, for example about: 26%, 27%, 28%, 29%, 30%, 31%, 32%, 33%, 34%, 35%, 36%, 37%, 38%, or 39%. In some instances, the spray-dried dispersion takes about 45-60% w/w of the pharmaceutical composition, for example about: 46%, 47%, 48%, 49%, 50%, 51%, 52%, 53%, 54%, 55%, 56%, 57%, 58%, or 59%. In some instances, the HPMC can be present in an amount of about: 20%, 15%, 10%, or 5%, for example about 10% by weight of the DHE or the pharmaceutically acceptable salt thereof. In some instances, the pharmaceutical composition comprises: about 1.5 mg of the dihydroergotamine (DHE) or the pharmaceutically acceptable salt (e.g., about 1.3 mg DHE or about 1.5 mg DHE mesylate), about 12 mg of the microcrystalline cellulose (MCC), about 0.15 mg of the hydroxypropyl methylcellulose (HPMC), and about 6 mg of the mannitol. In some instances, the DHE or the pharmaceutically acceptable salt, the HPMC, and about 2.5 mg of the MCC are present in a spray-dried dispersion. In some instances, the pharmaceutical composition comprises: about 3 mg of the dihydroergotamine (DHE) or the pharmaceutically acceptable salt (e.g., about 2.6 mg DHE or about 3 mg DHE mesylate), about 13 mg of the microcrystalline cellulose (MCC), about 0.3 mg of the hydroxypropyl methylcellulose (HPMC), and about 6 mg of the mannitol. In some instances, the DHE or the pharmaceutically acceptable salt, the HPMC, and about 5 mg of the MCC are present in a spray-dried dispersion. In some instances, the pharmaceutical composition comprises: about 6 mg of the dihydroergotamine (DHE) or the pharmaceutically acceptable salt (e.g., about 5.2 mg DHE or about 6 mg DHE mesylate), about 17.5 mg of the microcrystalline cellulose (MCC), about 0.6 mg of the hydroxypropyl methylcellulose (HPMC), and about 6 mg of the mannitol. In some instances, the DHE or the pharmaceutically acceptable salt, the HPMC, and about 10 mg of the MCC are present in a spray-dried dispersion. In some instances, the pharmaceutical composition can be delivered with a device disclosed herein, for example any illustrated in FIG. 1A, 1B, 2A, 2B or 2C. In some cases, greater than about 90%-95% of the target amount can be delivered even when lowering the actuation velocity, for example to 50% of the optimal value. In-vitro delivery characterization with a device herein demonstrated an average delivered dose of about 90% to about 100% (for example about: 91%, 92%, 93%, 94%, 95%, 96%, 97%, 98%, or 99%) with a relative standard deviation of about 0.1% to about 7% (for example about: 0.5%, 1%, 1.5%, 2%, 2.5%, 3%, 3.5%, 4%, 4.5%, 5%, 5.5%, 6%, or 6.5%).

Methods and compositions presented herein can utilize an active agent in a freebase, salt, hydrate, polymorph, isomer, diastereomer, prodrug, metabolite, ion pair complex, or chelate form. An active agent can be formed using a pharmaceutically acceptable non-toxic acid or base, including an inorganic acid or base, or an organic acid or base. In some instances, an active agent utilized in connection with the methods and compositions presented herein can be a pharmaceutically acceptable salt derived from acids including, but not limited to, the following: acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. In some instances, the active agent can be a salt of methanesulfonic acid. An alternative nomenclature of the methanesulfonic acid salt of DHE can be DHE mesylate.

In some cases, an average particle size of an active agent or a composition disclosed herein can be about 10 to about 100 micrometer ($\mu m$), for example, about: 95 $\mu m$, 90 $\mu m$, 85 $\mu m$, 80 $\mu m$, 75 $\mu m$, 70 $\mu m$, 65 $\mu m$, 60 $\mu m$, 55 $\mu m$, 50 $\mu m$, 45 $\mu m$, 40 $\mu m$, 35 $\mu m$, 30 $\mu m$, 25 $\mu m$, 20 $\mu m$, 15 $\mu m$, 10 $\mu m$, 5 $\mu m$ or less. In some instances, an average particle size of an active agent or a composition disclosed herein can be larger than 10 $\mu m$, for example, more than about: 250 $\mu m$, 200 $\mu m$, 190 $\mu m$, 180 $\mu m$, 170 $\mu m$, 160 $\mu m$, 150 $\mu m$, 140 $\mu m$, 130 $\mu m$, 120 $\mu m$, 110 $\mu m$, 100 $\mu m$, 95 $\mu m$, 90 $\mu m$, 85 $\mu m$, 80 $\mu m$, 75 $\mu m$, 70 $\mu m$, 65 $\mu m$, 60 $\mu m$, 55 $\mu m$, 50 $\mu m$, 45 $\mu m$, 40 $\mu m$, 35 $\mu m$, 30 $\mu m$, 25 $\mu m$, 20 $\mu m$, or 15 $\mu m$. In some instances, the particle size of an active agent or a composition can be about: 20-100 $\mu m$, 25-150 $\mu m$, 25-175 $\mu m$, 25-200 $\mu m$, 25-250 $\mu m$, 25-300 $\mu m$, 50-150 $\mu m$, 50-175 $\mu m$, 50-200 $\mu m$, 50-250 $\mu m$, 50-300 $\mu m$, 10-100 $\mu m$, for example, about: 15-90 $\mu m$, 15-80 $\mu m$, 15-70 $\mu m$, 15-60 $\mu m$, 15-50 $\mu m$, 15-40 $\mu m$, 15-30 $\mu m$, 15-20 $\mu m$, 15-20 $\mu m$, 10-90 $\mu m$, 10-80 $\mu m$, 10-70 $\mu m$, 10-60 $\mu m$, 10-50 $\mu m$, 10-40 $\mu m$, 10-30 $\mu m$, 10-20 $\mu m$, 20-90 $\mu m$, 20-80 $\mu m$, 20-70 $\mu m$, 20-60 $\mu m$, 20-50 $\mu m$, 20-40 $\mu m$, 20-30 $\mu m$, 30-90 $\mu m$, 30-80 $\mu m$, 30-70 $\mu m$, 30-60 $\mu m$, 30-50 $\mu m$, 30-40 $\mu m$, 40-90 $\mu m$, 40-80 $\mu m$, 40-70 $\mu m$, 40-60 $\mu m$, 40-50 $\mu m$, 50-90 $\mu m$, 50-80 $\mu m$, 50-70 $\mu m$, 50-60 $\mu m$, 60-90 $\mu m$, 60-80 $\mu m$, 60-70 $\mu m$, 70-90 $\mu m$, 70-80 $\mu m$, or 80-90 $\mu m$. In some instances the average particle size of the active agent or the composition can be about: 5.0 $\mu m$, 5.5 $\mu m$, 6.0 $\mu m$, 6.5 $\mu m$, 7.0 $\mu m$, 7.5 $\mu m$, 8.0 $\mu m$, 8.5 $\mu m$, 9.0 $\mu m$, 9.5 $\mu m$, 10 $\mu m$, 11 $\mu m$, 12 $\mu m$, 13 $\mu m$, 14 $\mu m$, 15 $\mu m$, 16 $\mu m$, 17 $\mu m$, 18 $\mu m$, 19 $\mu m$, 20 $\mu m$, 25 $\mu m$, 30 $\mu m$, 35 $\mu m$, 40 $\mu m$, 45 $\mu m$, 50 $\mu m$, 55 $\mu m$, 60 $\mu m$, 65 $\mu m$, 70 $\mu m$, 75 $\mu m$, 80 $\mu m$, 85 $\mu m$, 90 $\mu m$, 95 $\mu m$, or 100 $\mu m$. In some instances, not less than 90% of the compositions presented herein have a particle diameter less than 150 $\mu m$, and not more than 5% of the particles have a diameter less than 5 $\mu m$. In some instances, the overall average particle size of the compositions presented herein are about 15 $\mu m$ to about 30 $\mu m$, about 18 $\mu m$ to about 25 lam, about 18 $\mu m$ to about 20 $\mu m$, or about 20 $\mu m$ to about 23 $\mu m$. In some instances, aerodynamic particle size (APS) of the powder compositions can be large enough for minimal potential lung deposition, for example less than 10% of DHE particles in APS <10 $\mu m$, less than 5% of DHE particles in APS <5 $\mu m$, for example as measured by Next Generation Impactor or Mercer Cascade Impactor.

In some cases, a total weight of a composition comprises about 0.4% to about 46%, or about 0.4% to about 23% or about 0.4% to about 9%, or about 2% to about 9%, or about 4% to about 9% of an active agent. In some instances, the total weight of the composition comprises about 0.3% to about 37%, or about 0.3% to about 18% or about 0.3% to about 7%, or about 2% to about 7%, or about 3% to about 9% of an active agent or a pharmaceutically acceptable salt thereof.

In some cases, a composition disclosed herein can further comprise an additional active agent, for example: an adenosine receptor antagonist, a phosphodiesterase inhibitor, an acetylcholinesterase inhibitor, a vasodilator, xanthine, caffeine, paraxanthine, theobromine, and theophylline. In some instances, for example, the methods and compositions further comprise caffeine. In some instances the additional active agent (e. g., caffeine) can be at least about 1% of the total weight of the composition, for example about: 1%, 2%, 3%, 4%, 5%, 6%, 7%, 8%, 9%, 10%, 15%, 20%, 25%, 30%, 35%, 40%, 45%, 50%, 55%, 60% or more of the total weight of the composition. In some instances the additional active agent (e.g., caffeine) can be about 1% to 60% of the total weight of the composition, for example, about: 1%-60%, 1%-50%, 1%-40%, 1%-30%, 1%-20%, 1%-10%, 1%-5%, 10%-60%, 10%-50%, 10%-40%, 10%-30%, 10%-20%, 20%-60%, 20%-50%, 20%-40%, 20%-30%, 30%-60%, 30%-50%, 30%-40%, 40%-60%, 40%-50%, or 50%-60% of the total weight of the composition. In some instances, the composition comprises about 5% to 10% of an additional active agent (e. g., caffeine). In some instances, the caffeine can be anhydrous caffeine. In some instances, the composition comprises about 10% to 15% of an additional active agent (e. g., caffeine).

In some cases, the present disclosure provides for an intranasal pharmaceutical composition comprising particles that comprise an active agent and at least one member selected from the group consisting of a thickening agent, a carrier, a pH adjusting agent, a sugar alcohol, and any combination thereof, wherein: at least about 10%, about 20%, about 30%, about 40%, or about 50% by weight of the active agent in the particles can be amorphous as determined by X-ray diffraction; or when the intranasal pharmaceutical composition can be administered, a pharmacokinetic parameter of the active agent improves by at least about 15%, compared to a corresponding composition that comprises the active agent in a crystalline form when administered. In some instances, the pharmaceutical composition further comprises particles that comprise the active agent and are free from the thickening agent, the carrier, the pH adjuster, the sugar alcohol, or a combination thereof. In some instances, the active agent can be a non-peptide/non-protein drug. In some instances, the particles have an average particle size of from about 15 to about 100 µm, as measured by laser diffraction. In some instances, the particles have an average particle size of from about 20 to about 50 µm, as measured by laser diffraction. In some instances, the particles are spray dried. In some instances, the active agent can be spray dried onto the carrier, the thickening agent, the pH adjuster, the sugar alcohol or a combination thereof to form the particles. In some instances, the solubility can be measured at a pH of about 6.0, 6.1, 6.2, 6.3, 6.4, 6.5, 6.6, 6.7, 6.8, 6.9, 7.0, 7.1, 7.2, 7.3, 7.4, 7.5, 7.8, 7.9, 7.10, for example, ranging from about 6.8 to about 7.4. In some instances, the particles comprise the carrier that can be at least partially water insoluble at 37±0.5° C. In some instances, the water insolubility can be measured at a pH ranging from about 6.8 to about 7.4. In some instances, the particles further comprise the thickening agent, and wherein the carrier can have lower water solubility than that of the thickening agent. In some instances, the particles comprise the carrier that can be at least partially adhesive to mucus. In some instances, the particles comprise the carrier that comprises an oligosaccharide, a polysaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, 13 cyclodextrin, or any combination thereof. In some instances, the particles comprise the carrier that can have an average particle size of from about 10 to about 100 µm, as measured by laser diffraction. In some instances, the carrier can have an average particle size of about 20 µm, as measured by laser diffraction. In some instances, the particles comprise the thickening agent that can be at least partially water soluble at 37±0.5° C. In some instances, the water solubility can be measured at a pH ranging from about 6.8 to about 7.4. In some instances, the particles further comprise the carrier, and wherein the thickening agent can have higher water solubility than that of the carrier. In some instances, the particles comprise that the thickening agent binds to the active agent. In some instances, the particles further comprise the carrier, and wherein the thickening agent binds to the active agent and the carrier. In some instances, the particles comprise the thickening agent that comprises a polysaccharide. In some instances, the thickening agent comprises hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 µm, or about 15-200 microns, as measured by laser diffraction. In some instances, the particles have an average particle size of about 15 µm, or about 50-150 microns, as measured by laser diffraction. In some instances, the particles comprise the thickening agent and the carrier and have an average particle size of from about 10 to about 50 µm, as measured by laser diffraction. In some instances, the particles have an average particle size of about 20 or about 23 µm, as measured by laser diffraction. In some instances, the pharmaceutical composition further comprises a fluidizing agent. In some instances, the fluidizing agent comprises a tribasic calcium phosphate. In some instances, the administration of the pharmaceutical composition improves the pharmacokinetic parameter of the active agent by at least about: 20%, 25%, 30%, 40%, 45%, 50%, 60%, 70%, 80%, 90%, 100%, 150%, 200%, 250%, 300%, 400%, or 500%, when compared to administration of the corresponding composition that comprises the active agent in the crystalline form. In some instances, the improved pharmacokinetic parameter comprises a greater relative bioavailability from 0 min to 15 min ($rBA_{0-15min}$), a greater relative bioavailability from 0 min to 30 min ($rBA_{0-30min}$), a greater relative bioavailability from 0 min to 60 min ($rBA_{0-60min}$), or any combination thereof. In some instances, the improved pharmacokinetic parameter comprises an average $rBA_{0-15min}$, and the improvement can be at least about 100%, e.g., at least about: 115% or 150%. In some instances, the average $rBA_{0-15min}$ can be about 150% to 1500% in serum of the subject. In some instances, the improved pharmacokinetic parameter comprises an average $rBA_{0-30min}$, and the improvement can be at least about 80%, e.g., at least about 115%. In some instances, the improvement can be about 400%. In some instances, the improved pharmacokinetic parameter comprises an average $rBA_{0-60min}$, and the improvement can be at least 100%, e.g., at least about 115%. In some instances, the improvement can be about 200%. In some instances, the improved pharmacokinetic parameter comprises a higher maximum blood concentration ($C_{max}$). In some instances, the improved pharmacokinetic parameter comprises a shorter time to reach maximum blood concentration ($T_{max}$). In some instances, the improved pharmacokinetic parameter comprises an increased area under the curve (AUC) for blood concentration-time profile. In some instances, the pharmaceutical composition further comprises an additional active agent. In some instances, the additional active agent comprises caffeine, which can be amorphous, crystalline, at least 20% of amorphous by weight of the caffeine, or any combination thereof. In some instances, at least about: 25%, 30%, 40%, 45%, 50%, 55%, 60%, 65%, 70%, 75%, 80%, 85%, 90%, 95%, or 98% by weight of the active agent can be amorphous. In some instances, the pharmaceutical composition retains at least about: 80%, 85%, 90%, or 95% by weight of the active agent in a closed container after a period of at least about: 30, 60, 120, 180, 360, 720, or 1080 days. In some instances, the container can be kept at about 15° C., about 20° C., about 30° C., about 40° C., about 50° C., about 60° C., or about 70° C., for example about 20° C. to about 40° C. at one atmosphere pressure with a relative humidity of about 50% to about 75%. For example, the relative humidity may be about 40%, about 45%, about 50%, about 55%, about 60%, about 65%, about 70%, about 75%, about 80%, or about 85%. In some instances, the container can be kept at about 25° C. at one atmosphere pressure with a relative humidity of about 50%. In some instances, the crystalline form comprises a polymorph. In some instances, at least about: 80%, 85%, 90%, 95% of said active agent can be stable for a storage time period of at least about (60 days, 3 months, 6 months, 1 year, or 2 years) to about 3 years in a light-resistant closed container at a room temperature under one atmosphere with a relative humidity of less than about 50%-60% outside said container, as measured by a liquid chromatography method. In some instances, said storage time period can be at least about 1 year.

In some cases, an active agent can be present in an amount of about: 2-4%, 1-5%, 1-10%, 1-15%, 1-20%, 1-25%, 1-30%, 1-40%, 10-50%, 10-40%, 10-30%, or 15-25%, by weight based on a weight of the particles or a pharmaceutical composition, for example about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50%.

In some cases, particle size for each active agent, excipient and powder preparation are determined under a dry powder dispersion condition by a laser diffraction system (Mastersizer 2000, Malvern Instruments Ltd.).

In some cases, presented herein is a composition comprising one or more of an active agent (e.g., DHE, indomethacin, testosterone); a microcrystalline cellulose component (e.g., CEOLUS PH-F20JP, about 20-23 microns in particle size, or a mixture of CEOLUS PH-F20JP and CEOLUS PH-301); a thickening agent (e.g., HPMC); d) a sugar alcohol (e.g., mannitol, about 53-300 microns in particle size); optionally a pH adjuster (e.g., ascorbic acid), optionally a fluidizing agent (e.g., tribasic calcium phosphate); and, optionally an additional active agent disclosed herein, e.g. caffeine, for example, anhydrous caffeine. Examples of a powder composition disclosed herein are presented in Table 1.

In some instances, a composition can be prepared by fluid bed granulation of all its components. In some instances, a pharmaceutical composition comprises an active agent, a thickening agent, a carrier, and a sugar alcohol. In some instances, an active agent can be amorphous, e.g., at least 20% amorphous. In some instances, an active agent can be spray dried, e.g., with a thickening agent. In some instances, a thickening agent can be a binder of low viscosity grade, e.g., HPMC. In some instances, a sugar alcohol can be mannitol. In some instances, a sugar alcohol can have a particle size diameter of about 53 to about 300 microns. In some instances, all components are aggregated together enough to withstand delivery from a device and ensure deposition in a same location. In some instances, an aggregation can be loose enough for immediate break-up to individual components upon deposition on mucosa. In some instances, a particle size diameter of a composition can be about 50 microns to about 150 microns, e.g., about 150 microns. In some instances, the composition can have an angle of repose less than 55°, e.g., less than: 50°, 45°, 40°, 35°, 30°, or 25°. In some instances, a composition can be free from a fluidizing agent. In some instances, a composition disclosed herein can have an angle of repose of about 53° or less, for example, about: 53°, 52°, 51°, 50°, 48°, 46°, 44°, 42°, 40°, 38°, 36°, 34°, 32°, 30°, 28°, 26°, 24°, 22°, 20° or less.

Pharmacokinetics

In some cases, a method disclosed herein can produce in a human subject a time to reach a peak plasma concentration ($T_{max}$) of 90 minutes or longer for a metabolite of an active agent herein, as determined from measurement of a human plasma concentration of said metabolite, for example by liquid chromatography-tandem mass spectrometry with automated extraction. In some instances, said metabolite is pharmacologically active. In some instances, said $T_{max}$ can be at least about 2 hours. In some instances, a peak plasma concentration ($C_{max}$) of said metabolite can be less than about 500 pg/ml. In some instances, said $C_{max}$ of said metabolite can be less than about 250 pg/ml. In some instances, said active agent comprises dihydroergotamine or a pharmaceutically acceptable salt thereof. In some instances, said metabolite can be 8'-hydroxy dihydroergotamine.

In some cases, a method disclosed herein produces in a human subject: a $C_{max}$ of about 1 to about 2.5 ng/ml or a plasma concentration of at least 1 ng/mL at about 10 minutes or shorter, a $T_{max}$ less than 30 mins, and an AUC value selected from the group consisting of an $AUC_{0-30min}$ of about 500 to about 1000 h*pg/ml, an $AUC_{0-60min}$ of about 1000 to about 2000 h*pg/ml, an $AUC_{0-120min}$ of about 2000 to about 3000 h*pg/ml, and an $AUC_{0-inf}$ of about 10000 to about 12000 h*pg/ml, as determined from measurement of a human plasma concentration of an active agent herein, for example by liquid chromatography-tandem mass spectrometry with automated extraction. In some instances, the method further provides a half-life of said active agent from about 12 hours to about 13 hours. In some instances, said active agent comprises dihydroergotamine or a pharmaceutically acceptable salt thereof. In some cases, a method disclosed herein produces in a human subject an apparent clearance (CL/F) value of an active agent from about 50 L/hr to about 1500 L/hr, for example about 100 L/hr to about 1000 L/hr following said administration to said human subject. In some instances, said CL/F value of said active agent can be about 500 to about 600 L/hr, about 400 to about 700 L/hr, about 300 to about 800 L/hr, or about 200 to about 900 L/hr. In some instances, said CL/F value of said active agent can be about 540 L/hr. In some instances, said active agent comprises dihydroergotamine or a pharmaceutically acceptable salt thereof.

In some cases, a method disclosed herein can produce in a human subject a Visual Analog Scale score (for measuring a nasal symptom) less than about: 65, 50, 40, 30, or 20, when measured within 24 hours following said administration to said human subject, wherein said Visual Analog Scale score can be measured in a scale of 0 (none) to 100 (worst imaginable) based on each of the following nasal symptoms: nasal discomfort, nasal burning, nasal itching, nasal pain, nasal blockage or obstruction, abnormal or altered taste, runny nose, and sneezing. In some instances, said Visual Analog Scale score can be measured at about 4 hours following said administration. In some instances, said Visual Analog Scale score can be measured at about 1 hour following said administration. In some instances, said Visual Analog Scale score can be measured at about 15 minutes following said administration. In some instances, said Visual Analog Scale score can be measured at about 5 minutes following said administration. In some instances, said Visual Analog Scale score can be less than about 10. In some instances, said Visual Analog Scale score can be less than about 5. In some instances, said active agent comprises dihydroergotamine or a pharmaceutically acceptable salt thereof.

In some instances, said administration provides at least about a 10 percent higher dC/dT value compared to a dihydroergotamine liquid dosage form in a time period of $T_{0min}$ to $T_{15min}$. In some instances, said administration provides a dC/dT value of at least about 1000 (pg/mL)/hr in a time period of $T_{0min}$ to $T_{15min}$.

In some cases, a method of treatment or prevention disclosed herein can comprise administering to a human subject a powdery composition comprising an active agent, and produces a lower $C_{max}$ and/or AUC value of a metabolite of said active agent than that of a liquid formulation administered by a same route, as determined from measurement of a human plasma concentration of said metabolite, for example by liquid chromatography-tandem mass spectrometry with automated extraction. In some instances, said same route for administration can be an intranasal route. In some instances, the $C_{max}$ and/or AUC value of said metabolite can be about 10-50% (e.g., about: 10-20%, 10-30%, 20-30%, or 20-40%) of that from a liquid formulation administered by a same route. In some other cases, a method of treatment or prevention disclosed herein can comprise administering to a human subject a powdery composition comprising an active agent, and produces a higher $C_{max}$ and/or AUC value of a metabolite (e.g., pharmacologically active) of said active agent than that of a liquid formulation administered by a same route, as determined from measurement of a human plasma concentration of said metabolite, for example by liquid chromatography-tandem mass spectrometry with automated extraction. In some instances, said same route for administration can be an intranasal route. In some instances, the $C_{max}$ and/or AUC value of said metabolite can be about 1.5 to about 5 times (e.g., about: 2, 3, or 4 times) of that from a liquid formulation administered by a same route. In some instances, the AUC value can be $AUC_{0-30min}$, $AUC_{0-60min}$, $AUC_{0-90min}$, $AUC_{0-2h}$, $AUC_{0-3h}$, $AUC_{0-4h}$, $AUC_{0-24h}$, $AUC_{0-48h}$, $AUC_{0-30min}$, or any combination thereof. In some instances, said active agent comprises dihydroergotamine, and said metabolite comprises or can be 8'-hydroxy dihydroergotamine. In some instances, when said method produces 8'-hydroxy dihydroergotamine as one of multiple metabolites, a ratio of a human plasma concentration of 8'-hydroxy dihydroergotamine to that of one or more other metabolites of dihydroergotamine can be higher than that from a liquid formulation administered in a same route. In some instances, said liquid formulation has the same dose of an active agent as a composition disclosed herein. In some other instances, said liquid formulation has comparable pharmacokinetic values (e.g., same or substantially similar) of an active agent with a composition herein that comprises a different dose (e.g., 4.5 or 6 mg of the same active agent, or about 2-4 times strength of that in a liquid composition).

In some cases, a method of treatment or prevention disclosed herein can comprise intranasally administering to a human subject a powdery composition comprising an active agent, and produces a lower $C_{max}$ of a metabolite of said active agent than that of a g liquid formulation administered by a different route (e.g., intramuscularly, subcutaneously, intravenously), as determined from measurement of a human plasma concentration of said metabolite, for example by liquid chromatography-tandem mass spectrometry with automated extraction. In some instances, the $C_{max}$ and/or AUC value of said metabolite can be 10-50% (e.g., about: 10-20%, 10-30%, 20-30%, or 20-40%) of that from a liquid formulation administered by a different route. In some other cases, a method of treatment or prevention disclosed herein can comprise intranasally administering to a human subject a powdery composition comprising an active agent, and produces a higher $C_{max}$ of a metabolite (e.g., pharmacologically active) of said active agent than that of a liquid formulation administered by a different route (e.g., intramuscularly, subcutaneously, intravenously), as determined from measurement of a human plasma concentration of said metabolite, for example by liquid chromatography-tandem mass spectrometry with automated extraction. In some instances, the $C_{max}$ and/or AUC value of said metabolite can be about 1.5 to about 5 times (e.g., about: 2, 3, or 4 times) of that from a liquid formulation administered by a different route. In some instances, the AUC value can be $AUC_{0-30min}$, $AUC_{0-60min}$, $AUC_{0-90min}$, $AUC_{0-2h}$, $AUC_{0-3h}$, $AUC_{0-4h}$, $AUC_{0-24h}$, $AUC_{0-48h}$, $AUC_{0-inf}$, or any combination thereof. In some instances, said active agent comprises dihydroergotamine, and said metabolite can be or comprises 8'-hydroxy dihydroergotamine. In some instances, when said method produces 8'-hydroxy dihydroergotamine as one of multiple metabolites, a ratio of a human plasma concentration of 8'-hydroxy dihydroergotamine to that of one or more other metabolites of dihydroergotamine can be higher than that from a liquid formulation administered intranasally. In some instances, said liquid formulation has the same dose of an active agent as a composition disclosed herein. In some other instances, said liquid formulation has comparable pharmacokinetic values (e.g., same or substantially similar) of an active agent with a composition herein that comprises a different dose (e.g., about 4.5 or 6 mg of the same active agent, or about 2-4 times strength of that in a liquid composition).

In some instances, a peak plasma concentration ($C_{max}$) of said metabolite can be less than about 250 pg/ml, for example less than about: 200, 150, 100, 50, or 10 pg/ml. In some instances, a peak plasma concentration ($C_{max}$) of said metabolite can be less than about 20%, for example less than about: 15%, 10%, 5%, or 1%, of a $C_{max}$ of said active agent measured following said administration to said human subject. In some instances, a plasma concentration of said metabolite can be less than about 5% of a plasma concentration of said active agent measured within about: 30, 25, 20, 15, 10, or 5 minutes following said administration to said human subject. In some instances, a plasma concentration of said metabolite can be less than about 2% of a plasma concentration of said active agent measured within about: 15, 10, or 5 minutes following said administration to said human subject.

In some instances, a reduced presence of said metabolite can result in a reduced pharmacological effect from said metabolite in said human subject. In some instances, said reduced pharmacological effect is less than 20% binding activity at an adrenergic receptor (e.g., α1[non-specific], α2A, α2B, α2C, β), dopaminergic receptor (e.g., D: $D_1$, $D_2$, $D_3$), or serotonergic receptor (e.g., 5-HT receptor or subtypes: $5\text{-}HT_{1A}$, $5\text{-}HT_{1B}$, $5\text{-}HT_{1D}$, $5\text{-}HT_{2A}$, $5\text{-}HT_{2C}$, $5\text{-}HT_3$, $5\text{-}HT_4$, $5\text{-}HT_{5A}$, $5\text{-}HT_6$, $5\text{-}HT_7$) as measured by a radioligand competitive binding assay. In some instances, said reduced pharmacological effect in said human subject is less than that in a non-human animal. In some instances, said reduced pharmacological effect in said human subject is manifested by: a reduced transcutaneous partial $O_2$ pressure as measured at the back of a foot, a reduced venous constrictive effect as determined using a venous occlusion mercury strain gauge, a less decreased diameter or compliance of a brachial artery wall, a decreased constrictive effect on a human coronary artery, meningeal artery, or saphenous vein, a less decreased venous diameter at a fixed occlusion pressure, a change in peripheral circulatory capacitance, or any combination thereof.

In some instances, the methods and compositions herein can comprise a mean $T_{max}$ of an active agent after administration of the composition of at least about 1 minutes, for example, at least about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 25 minutes, 30 minutes, 35 minutes, 40 minutes, 45 minutes, 50 minutes, 60 minutes, 90 minutes, or 120 minutes. In some instances the mean $T_{max}$ of an active agent after administration of the composition can be about 1 to about 120 minutes, for example, about 1-120 minutes, about 1-90 minutes, about 1-60 minutes, about 1-50 minutes, 1-40 minutes, 1-30 minutes, 1-20 minutes, 1-10 minutes, 1-5 minutes, about 1-2 minutes, about 5-120 minutes, about 5-90 minutes, about 5-60 minutes, about 5-50 minutes, 5-40 minutes, 5-30 minutes, 5-25 minutes, 5-20 minutes, 5-10 minutes, about 10-120 minutes, about 10-90 minutes, about 10-60 minutes, about 10-50 minutes, 10-40 minutes, 10-30 minutes, 10-20 minutes, about 20-120 minutes, about 20-90 minutes, about 20-60 minutes, about 20-50 minutes, 20-40 minutes, 20-30 minutes, about 30-120 minutes, about 30-90 minutes, about 30-60 minutes, about 30-50 minutes, 30-40 minutes, about 40-120 minutes, about 40-90 minutes, about 40-60 minutes, 40-50 minutes, about 50-120 minutes, about 50-90 minutes, about 50-60 minutes, about 60-120 minutes, about 60-90 minutes, or about 90-120 minutes. In some instances, the mean $T_{max}$ after administration of the composition can be measured from a primate, for example a monkey such as a Cynomolgus monkey. In some instances, the mean $T_{max}$ after administration of the composition can be measured from a human subject.

In some instances, the methods and compositions herein can comprise a mean $C_{max}$ of an active agent after administration of the composition of at least about 0.01 nanogram/milliliter (ng/mL), for example, at least about 0.01 ng/mL, 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1 ng/mL, 1.5 ng/mL, 2 ng/mL, 2.5 ng/mL, 3 ng/mL, 3.5 ng/mL, 4 ng/mL, 4.5 ng/mL, 5 ng/mL, 5.5 ng/mL, 6 ng/mL, 6.5 ng/mL, 7 ng/mL, 7.5 ng/mL, 8 ng/mL, 8.5 ng/mL, 9 ng/mL, 9.5 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 110 ng/mL, 120 ng/mL, 130 ng/mL, 140 ng/mL, or 150 ng/mL. In some instances the mean $C_{max}$ of an active agent after administration of the composition can be about 0.1 to about 150 ng/mL, for example, about 0.1-150 ng/mL, 0.1-130 ng/mL, 0.1-110 ng/mL, 0.1-90 ng/mL, 0.1-70 ng/mL, 0.1-50 ng/mL, 0.1-30 ng/mL, 0.1-10 ng/mL, 0.1-5 ng/mL, 0.1-1.0 ng/mL, 0.1-0.5 ng/mL, 1-150 ng/mL, 1-130 ng/mL, 1-110 ng/mL, 1-90 ng/mL, 1-70 ng/mL, 1-50 ng/mL, 1-30 ng/mL, 1-10 ng/mL, 1-5 ng/mL, 5-150 ng/mL, 5-130 ng/mL, 5-110 ng/mL, 5-90 ng/mL, 5-70 ng/mL, 5-50 ng/mL, 5-30 ng/mL, 5-10 ng/mL, 10-150 ng/mL, 10-130 ng/mL, 10-110 ng/mL, 10-90 ng/mL, 10-70 ng/mL, 10-50 ng/mL, 10-30 ng/mL, 30-150 ng/mL, 30-130 ng/mL, 30-110 ng/mL, 30-90 ng/mL, 30-70 ng/mL, 30-50 ng/mL, 50-150 ng/mL, 50-130 ng/mL, 50-110 ng/mL, 50-90 ng/mL, 50-70 ng/mL, 70-150 ng/mL, 70-130 ng/mL, 70-110 ng/mL, 70-90 ng/mL, 90-150 ng/mL, 90-130 ng/mL, 90-110 ng/mL, 110-150 ng/mL, 110-130 ng/mL, or 130-150 ng/mL. In some instances, the mean $C_{max}$ after administration of the composition can be measured from a primate, for example a monkey such as a Cynomolgus monkey. In some instances, the mean $C_{max}$ after administration of the composition can be measured from a human subject.

In some instances, the methods and compositions herein can comprise a mean $AUC_{0-inf}$ of an active agent after administration of the composition of at least about 0.5 nanogram·hour/milliliter (ng·h/mL), for example, at least about 0.5 ng·h/mL, 1 ng·h/mL, 2 ng·h/mL, 3 ng·h/mL, 4 ng·h/mL, 5 ng·h/mL, 6 ng·h/mL, 7 ng·h/mL, 8 ng·h/mL, 9 ng·h/mL, 10 ng·h/mL, 20 ng·h/mL, 30 ng·h/mL, 40 ng·h/mL, 50 ng·h/mL, 60 ng·h/mL, 70 ng·h/mL, 80 ng·h/mL, 90 ng·h/mL, 100 ng·h/mL, 200 ng·h/mL, 300 ng·h/mL, 400 ng·h/mL, 500 ng·h/mL, 600 ng·h/mL, or 700 ng·h/mL. In some instances the mean $AUC_{0-inf}$ of an active agent after administration of the composition can be about 0.5 to about 700 ng·h/mL, for example, about 0.5-700 ng·h/mL, 0.5-500 ng·h/mL, 0.5-300 ng·h/mL, 0.5-100 ng·h/mL, 0.5-80 ng·h/mL, 0.5-60 ng·h/mL, 0.5-40 ng·h/mL, 0.5-20 ng·h/mL, 0.5-10 ng·h/mL, 0.5-5 ng·h/mL, 0.5-2 ng·h/mL, 0.5-1 ng·h/mL, 1-700 ng·h/mL, 1-500 ng·h/mL, 1-300 ng·h/mL, 1-100 ng·h/mL, 1-80 ng·h/mL, 1-60 ng·h/mL, 1-40 ng·h/mL, 1-20 ng·h/mL, 1-10 ng·h/mL, 1-5 ng·h/mL, 10-700 ng·h/mL, 10-500 ng·h/mL, 10-300 ng·h/mL, 10-100 ng·h/mL, 10-80 ng·h/mL, 10-60 ng·h/mL, 10-40 ng·h/mL, 10-20 ng·h/mL, 20-700 ng·h/mL, 20-500 ng·h/mL, 20-300 ng·h/mL, 20-100 ng·h/mL, 20-80 ng·h/mL, 20-60 ng·h/mL, 20-40 ng·h/mL, 40-700 ng·h/mL, 40-500 ng·h/mL, 40-300 ng·h/mL, 40-100 ng·h/mL, 40-80 ng·h/mL, 40-60 ng·h/mL, 60-700 ng·h/mL, 60-500 ng·h/mL, 60-300 ng·h/mL, 60-100 ng·h/mL, 60-80 ng·h/mL, 80-700 ng·h/mL, 80-500 ng·h/mL, 80-300 ng·h/mL, 80-100 ng·h/mL, 100-700 ng·h/mL, 100-500 ng·h/mL, 100-300 ng·h/mL, 300-700 ng·h/mL, 300-500 ng·h/mL, or 500-700 ng·h/mL. In some instances, the mean $AUC_{0-inf}$ after administration of the composition can be measured from a primate, for example a monkey such as a Cynomolgus monkey. In some instances, the mean $AUC_{0-inf}$ after administration of the composition can be measured from a human subject.

In some instances, the methods and compositions herein can comprise a mean $AUC_{0-4}$ of an active agent after administration of the composition of at least about 0.5 ng·h/mL, for example, at least about 0.5 ng·h/mL, 1 ng·h/mL, 2 ng·h/mL, 3 ng·h/mL, 4 ng·h/mL, 5 ng·h/mL, 6 ng·h/mL, 7 ng·h/mL, 8 ng·h/mL, 9 ng·h/mL, 10 ng·h/mL, 20 ng·h/mL, 30 ng·h/mL, 40 ng·h/mL, 50 ng·h/mL, 60 ng·h/mL, 70 ng·h/mL, 80 ng·h/mL, 90 ng·h/mL, 100 ng·h/mL, 200 ng·h/mL, 300 ng·h/mL, 400 ng·h/mL, 500 ng·h/mL, 600 ng·h/mL, or 700 ng·h/mL. In some instances the mean $AUC_{0-inf}$ of an active agent after administration of the composition can be about 0.5 to about 700 ng·h/mL, for example, about 0.5-700 ng·h/mL, 0.5-500 ng·h/mL, 0.5-300 ng·h/mL, 0.5-100 ng·h/mL, 0.5-80 ng·h/mL, 0.5-60 ng·h/mL, 0.5-40 ng·h/mL, 0.5-20 ng·h/mL, 0.5-10 ng·h/mL, 0.5-5 ng·h/mL, 0.5-2 ng·h/mL, 0.5-1 ng·h/mL, 1-700 ng·h/mL, 1-500 ng·h/mL, 1-300 ng·h/mL, 1-100 ng·h/mL, 1-80 ng·h/mL, 1-60 ng·h/mL, 1-40 ng·h/mL, 1-20 ng·h/mL, 1-10 ng·h/mL, 1-5 ng·h/mL, 10-700 ng·h/mL, 10-500 ng·h/mL, 10-300 ng·h/mL, 10-100 ng·h/mL, 10-80 ng·h/mL, 10-60 ng·h/mL, 10-40 ng·h/mL, 10-20 ng·h/mL, 20-700 ng·h/mL, 20-500 ng·h/mL, 20-300 ng·h/mL, 20-100 ng·h/mL, 20-80 ng·h/mL, 20-60 ng·h/mL, 20-40 ng·h/mL, 40-700 ng·h/mL, 40-500 ng·h/mL, 40-300 ng·h/mL, 40-100 ng·h/mL, 40-80 ng·h/mL, 40-60 ng·h/mL, 60-700 ng·h/mL, 60-500 ng·h/mL, 60-300 ng·h/mL, 60-100 ng·h/mL, 60-80 ng·h/mL, 80-700 ng·h/mL, 80-500 ng·h/mL, 80-300 ng·h/mL, 80-100 ng·h/mL, 100-700 ng·h/mL, 100-500 ng·h/mL, 100-300 ng·h/mL, 300-700 ng·h/mL, 300-500 ng·h/mL, or 500-700 ng·h/mL. In some instances, the mean $AUC_{0-inf}$ after administration of the composition can be measured from a primate, for example a monkey such as a Cynomolgus monkey. In some instances, the mean $AUC_{0-inf}$ after administration of the composition can be measured from a human subject. In some instances, the measurement can be taken 5 minutes, 10 minutes, 20 minutes, 30 minutes, 60 minutes, 90 minutes, 120 minutes, 180 minutes, 240 minutes, 300 minutes, 360 minutes, 420 minutes, or 480 minutes, or any combination thereof.

In some instances, the methods and compositions herein can comprise a mean $T_{1/2}$ of an active agent after administration of the composition of at least about 10 minutes, for example, at least about 10 minutes, 20 minutes, 30 minutes, 40 minutes, 50 minutes, 60 minutes, 70 minutes, 80 minutes, 90 minutes, 100 minutes, 120 minutes, 150 minutes, 200 minutes, 250 minutes, or 300 minutes. In some instances the mean $T_{1/2}$ of an active agent after administration of the composition can be about 10 to about 300 minutes, for example, about 10-300 minutes, 10-250 minutes, 10-200 minutes, 10-150 minutes, 10-120 minutes, 10-100 minutes, 10-80 minutes, 10-60 minutes, 10-40 minutes, 10-20 minutes, 20-300 minutes, 20-250 minutes, 20-200 minutes, 20-150 minutes, 20-120 minutes, 20-100 minutes, 20-80 minutes, 20-60 minutes, 20-40 minutes, 40-300 minutes, 40-250 minutes, 40-200 minutes, 40-150 minutes, 40-120 minutes, 40-100 minutes, 40-80 minutes, 40-60 minutes, 60-300 minutes, 60-250 minutes, 60-200 minutes, 60-150 minutes, 60-120 minutes, 60-100 minutes, 60-80 minutes, 80-300 minutes, 80-250 minutes, 80-200 minutes, 80-150 minutes, 80-120 minutes, 80-100 minutes, 100-300 minutes, 100-250 minutes, 100-200 minutes, 100-150 minutes, 100-120 minutes, 120-300 minutes, 120-250 minutes, 120-200 minutes, 120-150 minutes, 150-300 minutes, 150-250 minutes, 150-200 minutes, 200-300 minutes, 200-250 minutes, or 250-300 minutes. In some instances, for example, the mean $T_{1/2}$ of an active agent after administration of the composition can be about 100 to about 300 minutes. In some instances, the mean $T_{1/2}$ after administration of the composition can be measured from a monkey (e.g., Cynomolgus monkeys). In some instances, the mean $T_{1/2}$ after administration of the composition can be measured from a human subject.

In some instances of an active agent, a mean $T_{max}$ may be about 10 to about 30 minutes, the mean $C_{max}$ can be about 0.5 to about 6 ng/mL, the mean $AUC_{0-inf}$ can be about 1 to about 15 ng·h/mL, and the mean $T_{1/2}$ can be about 100 to about 300 minutes. In another case, the mean $T_{max}$ may be about 10 to about 50 minutes, the mean $C_{max}$ can be about 1 to about 15 ng/mL, the mean $AUC_{0-inf}$ can be about 10 to about 50 ng·h/mL, and the mean $T_{1/2}$ can be about 100 to about 300 minutes. In another case of an active agent, the mean $T_{max}$ may be about 10 to about 50 minutes, the mean $C_{max}$ can be about 2 to about 20 ng/mL, the mean $AUC_{0-inf}$ can be about 15 to about 110 ng·h/mL, and the mean $T_{1/2}$ can be about 100 to about 300 minutes. In another case of an active agent, the mean $T_{max}$ may be about 10 to about 50 minutes, the mean $C_{max}$ can be about 2 to about 50 ng/mL, the mean $AUC_{0-inf}$ can be about 15 to about 200 ng·h/mL, and the mean $T_{1/2}$ can be about 100 to about 300 minutes. In some instances, the mean $T_{max}$, $C_{max}$, $AUC_{0-inf}$, and/or $T_{1/2}$ after administration of the composition can be measured from a primate, for example a monkey such as a Cynomolgus monkey. In some instances, the mean $T_{max}$, $C_{max}$, $AUC_{0-inf}$, and/or $T_{1/2}$ after administration of the composition can be measured from a human subject.

In some instances, a method herein acutely treats migraine headache with or without aura and comprises administering to a subject with migraine headache an effective dose of a pharmaceutical composition comprising dihydroergotamine (DHE) or salt thereof, wherein the effective dose can be administered by an intranasal delivery device that provides, following intranasal administration, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml. In some instances, the pharmaceutical composition can be a powder or a liquid.

In some instances, a kit herein acutely can treat migraine headache with or without aura and comprises a vial, within which can be sealed at least one effective dose of a pharmaceutical composition comprising dihydroergotamine (DHE) or salt thereof, wherein the effective dose provides, following intranasal administration by an intranasal delivery device, (a) a mean peak plasma DHE concentration ($C_{max}$) of at least 750 pg/ml, (b) with a mean time to $C_{max}$ ($T_{max}$) of DHE of less than 45 minutes, and (c) a mean plasma $AUC_{0-inf}$ of DHE of at least 2500 pg*hr/ml. In some instances, the pharmaceutical composition can be a powder or a liquid.

In some cases, a composition disclosed herein can be administered such that the intersubject variability in an active agent $C_{max}$ can be less than 50%. In some instances, for example, the intersubject variability in an active agent $C_{max}$ may be less than 50%, 30%, 25%, 20%, 15%, 10%, or 5%. In some cases, the composition can be administered such that the intersubject variability in an active agent $T_{max}$ can be less than 30%. In some instances, for example, the intersubject variability in an active agent $T_{max}$ can be less than 30%, 25%, 20%, 15%, 10%, or 5%. In some cases, the composition can be administered such that the intersubject variability in DHE $AUC_{0-inf}$ may be less than 30%. In some instances, for example, the intersubject variability in an active agent $AUC_{0-inf}$ can be less than 30%, 25%, 20%, 15%, 10%, or 5%. In some cases, the composition can be administered such that the intersubject variability in an active agent $T_{1/2}$ can be less than 30%. In some instances, for example, the intersubject variability in an active agent $T_{1/2}$ may be less than 30%, 25%, 20%, 15%, 10%, or 5%. In some instances, the intersubject variability in an active agent $T_{max}$, $C_{max}$, $AUC_{0-inf}$, and/or $T_{1/2}$ after administration of the composition can be measured from primates, for example a monkey such as a Cynomolgus monkeys. In some instances, the intersubject variability in an active agent $T_{max}$, $C_{max}$, $AUC_{0-inf}$, and/or $T_{1/2}$ after administration of the composition can be measured from human subjects.

In some cases, a pharmacokinetic parameter disclosed herein can be determined with an analysis of a blood sample or plasma sample collected at one or more time points of about: 2, 5, 10, 15, 20, 30, 45, 60, 120, or 180 minutes after intranasal administration. In some instances, the analysis comprises a measurement of a plasma concentration of an active agent for example DHE, or a metabolite for example 8'-hydroxy-DHE, or a combination thereof in the blood sample or plasma sample. In some instances, the analysis can be conducted with liquid chromatography (LC), mass spectrometry (MS), or a combination thereof. In some instances, the analysis can be conducted with a LC/MS/MS method or a liquid chromatography-tandem mass spectrometry with manual or automated extraction.

Excipients

In some cases, a composition disclosed herein can comprise one or more excipients, e.g., different substance, or same substance but different sizes. In some instances, the excipient comprises a carrier, e.g., water-insoluble polysaccharide or oligosaccharide. In some instances, the carrier can be selected from a group consisting of cellulose acetate, cellulose acetate butyrate, cellulose acetate propionate, cellulose acetate phthalate, chitosan, β-cyclodextrin, ethyl cellulose, hydroxypropylmethyl cellulose phthalate (HPMCP), microcrystalline cellulose, starch, and any combination thereof. In some instances, the excipient comprises a thickening agent, e.g., a water-soluble polysaccharide. In some instances, the thickening agent can be selected from the group consisting of hydroxy propyl methyl cellulose (HPMC), acacia, alginic acid, colloidal silicone dioxide, carboxymethylcellulose calcium, gelatin, hydroxy propyl cellulose, hydroxyl propyl cellulose (hypromellose), methyl cellulose, sucrose, sodium alginate, sodium carboxy methyl cellulose, and any combination thereof. In some instances, the excipient comprises a first excipient (any excipient disclosed herein) and a second excipient (any excipient disclosed herein). In some instances, the excipient comprises a carrier (e.g., microcrystalline cellulose) and a thickening agent (e.g., HPMC). In some instances, the composition disclosed herein comprises a sugar alcohol. In some instances, the sugar alcohol can be selected from the group consisting of mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof. In some instances, the sugar alcohol can have 3, 4, 5, 6, 7, 12, 18, or 24 carbons. In some instances, a composition disclosed herein comprises a propellant suitable for pharmaceutical use, for example a hydrofluoroalkane such as hydrofluoroalkane-134a. In some instances, a composition disclosed herein can be free from a propellant, for example does not contain a hydrofluoroalkane.

In some instances, particles can comprise a thickening agent that may be present in an amount of about: 0.1-0.5%, 0.05-1%, 0.05-2%, 0.05-3%, 0.05-4%, 0.05-5%, 4-6%, 3-7%, 2-8%, 1-10%, or 1-20% by weight based on a weight of the active agent or a pharmaceutical composition, for example about: 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, or 20 percent. In some instances, particles comprise microcrystalline cellulose that can be present in an amount of about: 10-95%, 10-75%, 15-55%, 20-75%, 35-75%, or 40-75% by weight based on a weight of the active agent or a pharmaceutical composition, for example about: 10%, 20%, 30%, 40%, 50%, 60%, 70%, 75%, 80%, 85%, 90%, or 95%. In some instances, particles comprise a sugar alcohol that can be present in an amount of about: 10-95%, 10-75%, 15-55%, 20-75%, 35-75%, or 40-75% by weight based on a weight of the active agent or a pharmaceutical composition, for example about: 10%, 20%, 30%, 40%, 50%, 60%, 70%, 75%, 80%, 85%, 90%, or 95%. In some instances, particles comprise the pH adjusting agent that can be present in an amount of about: 10-20%, 20-30%, 5-25%, 15-35%, or 5-40% by weight based on a weight of the active agent or a pharmaceutical composition, for example about: 5%, 6%, 7%, 8%, 9%, 10%, 15%, 20%, 25%, 30%, 35%, or 40%.

In some instances, a particle or composition disclosed herein can comprise a pH adjusting agent. In some instances, the pH adjusting agent can be selected from the group consisting of ascorbic acid, sodium ascorbate, tartaric acid, sodium tartrate, potassium tartrate, calcium tartrate, lithium tartrate, citric acid, sodium citrate, potassium citrate, calcium citrate, lithium citrate, phosphoric acid, sodium dihydrogenphosphate, sodium monohydrogenphosphate, lithium phosphate, potassium phosphate, calcium phosphate, sodium carbonate, sodium hydrogencarbonate, lactic acid, sodium lactate, potassium lactate, calcium lactate, acetic acid, sodium acetate, potassium acetate, calcium acetate, propionic acid, sulphuric acid, sodium sulphate, potassium sulphate, boric acid, sodium borate, maleic acid, lithium maleate, sodium maleate, potassium maleate, calcium maleate, succinic acid, lithium succinate, sodium succinate, potassium succinate, calcium succinate, fumaric acid, glutamic acid, formic acid, malic acid, hydrochloric acid, nitric acid, sodium hydroxide, potassium hydroxide, triethanolamine, diisopropanolamine, ammonia solution, monoethanole amine, diethanoleamine, triethanoleamine meglumine, sodium citrate, sodium bicarbonate, potassium bicarbonate, and any combination thereof. In some instances, a pH adjusting agent disclosed herein can be acetic acid; adipic acid; ammonium aluminum sulphate; ammonium bicarbonate; ammonium carbonate; ammonium citrate, dibasic; ammonium citrate, monobasic; ammonium hydroxide; ammonium phosphate, dibasic; ammonium phosphate, monobasic; calcium acetate; calcium acid pyrophosphate; calcium carbonate; calcium chloride; calcium citrate; calcium fumarate; calcium gluconate; calcium hydroxide; calcium lactate; calcium oxide; calcium phosphate, dibasic; calcium phosphate, monobasic; calcium phosphate, tribasic; calcium sulphate; carbon dioxide; citric acid; cream of tartar; fumaric acid; gluconic acid; glucono-delta-lactone; hydrochloric acid; lactic acid; magnesium carbonate; magnesium citrate; magnesium fumarate; magnesium hydroxide; magnesium oxide; magnesium phosphate; magnesium sulphate; malic acid; manganese sulphate; metatartaric acid; phosphoric acid; potassium acid tartrate; potassium aluminum sulphate; potassium bicarbonate; potassium carbonate; potassium chloride; potassium citrate; potassium fumarate; potassium hydroxide; potassium lactate; potassium phosphate, dibasic; potassium phosphate, tribasic; potassium sulphate; potassium tartrate; potassium tripolyphosphate; sodium acetate; sodium acid pyrophosphate; sodium acid tartrate; sodium aluminum phosphate; sodium aluminum sulphate; sodium bicarbonate; sodium bisulphate; sodium carbonate; sodium citrate; sodium fumarate; sodium gluconate; sodium hexametaphosphate; sodium hydroxide; sodium lactate; sodium phosphate, dibasic; sodium phosphate, monobasic; sodium phosphate, tribasic; sodium potassium hexametaphosphate; sodium potassium tartrate; sodium potassium tripolyphosphate; sodium pyrophosphate, tetrabasic; sodium tripolyphosphate; sulphuric acid; sulphurous acid; tartaric acid; or any combination thereof.

In some instances, a buffering agent can be selected from the group consisting of sodium phosphate, sodium hydrogenphosphate, anhydrous sodium dihydrogenphosphate, crystalline sodium dihydrogenphosphate, disodium hydrogenphosphate, potassium phosphate, potassium dihydrogenphosphate, dipotassium phosphate, boric acid, borax, sodium acetate, citric acid, citric anhydride, sodium citrate, sodium glutamate, creatinine, and phosphate buffered saline.

In some instances, compositions may further comprise a fluidizing agent. For example, the fluidizing agent can be a metal salt (e.g., a calcium salt) or a phosphate salt. In some instances, the fluidizing agent can be a calcium phosphate salt, e.g., tribasic calcium phosphate. In some instances, the tribasic calcium phosphate can be about 0.1% to about 5.0% of the total weight of the composition, for example about: 0.1%-5%, 0.1%-4%, 0.1%-3%, 0.1%-2%, 0.1%-1%, 0.1%-0.5%, 0.5%-5%, 0.5%-4%, 0.5%-3%, 0.5%-2%, 0.5%-1%, 1%-5%, 1%-4%, 1%-3%, 1%-2%, 2%-5%, 2%-4%, 2%-3%, 3%-5%, 3%-4%, or 4%-5% of the total weight of the composition. In some instances, the tribasic calcium phosphate can be about 0.5% to about 1.0% of the total weight of the composition. In some instances, the tribasic calcium phosphate can be about 0.5% to about 1.5% of the total weight of the composition. In some instances, the tribasic calcium phosphate can be about 0.8% of the total weight of the composition. Fluidizing agents include but are not limited to tribasic calcium phosphate, hydrous silicon dioxide, light anhydrous silicic acid, crystalline cellulose, synthetic aluminum silicate, calcium silicate, titanium oxide, stearic acid, calcium stearate, magnesium stearate, talc, cornstarch, magnesium metasilicate aluminate, anhydrous calcium hydrogenphosphate, synthetic hydrotalcite, and magnesium metasilicate aluminate. In some instances, a fluidizing agent can be tribasic calcium phosphate. In some instances, a tribasic calcium phosphate comprises about 0.5-1.0% of a total weight of a composition. In specific instances of a methods of treating migraine, a tribasic calcium phosphate comprises about 0.8% of a total weight of a composition.

In some cases, an excipient can have an average particle size of about 100 μm or less, e.g., about: 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 10 μm, 5

µm or less. In some instances, a composition herein may comprise a first excipient with an average particle diameter size of about 30 µm or less, and a second excipient with an average particle size diameter of about 30 to about 100 µm. In some instances, the first excipient may have an average particle diameter size of about 30 µm or less, for example, about: 30-25 µm, 30-20 µm, 30-15 µm, 30-10 µm, 30-5 µm, 25-20 µm, 25-15 µm, 25-10 µm, 25-5 µm, 20-15 µm, 20-10 µm, 20-5 µm, 15-10 µm, 15-5 µm or 10-5 µm. In some instances, the first excipient can have an average particle diameter size of about 15-30 µm. In some instances, the first excipient can have an average particle diameter size of about 18-20 µm. In some instances, the first excipient can have an average particle diameter size of about 20 µm. In some instances, the second excipient may have an average particle diameter size of about 30 to about 100 µm, for example, about: 30-90 µm, 30-80 µm, 30-70 µm, 30-60 µm, 30-50 µm, 30-40 µm, 40-90 µm, 40-80 µm, 40-70 µm, 40-60 µm, 40-50 µm, 50-90 µm, 50-80 µm, 50-70 µm, 50-60 µm, 60-90 µm, 60-80 µm, 60-70 µm, 70-90 µm, 70-80 µm, or 80-90 µm. In some instances, the second excipient can have an average particle diameter size of about 45-65 µm. In some instances, the second excipient can have an average particle diameter size of about 45-55 µm. In some instances, the second excipient can have an average particle diameter size of about 50-55 µm. In some instances, the second excipient can have an average particle diameter size of about 50 µm. In some instances, the first excipient can have an average particle diameter size of about 15 to about 30 µm and the second excipient can have an average particle diameter size of about 45 to about 65 µm. In some instances, the first excipient can have an average particle size of about 20 µm and the second excipient can have an average particle size diameter of about 50 to about 55 µm. In some instances, the first excipient can have an average particle diameter size of about 20 µm, and the second excipient can have an average particle size diameter of about 50 µm. In some cases, the excipient can be substantially free of particles with an average particle diameter size of about 31 to about 44 µm. In some instances, the excipient can be substantially free of particles with an average particle diameter size of about 31 to about 49 µm. In some cases, substantially free of particles with an average particle diameter size means less than 15%, 10%, 5%, or 2% of all the particles fall into the given range.

In some cases, one or more excipient(s) (e.g., microcrystalline cellulose, HPMC, mannitol, TCP) may comprise at least about 5% of the total weight of the composition, for example, at least about: 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 98% of the total weight of the composition. In some instances, the excipient(s) may comprise about 15% to about 99% of the total weight of the composition, for example, about: 15%-99%, 20%-99%, 30%-99%, 40%-99%, 50%-99%, 60%-99%, 70%-99%, 80%-99%, 90%-99%, 15%-90%, 20%-90%, 30%-90%, 40%-90%, 50%-90%, 60%-90%, 70%-90%, 80%-90%, 15%-80%, 20%-80%, 30%-80%, 40%-80%, 50%-80%, 60%-80%, 70%-80%, 15%-70%, 20%-70%, 30%-70%, 40%-70%, 50%-70%, 60%-70%, 15%-60%, 20%-60%, 30%-60%, 40%-60%, 50%-60%, 15%-50%, 20%-50%, 30%-50%, 40%-50%, 15%-40%, 20%-40%, 30%-40%, 15%-30%, 20%-30%, or 15-20% of the total weight of the composition. In some instances, the first excipient comprises about 10 to about 90% of the total weight of the composition, for example, about: 10%-90%, 15%-90%, 20%-90%, 30%-90%, 40%-90%, 50%-90%, 60%-90%, 70%-90%, 80%-90%, 10%-80%, 15%-80%, 20%-80%, 30%-80%, 40%-80%, 50%-80%, 60%-80%, 70%-80%, 10%-70%, 15%-70%, 20%-70%, 30%-70%, 40%-70%, 50%-70%, 60%-70%, 10%-60%, 15%-60%, 20%-60%, 30%-60%, 40%-60%, 50%-60%, 10%-50%, 15%-50%, 20%-50%, 30%-50%, 40%-50%, 10%-40%, 15%-40%, 20%-40%, 30%-40%, 10%-30%, 15%-30%, 20%-30%, 10%-20%, 15-20%, or 10%-15% of the total weight of the composition. In some instances, the first excipient comprises about 70% to about 90% of the total weight of the composition. In some instances, the first excipient comprises about 70% to about 90% of the total weight of the composition. In some instances, the second excipient comprises about 5% to about 15% of the total weight of the composition, for example, about 5%-15%, 5%-10%, or 10%-15% of the total weight of the composition. In some instances, the second excipient comprises about 10% of the total weight of the composition. In some instances, for example, the first excipient comprises about 8% to about 90% of the total weight of the composition, and the second excipient comprises about 10% of the total weight of the composition. In some instances, the first excipient can be about 5% to about 90% of the total weight of the composition, and the second excipient can be about 10% of the total weight of the composition.

In some cases with respect to the microcrystalline cellulose component of the compositions presented herein, generally, acceptable microcrystalline cellulose can include microcrystalline cellulose obtained by decomposing cellulose materials such as pulp by either or both of acid and alkaline hydrolyses, then purifying the hydrolysate, and crushing or grinding it before, during, or after drying. In some instances, microcrystalline cellulose of a select average particle diameter size can be obtained, for example, via appropriate processing, e.g., via fine grinding using a high-speed rotary impact mill or air attrition mill as necessary, and size sorting. In some instances, microcrystalline cellulose components utilized as part of the microcellulose of the compositions presented herein can include products available under the trade names of Ceolus® PH-F20JP (e.g., average particle size about 20-23 microns, bulk density about 0.23 g/cm$^3$, repose angle not less than 60 degrees), Ceolus® PH-301(e. g., average particle size about 50 microns, bulk density about 0.41 g/cm$^3$, repose angle about 41 degrees), Ceolus® PH-101(e.g., average particle size about 50 microns, bulk density about 0.29 g/cm$^3$, repose angle about 45 degrees), Ceolus® PH-102 (e.g., average particle size about 90 microns, bulk density about 0.3 g/cm$^3$, repose angle about 42 degrees), and Ceolus® PH-302 (available from Asahi Kasei Corporation, e.g., average particle size about 90 microns, bulk density about 0.43 g/cm$^3$, repose angle about 38 degrees), and Avicel® PH-105 (e.g., average particle size about 20 microns, bulk density about 0.20-0.30 g/cm$^3$), Avicel® PH-101(e.g., average particle size about 50 microns, bulk density about 0.26-0.31 g/cm$^3$), Avicel® PH-102 (e.g., average particle size about 100 microns, bulk density about 0.28-0.33 g/cm$^3$), Avicel® PH-301(e.g., average particle size about 50 microns, bulk density about 0.34-0.45 g/cm$^3$), and Avicel® PH-302 (available from FMC Biopolymer Corporation, e.g., average particle size about 100 microns, bulk density about 0.35-0.46 g/cm$^3$). In some instances, compositions that can be used in conjunction with the methods and compositions presented herein can comprise Ceolus® PH-F20JP and Ceolus® PH-301.

In some instances, average particle size diameters, for example, the average particle size diameters of the microcrystalline portions of the compositions described herein, can be determined using standard techniques, for example, via a laser-diffraction particle size distribution analyzer or via sorting methods. In some instances, the average particle diameter size refers to a diameter that divides particles into two groups of equal numbers: a group with greater diameters and a group with smaller diameters. In some instances, an average diameter size determined using a laser-diffraction particle size distribution analyzer corresponds to 50% volume in a determined cumulative particle size distribution curve. In some instances, an average particle diameter size can, for example, be determined by a sorting method that corresponds to 50% (W/W) on a cumulative particle size distribution curve that can be obtained by sorting an appropriate amount of the particle being assessed, for an appropriate time, e.g., ten minutes, on an electromagnetic sieve shaker, using standard sieves and weighing the sample remaining on each sieve.

In some instances, a microcrystalline cellulose component of the composition comprises a first microcrystalline cellulose portion with an average particle diameter size of about 30 μm or less, and a second microcrystalline cellulose portion with an average particle size diameter of about 30-100 μm. In some instances, a first microcrystalline cellulose portion can have an average particle diameter size of about 15-30 μm. In some instances, a first microcrystalline cellulose portion can have an average particle diameter size of about 18-20 μm. In some instances, a first microcrystalline cellulose portion can have an average particle diameter size of about 20 μm. In some instances, a second microcrystalline cellulose portion can have an average particle diameter size of about 45-65 μm. In some instances, a second microcrystalline cellulose portion can have an average particle diameter size of about 45-55 μm. In some instances, a second microcrystalline cellulose portion can have an average particle diameter size of about 50-55 μm. In some instances, a second microcrystalline cellulose portion can have an average particle diameter size of about 50 μm. In some instances, a first microcrystalline cellulose portion can have an average particle diameter size of about 20 μm, and a second microcrystalline cellulose portion can have an average particle size diameter of about 50 μm. In some instances, a first microcrystalline cellulose portion can have an average particle diameter size of about 30 lam or less, for example, about 15-30 μm, about 18-20 μm, or about 20 μm, and a second microcrystalline cellulose portion can have an average particle diameter size of about 45-65 μm, about 45-55 μm, about 50-55 μm, or about 50 μm.

In some instances, a microcrystalline cellulose component of the composition comprises about 10 to about 99%, e.g., about 15 to about 99%, of the total weight of a composition. In some instances, the microcrystalline cellulose component of a composition comprises about 53 to about 99%, about 76 to about 99%, about 76 to about 97%, about 90 to about 97%, or about 90 to about 95% of the total weight of the composition. In some instances, a microcrystalline cellulose component of a composition comprises about 10 to about 98%, about 18 to about 98%, about 18 to about 91%, about 67 to about 91%, or about 67 to about 83%. In some instances, a microcrystalline cellulose component of a composition comprises about 53%, about 76%, about 90%, about 95%, about 97%, or about 99% of the total weight of the composition. In some instances, a microcrystalline cellulose component of the composition comprises about 10%, about 18%, about 66%, about 83%, about 91%, or about 98% of the total weight of the composition. In some instances, a first microcrystalline cellulose portion comprises about 3.0 to about 90%, e.g., about 8.0 to about 90%, of the total weight of a composition, and a second microcrystalline cellulose portion comprises about 10% of the total weight of a composition. In some instances, a first microcrystalline cellulose portion comprises about 43 to about 89%, about 66 to about 89%, about 66 to about 87%, about 80 to about 87%, or about 80 to about 85% of a total weight of a composition, and a second microcrystalline cellulose portion comprises about 10% of the total weight of a composition. In some instances, a microcrystalline cellulose component of a composition comprises about 1 to about 88%, about 8 to about 88%, about 8 to about 81%, about 57 to about 81%, or about 57 to about 83%, and a second microcrystalline cellulose portion comprises about 10% of the total weight of a composition. In some instances, the microcrystalline cellulose component of a composition comprises about 43%, about 66%, about 80%, about 85%, about 87%, or about 89% of the total weight of a composition, and a second microcrystalline cellulose portion comprises about 10% of the total weight of a composition. In some instances, the microcrystalline cellulose component of a composition comprises about 1%, about 8%, about 57%, about 73%, about 81%, or about 88% of the total weight of a composition, and a second microcrystalline cellulose portion comprises about 10% of the total weight of a composition.

In some instances, with respect to tribasic calcium phosphate (also known as hydroxyapatite), any pharmaceutically acceptable tribasic calcium phosphate can be used in conjunction with the methods and compositions presented herein. In some instances, a tribasic calcium phosphate utilized can have an average particle diameter of about 10-100 μm, for example, about 10-75 μm, about 10-50 μm, about 10-30 μm, or about 10 μm. In some instances, not less than 90% of the tribasic calcium phosphate particles in the compositions presented herein have a diameter less than 150 μm, and not more than 5% of the particles in the composition have a diameter less than 10 μm. In some instances, an overall average particle size of the tribasic calcium phosphate particles in the compositions presented herein may comprise about 15 to about 30 μm, about 18 to about 25 μm, about 18 to about 20 μm, or about 20 μm.

In some instances, greater than or equal to about 90% of the tribasic calcium phosphate particles have a diameter less than 150 μm. In some instances, an overall average particle size of tribasic calcium phosphate particles may comprise about 15 to about 30 μm, about 18 to about 25 μm, about 18 to about 20 μm, or about 20 μm. In some instances, less than or equal to about 5% of the tribasic calcium phosphate particles have a diameter less than 10 μm. In some instances, for a tribasic calcium phosphate particles, greater than or equal to about 90% of the particles may comprise a diameter less than 150 μm; and an overall average particle size can be about 15 to about 30 μm, about 18 to about 25 μm, about 18 to about 20 μm, or about 20 μm; and less than or equal to about 5% of the particles have a diameter less than 10 μm.

In some instances, tribasic calcium phosphate comprises at least: about 0.1%, about 0.2%, about 0.3%, about 0.4%, about 0.5%, about 0.6%, about 0.7%, about 0.8%, about 0.9%, about 1%, about 1.5%, 2.0%, for example, 0.5-1.0% of the total weight of the composition. In some specific instances of the methods of treating headache, including migraine, the tribasic calcium phosphate comprises about 0.8% of the total weight of the composition.

Doses

In some cases, a total dose of a composition administered can be at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, or 50 mg. In some instances, a total dose of a composition administered can be about 0.1 to about 50 mg, for example, about 0.1-50.0 mg, about 0.1-25.0 mg, about 0.1-20.0 mg, about 0.1-15.0 mg, about 0.1-10.0 mg, about 0.1-5.0 mg, about 0.1-2.0 mg, about 0.1-1.0 mg, about 0.1-0.5 mg, about 0.2-50.0 mg, about 0.2-25.0 mg, about 0.2-20.0 mg, about 0.2-15.0 mg, about 0.2-10.0 mg, about 0.2-5.0 mg, about 0.2-2.0 mg, about 0.2-1.0 mg, about 0.2-0.5 mg, about 0.5-55.0 mg, 0.5-25.0 mg, about 0.5-20.0 mg, about 0.5-15.0 mg, about 0.5-10.0 mg, about 0.5-5.0 mg, about 0.5-2.0 mg, about 0.5-1.0 mg, about 1.0-25.0 mg, about 1.0-50.0 mg, about 1.0-20.0 mg, about 1.0-15.0 mg, about 1.0-10.0 mg, about 1.0-5.0 mg, about 1.0-2.0 mg, about 2.0-50.0 mg, about 2.0-25.0 mg, about 2.0-20.0 mg, about 2.0-15.0 mg, about 2.0-10.0 mg, about 2.0-5.0 mg, about 5.0-25.0 mg, about 5.0-20.0 mg, about 5.0-15.0 mg, about 5.0-10.0 mg, about 10.0-50.0 mg, about 0.5-25.0 mg, about 10.0-20.0 mg, about 10.0-15.0 mg, about 15.0-25.0 mg, about 15.0-20.0 mg, about 20-40 mg, or about 25-35 mg. In some instances, for example, a total dose of a composition administered can be about 25-35 mg.

In some cases, a composition comprises a total dose of an active agent administered of at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg. In some instances, a composition may comprise a total dose of an active agent administered at about 0.1 to about 10.0 mg, for example, about 0.1-10.0 mg, about 0.1-9.0 mg, about 0.1-8.0 mg, about 0.1-7.0 mg, about 0.1-6.0 mg, about 0.1-5.0 mg, about 0.1-4.0 mg, about 0.1-3.0 mg, about 0.1-2.0 mg, about 0.1-1.0 mg, about 0.1-0.5 mg, about 0.2-10.0 mg, about 0.2-9.0 mg, about 0.2-8.0 mg, about 0.2-7.0 mg, about 0.2-6.0 mg, about 0.2-5.0 mg, about 0.2-4.0 mg, about 0.2-3.0 mg, about 0.2-2.0 mg, about 0.2-1.0 mg, about 0.2-0.5 mg, about 0.5-10.0 mg, about 0.5-9.0 mg, about 0.5-8.0 mg, about 0.5-7.0 mg, about 0.5-6.0 mg, about 0.5-5.0 mg, about 0.5-4.0 mg, about 0.5-3.0 mg, about 0.5-2.0 mg, about 0.5-1.0 mg, about 1.0-10.0 mg, about 1.0-5.0 mg, about 1.0-4.0 mg, about 1.0-3.0 mg, about 1.0-2.0 mg, about 2.0-10.0 mg, about 2.0-9.0 mg, about 2.0-8.0 mg, about 2.0-7.0 mg, about 2.0-6.0 mg, about 2.0-5.0 mg, about 2.0-4.0 mg, about 2.0-3.0 mg, about 5.0-10.0 mg, about 5.0-9.0 mg, about 5.0-8.0 mg, about 5.0-7.0 mg, about 5.0-6.0 mg, about 6.0-10.0 mg, about 6.0-9.0 mg, about 6.0-8.0 mg, about 6.0-7.0 mg, about 7.0-10.0 mg, about 7.0-9.0 mg, about 7.0-8.0 mg, about 8.0-10.0 mg, about 8.0-9.0 mg, or about 9.0-10.0 mg. In some instances, for example, a total dose administered may comprise about 0.5 mg. In some instances, a total dose administered may comprise about 0.1-5 mg. In some instances, a total amount administered may comprise about 0.5-5 mg. In some instances, a total amount administered may comprise about 0.5-3 mg. In some instances, a total amount administered may comprise about 1-2 mg.

Methods of Making Compositions

In some cases, the present disclosure provides methods for making compositions herein, including blending, grinding, granulating, spray-drying, freeze-drying, and/or melt-extruding.

In some instances, the present disclosure provides for a method of making an intranasal pharmaceutical composition, comprising spray drying/freeze-drying/melt-extruding an active agent and at least one member selected from the group consisting of a thickening agent, a carrier, a pH adjusting agent, a sugar alcohol, and any combination thereof, to produce particles, wherein: the particles may comprise the active agent; at least about 20 percent by weight of the active agent in the particles may be amorphous as determined by X-ray diffraction. In some instances, an active agent disclosed herein can be suspended in methanol before spray drying. In some instances, particles may comprise an active agent and a thickening agent. In some instances, particles may comprise an active agent and a carrier. In some instances, particles comprise an active agent, a carrier, and a thickening agent. In some instances, a method further comprises blending particles with an additional amount of a carrier. In some instances, a method further comprises blending particles with an additional carrier, additional thickening agent, or any combination thereof. In some instances, particles may comprise an active agent and are free from a thickening agent, a carrier, or a combination thereof. In some instances, solubility can be measured at a pH ranging from about 6.8 to about 7.4. In some instances, particles may comprise a carrier that can be at least partially water insoluble at 37±0.5° C. In some instances, water insolubility may be measured at a pH ranging from about 6.8 to about 7.4. In some instances, particles further comprise a thickening agent, and wherein a carrier can have lower water solubility than that of a thickening agent. In some instances, particles comprise a carrier that can be at least partially adhesive to mucus. In some instances, particles comprise a carrier that comprises an oligosaccharide, a polysaccharide, or any combination thereof. In some instances, a carrier may comprise microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, 13 cyclodextrin, or any combination thereof. In some instances, particles may comprise an average particle size of from about 15 to about 100 μm, as measured by laser diffraction. In some instances, a carrier may comprise an average particle size of about 20 to about 50 μm, as measured by laser diffraction. In some instances, particles may comprise a thickening agent that can be at least partially water soluble 37±0.5° C. In some instances, water solubility can be measured at a pH ranging from about 6.8 to about 7.4. In some instances, particles may further comprise a carrier, and wherein a thickening agent can have higher water solubility than that of a carrier. In some instances, particles may comprise a thickening agent that binds to an active agent. In some instances, particles may further comprise a carrier, and wherein a thickening agent binds to an active agent and a carrier. In some instances, particles may comprise a thickening agent that may comprise a polysaccharide. In some instances, a thickening agent comprises hydroxypropyl methylcellulose (HPMC), HPMC acetate succinate, hydroxypropyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, particles comprise a thickening agent and may comprise an average particle size of from about 10 to about 50 μm, as measured by laser diffraction. In some instances, particles may comprise an average particle size of about 15 μm, as measured by laser diffraction. In some instances, particles comprise a thickening agent and a carrier and have an average particle size of from about 10 to about 50 μm, as measured by laser diffraction. In some instances, particles an average particle size of about 20 μm, as measured by laser diffraction.

In some cases, provided herein is a method for generating a composition, comprising spray-drying/freeze-drying/melt-extruding an active agent, optionally with a water insoluble polysaccharide muco-adhesive carrier (e.g., MCC), a sugar alcohol such as mannitol, and/or a water soluble polysaccharide viscosity increasing agent (e.g., HPMC). In some instances, an active agent can be produced by grinding, evaporation, spray coating, or freeze-drying. In some instances, a method of making further comprises physically blending an active agent with additional muco-adhesive carrier (e.g., MCC) and/or a fluidizer (e.g., tribasic calcium phosphate). In some instances, provided herein are methods of manufacturing a spray dried particle (SDRP) with an active agent and muco-adhesive carrier (e.g., MCC), without viscosity increasing agent (e.g., HPMC). In some instances, provided herein are methods of manufacturing spray dried particles (SDRP) with an active agent and a viscosity increasing agent (e.g., HPMC), without a muco-adhesive carrier (e.g., MCC). In some instances, provided herein are methods of manufacturing spray dried particles (SDRP) with an active agent only, without a muco-adhesive carrier (e.g., MCC) or a viscosity increasing agent (e.g., HPMC).

In some instances, a composition described herein can be made using standard techniques. In some instances, for example, components of compositions can be mixed while applying a shearing force, e.g., via a high shear mixer/stirrer. Alternatively, for example, components of compositions can be homogeneously mixed using, e.g., a mortar or V-blender.

In some instances, a composition presented herein may be encapsulated prior to administration. For example, compositions presented herein can be encapsulated in unit dose form. In some instances, encapsulated compositions may be released from a capsule prior to administration. In some instances, compositions may be released from a capsule upon administration. In some instances, compositions can, for example, be intranasally administered utilizing devices designed to accept and deliver compositions that may have been encapsulated. In some instances, a fill weight of a capsule comprises an appropriate excess amount of a composition such that a desired dose may be administered, taking into account a select administration device being utilized.

Devices

Also provided herein are devices for intranasal delivery. An intranasal delivery device can be used for administering a composition to a subject in need of treatment or prevention. Delivery of a composition can be performed by a medical professional and/or by a subject in need of treatment or prevention (e.g., a human subject). As described herein, devices can be pre-loaded with a single-dose composition. In some instances, the device can be a single-use device. In some instances, a device can be pre-primed or used without priming, prior to dosing. Also disclosed herein are methods for treating or prevention of a condition or disease, e.g., a migraine, comprising actuating a device comprising a composition disclosed herein. In some instances, administration of a composition requires less than about: 20, 15, 10, 5, 4, 3, 2, 1, 0.5, or 0.25 minutes to deliver an effective dose of an active agent. In some instances, a method optionally comprises visually inspecting an amount of a composition remaining in a reservoir and repeating a method (e.g., 1-2 more times) until a sufficient dose can be delivered. In some instances, a device can be one as described in US 2019/0091424, US 2011/0045088, or WO 2012/105236, each of which is incorporated herein by reference for its disclosure of devices that can be utilized to intranasally administer formulations to a primate, for example, to a human. In some instances, a device used to administer a composition disclosed herein can be a Fit-lizer™ (SNBL, LTD) intranasal dispenser device.

In some instances, said pharmaceutical composition can be provided in a device configured for said administration to said human subject. In some instances, said device can require no priming or be a pre-primed device. In some instances, a reservoir housing said pharmaceutical composition in said device can be free from metal or glass. In some instances, said device can be free from metal or glass. In some instances, said administration requires less than about: 15, 10, 5, 4, 3, 2, 1, 0.5, or 0.25 minutes to deliver an effective dose of said active agent. In some instances, said pharmaceutical composition can be in a single unit dose. In some instances, said device can be actuatable with one hand. In some instances, said device can be stored for about twelve months or less, at about 20° C. to about 25° C., and at about 60% relative humidity prior to actuating said device. In some instances, a device can be adapted to deliver at least about 85% (e.g., about: 90%, 95%, 98%, or 100%) of a composition into a nostril of a subject after a single, two, or three times of activation of a manual air pump, for example about 90-95% or more in a single puff. In some instances, at least about 90% of a composition can be delivered into a nostril of a subject after a single, two, or three times of activation of a manual air pump.

In some instances, a device described herein can comprise at least four parts, e.g., a nozzle, a retainer, a poppet valve, and a pump. In some instances, a composition can be introduced into a nozzle of a device, which can serve as a reservoir. In some instances, a nozzle can be coupled with a pump. In some instances, devices described herein can provide for complete delivery of a composition with minimal composition remaining in a device after activation of a device. In some instances, a poppet valve can be adapted to regulate airflow from a pump to a nozzle when a device is activated. In some instances, a poppet valve can be adapted to prevent movement of a composition from a reservoir in a device upstream to a pump in a device. In some instances, a poppet valve can comprise slits (canals or grooves) that can be used to generate a vortex in a reservoir to enable efficient delivery of a composition. In some instances, grooves in a poppet valve can be positioned to permit laminar air flow in a reservoir. In some instances, grooves in a poppet valve can be positioned to create spinning air flow in a reservoir when a pump is activated.

In some cases, the present disclosure provides administration of a composition disclosed herein with a device that may comprise: a nozzle having a reservoir disposed within the nozzle, a poppet valve at least partially fit into the reservoir, a retainer that is hollow and holds the poppet valve, and a manual air pump, e.g., operably linked to an upstream end of the nozzle and a downstream end of the retainer, wherein the poppet valve can have one or more contacting points with the retainer. In some instances, the one or more contacting points are one or more inner ribs. In some instances, the retainer can have an inner circumferential groove based from an upstream end of the retainer. In some instances, a rim of the circumferential groove of the retainer can be in contact with the one or more contacting points of the poppet valve. In some instances, the retainer immobilizes the poppet valve. In some instances, when the device is activated, a portion of air from the pump flows into the retainer along the circumferential groove and travels through surface grooves of the retainer to generate a vortex into the reservoir. In some instances, the one or more air intake holes of the retainer allows outside air to enter the pump after the device is activated. In some instances, the reservoir contains the composition. In some instances, a device can be adapted to deliver at least about 85% (e.g., about: 90%, 95%, 98%, or 100%) of a composition into a nostril of a subject after a single, two, or three times of activation of a manual air pump, for example about 90-95% or more in a single puff. In some instances, at least about 90% of a composition can be delivered into a nostril of a subject after a single, two, or three times of activation of a manual air pump. In some instances, a composition can be present in an amount of about 1 to about 30 mg. In some instances, a composition can be present in an amount of about 20 mg. In some instances, a nozzle further comprises a breakable tab positioned at a downstream end of a nozzle. In some instances, a device can be a single-use device. In some instances, a poppet valve further comprises a conical top section. In some instances, a conical top section can be connected to a first shelf that can be connected to a first cylindrical section. In some instances, a first cylindrical section can be connected to a second shelf that can be connected to a second cylindrical section. In some instances, a poppet valve can have one or more surface grooves. In some instances, a poppet valve can have about 3 to about 20 surface grooves, for example about 8 surface grooves. In some instances, one or more surface grooves creates a vortex in a reservoir when a device is activated. In some instances, one or more surface grooves are present on a second shelf. In some instances, a poppet valve can have about 2 to about 10 inner ribs. In some instances, a poppet valve can have about 3 inner ribs. In some instances, a poppet valve can be at least partially located within a reservoir. In some instances, a poppet valve can be at least partially located within a manual air pump. In some instances, a poppet valve comprises a cavity. In some instances, a device can be less than about 100 cm$^3$ in volume. In some instances, a device can be less than about 50 cm$^3$ in volume. In some instances, a device can be about 30 cm$^3$ in volume. In some instances, a device can have a mass of less than about 20 grams. In some instances, a device can have a mass less than about 10 grams. In some instances, a device can have a mass of about 6-7 grams. In some instances, a reservoir can have an inner diameter of less than about 10 mm. In some instances, a reservoir can have an outer diameter of about 8 to about 9 mm. In some instances, an outer diameter of a reservoir can be about 8.7 to about 8.9 mm. In some instances, an upstream end of a reservoir can have smooth surface adapted to contact the poppet valve. In some instances, a poppet valve can have an outer diameter of about 7 to about 8 mm, for example about 7.7 to about 7.9 mm. In some instances, an opening of a manual air pump can be wider than an outer diameter of a poppet valve. In some instances, a retainer contains an outer circumferential rim that can be wider than an opening of a manual air pump. In some instances, a retainer can have two air intake holes. In some instances, one or more air intake holes are about 0.2-0.4 mm wide. In some instances, a retainer can be at least partially fit into a manual air pump. In some instances, a portion of a poppet valve fit into a nozzle can be about 5 mm to about 6 mm, for example 5.7 mm to about 5.9 mm, in length parallel to an upstream to downstream axis. In some instances, a nozzle can have a length parallel to an upstream to downstream axis of between 5 mm and 40 mm. In some instances, a nozzle of a device comprises a clear, lightly tint, or translucent material.

Methods of Use

In some cases, routes of administration of a pharmaceutical composition disclosed herein include nasal, pulmonary, buccal, or sublingual administration. In some instances, a method uses a device disclosed herein to intranasally deliver a composition in a subject in need thereof, comprising positioning a nozzle of the device at least partially into a nostril of the subject and activating the manual air pump, wherein the nozzle comprises the composition. In some instances, the method treats a disease or condition of the subject, for example a headache such as migraine. In some instances, the composition comprises an active agent disclosed herein, for example dihydroergotamine or a pharmaceutically acceptable salt thereof.

In some instances, a disease or condition may comprise pain, hormone disorder, a headache, amyotrophic lateral sclerosis, Parkinson's disease, stress, anxiety, nausea, emesis, aggression, pain, neuropathic pain, sleeplessness, insomnia, restless leg syndrome, depression, or any combination thereof. In some instances, a disease or condition may comprise a headache. In some instances, a headache may comprise a migraine headache, a cluster headache, a hemicrania continua headache, a chronic headache, a tension headache, a chronic tension headache, or any combination thereof. In some instances, a headache can be a migraine headache. In some instances, a headache can comprise a cluster migraine, cluster headache, post-traumatic headache, hemiplegic migraine, basilar migraine, episodic migraine, chronic migraine, refractory migraine, migraine attack (optionally when treatment is initiated at least 1-3 hours (e.g., 2 hours) after an onset of attack), migraine attack when treatment is initiated at the earliest premonitory sign or symptom, pediatric migraine, status migraine, chronic daily headache, a migraine attack with allodynia, menstrually-associated migraine, menstrual migraine, migraine-upon-awakening, or rapid-onset migraine. In some instances, a headache can be a migraine headache with aura. In some instances, a headache can be a migraine headache without aura. In some instances, a headache can be moderate to severe. In some instances, a headache can be acute. In some instances, a pharmaceutical composition can be administered for at least one day, two days, three days, four days, five days, six days, one week, one month, or one year. In some instances, an administration of a pharmaceutical composition may be administered 1 time, 2 times, 3 times, 4 times, 5 times, 6 times, 7 times, or 8 times daily. In some instances, a pharmaceutical composition can be in a single unit dose. In some instances, a pharmaceutical composition can be a unit dose of from about 5 mg to about 50 mg. In some instances, a unit dosage of a pharmaceutical composition contains about 0.5 mg to about 25 mg of an active agent. In some instances, a subject can be a primate. In some instances, a subject can be a human. In some instances, a subject can be a monkey.

In some instances, an administration disclosed herein can be an intranasal administration. In some instances, said human subject experiences a relief of a migraine symptom (e.g., pain, photophobia, phonophobia, nausea, or any combination thereof) within about 2 hours or about 1 hour following said administration. In some instances, said human subject experiences said relief within about: 45, 30, or 15 minutes following said administration. In some instances, said human subject experiences said relief sustained for 2 to 24 hours following said administration. In some instances, said method treats or prevents a headache. In some instances, said administration can be repeated for a second dose or more doses at about every 24 hours or every 1-12 hours, for example 2-8 hours or 2-24 hours (e.g., 2, 3, 4, 5, 6, 7, 8, 9, 10, 12, 14, 16, 18, 20, 22, or 23 hours), after a first dose. In some instances, said administration can be repeated about: every 2 hours, every 2-6 hours, every 2-3 hours, evert 2-4 hours, or every 4-6 hours. In some instances, said administration can be repeated for a time period of 1, 2, 3, 4, or 5 days. In some instances, said administration can be repeated 1, 2, or 3 times only, i.e., 2, 3, or 4 doses in total respectively (to the same nostril, or to different/alternating nostrils, for example a first dose to one nostril and then 1, 2, 3, or 4 hours later, a second dose to the other nostril to treat a migraine).

In some cases, an administration disclosed herein comprises delivering two or more doses (e.g., 2, 3, or 4 doses) of a pharmaceutical composition in two or more devices (e.g., prefilled, or 2, 3, or 4 devices) to a same human subject. In some instances, said two or more doses are delivered successively to one or two nostrils of said human subjects. In some instances, two doses of said pharmaceutical composition are delivered to the human subject by two of said devices, with a first dose to one nostril delivered by a first device and successively a second dose to the other nostril delivered by a second device. In some instances, said deliveries are about 1 to about 10 seconds apart (e.g., about: 2, 3, 4, 5, 6, 7, 8, or 9 seconds apart), about 10 to about 60 seconds apart (e.g., about: 15, 20, 25, 30, 40, or 50 seconds apart), at least about 30 to about 60 seconds apart, about 2 to about 10 minutes apart (e.g., about: 3, 4, 5, 6, 7, 8, or 9 minutes apart), no more than 1-14 minutes apart (e.g., no more than 2, 3, 4, 5, 6, 7, 8, 9, 10, 11, 12, or 13 minutes apart), up to 24 hours apart or at least about: 0.5, 1, 1.5, 2, 3, 4, 5, 6, 7, 8, 9, 10, 12, 14, 16, 18, 20, 22, or 24 hours apart, or any combination thereof. In some instances, such deliveries are to treat a cluster headache. In some instances, said two doses are delivered simultaneously to two nostrils of said human subjects. In some instances, each of said devices can be prefilled with a single dose unit of said pharmaceutical composition. In some instances, said pharmaceutical composition comprises dihydroergotamine or a pharmaceutically acceptable salt thereof, for example dihydroergotamine mesylate. In some instances, said dihydroergotamine mesylate can be present in an amount of about: 3, 3.5, 4, 4.5, 5, 5.5, 6, 6.5, 7, or 7.5 mg.

In some instances, said method further comprises monitoring a vital sign of said human subject. In some instances, said vital sign can be at least one of blood pressure, heart rate, body temperature, respiration rate, oxygen saturation, or electrocardiogram. In some instances, said human subject performs said monitoring. In some instances, said monitoring comprises using an electronic device such as a smart phone or watch. In some instances, said electronic device can be portable. In some instances, said electronic device can be wearable for example a watch.

In some instances, provided herein is a method of treating a disease or a condition, including pain, headache, or hormone disorder, comprising administering intranasally (e.g., through a nasal cavity) a composition comprising an active agent. In some instances, other possible mucosal routes of administration include conjunctival administration, buccal administration, and sublingual administration. In some instances, buccal and sublingual have an advantage of being user friendly and non-invasive, and can be self-administered. In some instances, another alternative route to oral may comprise transdermal delivery of active agents through a patient's skin. In some instances, another form of administration may comprise intradermal injection (administration to a dermis) and subcutaneous injection (administration to a fat layer below the skin). In some instances, a composition comprises an active agent, microcrystalline cellulose with an average particle diameter size of about 100 µm or less, and optionally tribasic calcium phosphate. In some instances, a composition comprises an active agent, a microcrystalline cellulose portion with an average particle size diameter of about 50-55 µm, e.g., about 50 µm, comprising about 10% of a total weight of a composition, a microcrystalline cellulose portion with an average particle size of about 20 µm comprising about 3 to about 90%, e.g., about 8 to about 90%, of a total weight of a composition and, optionally, a fluidizing agent. In some instances, compositions utilized as part of a method may further comprise an active agent disclosed herein, e.g. caffeine, for example, anhydrous caffeine.

"Treating," or "Treatment" as used with a method disclosed herein, refers to an amelioration, reduction, or elimination of at least one symptom of a disorder being treated. In some instances, methods of treating headache or pain ameliorate, reduce, or eliminate at least one or more symptoms. Symptoms of headache, e.g., cluster headache, chronic daily headache or migraine, may include pain. Symptoms can also include, for example, sinus headache, sinus pain, sinus pressure, nasal congestion, running nose, watery eyes, nausea, vomiting, photophobia, phonophobia, osmophobia (aversion to, or hypersensitivity to, odors), vertigo, and/or allodynia. The symptom or symptoms can, for example, be evaluated via a four point severity scale as follows: 0=none 1=mild symptom, not interfering with normal daily activities 2=moderate symptom, causing some restriction to normal activities 3=severe, leading to inability to perform normal daily activities. Alternatively, or additionally, a symptom or symptoms, including the four listed above, can be evaluated via a four-point functional disability scale that assesses the level of impairment a symptom can have on a patient's ability to perform usual daily activities, as follows: 0=not at all impaired 1=slightly impaired 2=moderately impaired 3=severely or completely impaired. In some instances, a headache or pain can have a severity of more than about any of 1, 2, 3, 4, 5, 6, 7, 8, 9, or 10 on a scale of 0 to 10. In some instances, an intensity of headache or pain, for example, pain associated with migraine, can be measured according to a 4-point severity scale (0=no pain, 1=mild, 2=moderate, 3=severe). In some instances, methods of treating headache, for example migraine, presented herein reduce a severity of headache pain, for example pain associated with migraine, by at least one point on such a 4-point severity scale. In some instances, said human subject can be in a lying position. In some instances, said human subject can be in a supine position. In some instances, said human subject can be in a recovery position. In some instances, said human subject can be in an upright position.

In some instances, for treating a disease or condition, a total amount of a composition administered can be about: 5 mg, 10 mg, 15 mg, 20 mg, 25 mg, 30 mg, 35 mg, 40 mg, 45 mg, or 50 mg, into a single or both nostrils. In some instances, a total amount of a composition can be administered into a single nostril. In some instances, a portion of a total amount of a composition can be administered into each nostril. In some instances, about half of a total amount of a composition can be administered into one nostril and a remaining half can be administered into the other nostril. In some instances, a total dose of an active agent administered can be about 0.5-6.0 mg. In some instances, a total dose of an active agent administered can be about 1.0-6.0 mg. In some instances, a total dose of an active agent administered can be about 2.0-4.0 mg. In some instances, a total dose of an active agent administered can be about 0.1 mg, about 0.5 mg, about 1.0 mg, about 1.5 mg, about 2.0 mg, about 3.0 mg, about 4.0 mg, about 5.0 mg, about 7.5 mg, or about 10.0 mg. In some instances, a total dose can be administered into a single nostril. In some instances, a portion of a total dose can be administered into each nostril. In some instances, about half of a total dose can be administered into one nostril and the remaining half can be administered into the other nostril.

TABLE 1

Composition components and their weight amounts (approximate "about").

| Compositions | Active agent, freebase or salt (mg) | Micro-crystalline cellulose(s) (mg) | Thickening agent(s) (mg) | Sugar alcohol(s) (mg) |
|---|---|---|---|---|
| 1 | 0.5-20 | 1-30 | 0.05-5 | 1-15 |
| 2 | 1-15 | 1-25 | 0.05-2.5 | 1-10 |
| 3 | 1-10 | 1-25 | 0.05-2.5 | 1-8 |
| 4 | 1-8 | 10-25 | 0.1-2 | 4-9 |
| 5 | 1-7 | 11-20 | 0.1-2 | 4-8 |
| 6 | 1-6 | 12-19 | 0.1-0.6 | 6-7 |
| 7 | 1-5 | 13-18 | 0.1-2 | 3-9 |
| 8 | 1-4 | 14-18 | 0.1-1 | 5-7 |
| 9 | 1-3 | 15-18 | 0.1-1 | 4-8 |
| 10 | 1-2 | 16-18 | 0.1-1 | 5-7 |
| 11 | 1-1.3 | 12 | 0.1-0.15 | 5 |
| 12 | 1.3-1.5 | 12 | 0.1-0.2 | 6 |
| 13 | 1.5-1.8 | 13 | 0.15-0.2 | 5.5 |
| 14 | 2-6 | 13-18 | 0.1-1 | 4-8 |
| 15 | 2-5 | 11-13 | 0.2-0.5 | 5-7 |
| 16 | 2-4 | 11-16 | 0.2-0.6 | 4-8 |
| 17 | 2-3.5 | 12-14 | 0.2-0.4 | 5-7 |
| 18 | 2-2.5 | 12 | 0.25 | 6 |
| 19 | 2.5-3 | 13 | 0.3 | 6 |
| 20 | 3-3.5 | 14 | 0.35 | 6 |
| 21 | 3-4 | 11-15 | 0.2-0.5 | 5-7 |
| 22 | 3-5 | 14-17 | 0.3-0.5 | 5-7 |
| 23 | 3.5-5 | 14-17 | 0.3-0.6 | 4-8 |
| 24 | 4-8 | 16-21 | 0.4-0.8 | 4-8 |
| 25 | 4-7 | 17-20 | 0.5-0.7 | 5-7 |
| 26 | 4-6 | 13-18 | 0.1-1 | 4-8 |
| 27 | 4-5 | 17-19 | 0.4-0.7 | 5 |
| 28 | 4.5-5 | 14-18 | 0.4-0.6 | 7 |
| 29 | 4-4.5 | 15-16 | 0.4-0.5 | 6 |
| 30 | 5-6 | 18-19 | 0.6 | 6 |
| 31 | 5-5.5 | 17-18 | 0.5 | 5 |
| 32 | 5.5-6 | 16-17 | 0.6 | 6 |
| 33 | 1 | 12.5 | 0.15 | 5.5 |
| 34 | 1.5 | 12.5 | 0.3 | 7 |
| 35 | 1.5 | 13 | 0.25 | 6.5 |
| 36 | 1.5 | 12.5 | 0.2 | 6.5 |
| 37 | 1.5 | 12 | 0.15 | 6 |
| 38 | 1.5 | 12 | 0.1 | 5.5 |
| 39 | 2 | 13 | 0.2 | 6.5 |
| 40 | 2.5 | 13.5 | 0.3 | 7 |
| 41 | 3 | 14 | 0.5 | 7 |
| 42 | 3 | 13 | 0.3 | 6 |
| 43 | 3 | 14 | 0.5 | 5 |
| 44 | 3 | 14.5 | 0.6 | 6 |
| 45 | 3 | 15 | 0.3 | 5 |
| 46 | 3.5 | 14 | 0.4 | 6.5 |
| 47 | 3.5 | 14.2 | 0.2 | 4 |
| 48 | 3.5 | 15.7 | 0.45 | 6 |
| 49 | 3.5 | 16.8 | 0.6 | 6 |
| 50 | 4 | 16.5 | 0.5 | 5 |
| 51 | 4 | 14.3 | 0.3 | 5 |
| 52 | 4 | 14.6 | 0.4 | 4 |
| 53 | 4 | 15 | 0.5 | 5 |
| 54 | 4.5 | 14.2 | 0.2 | 4 |
| 55 | 4.5 | 15.7 | 0.45 | 6 |
| 56 | 4.5 | 16.8 | 0.6 | 6 |
| 57 | 4.5 | 16.5 | 0.5 | 5 |
| 58 | 5 | 14.3 | 0.3 | 5 |
| 59 | 5 | 14.6 | 0.4 | 4 |
| 60 | 5 | 15 | 0.5 | 5 |
| 61 | 5 | 17 | 0.7 | 7 |
| 62 | 5.5 | 17.5 | 0.5 | 5 |
| 63 | 6 | 18 | 0.6 | 6 |
| 64 | 6 | 18.2 | 0.5 | 5 |
| 65 | 6 | 18.3 | 0.6 | 5 |
| 66 | 6 | 18.5 | 0.6 | 6 |
| 67 | 6 | 18.6 | 0.6 | 6 |
| 68 | 6 | 19 | 0.6 | 6 |
| 69 | 6 | 19.2 | 0.6 | 6 |
| 70 | 6 | 19.3 | 0.5 | 5 |
| 71 | 6 | 19.5 | 0.7 | 7 |
| 72 | 6 | 19.6 | 0.7 | 7 |

EXAMPLES

Example 1—Dihydroergotamine Mesylate Intranasal Powder Formulation and Device Combination The drug-device combination product consisted of a powder formulation of DHE mesylate prefilled into a single-use delivery device for nasal administration. The dihydroergotamine mesylate intranasal powder formulation was the drug constituent part, and the dihydroergotamine mesylate intranasal device was the device constituent part of the combination.

Powder Formulations

The powder formulations were prepared with about 0.5 to 20 mg of one or more microcrystalline celluloses (MCCs) and about 1-15 mg of one or more sugar alcohols, and 0.05-5 mg of a thickening agent. The entire formulation is not too bulky for comfortable administration (for example <50 mg). The particle size delivered out of the device was large enough for minimal potential lung deposition.

The dihydroergotamine mesylate intranasal powder formulation was a combination of dihydroergotamine mesylate, one or more sugar alcohols, and MCC.

Additional powder formulations are made in the strength of 4.5 mg dihydroergotamine mesylate (3.9 mg dihydroergotamine), and 6 mg dihydroergotamine mesylate (5.2 mg dihydroergotamine).

Devices

Figure 3:
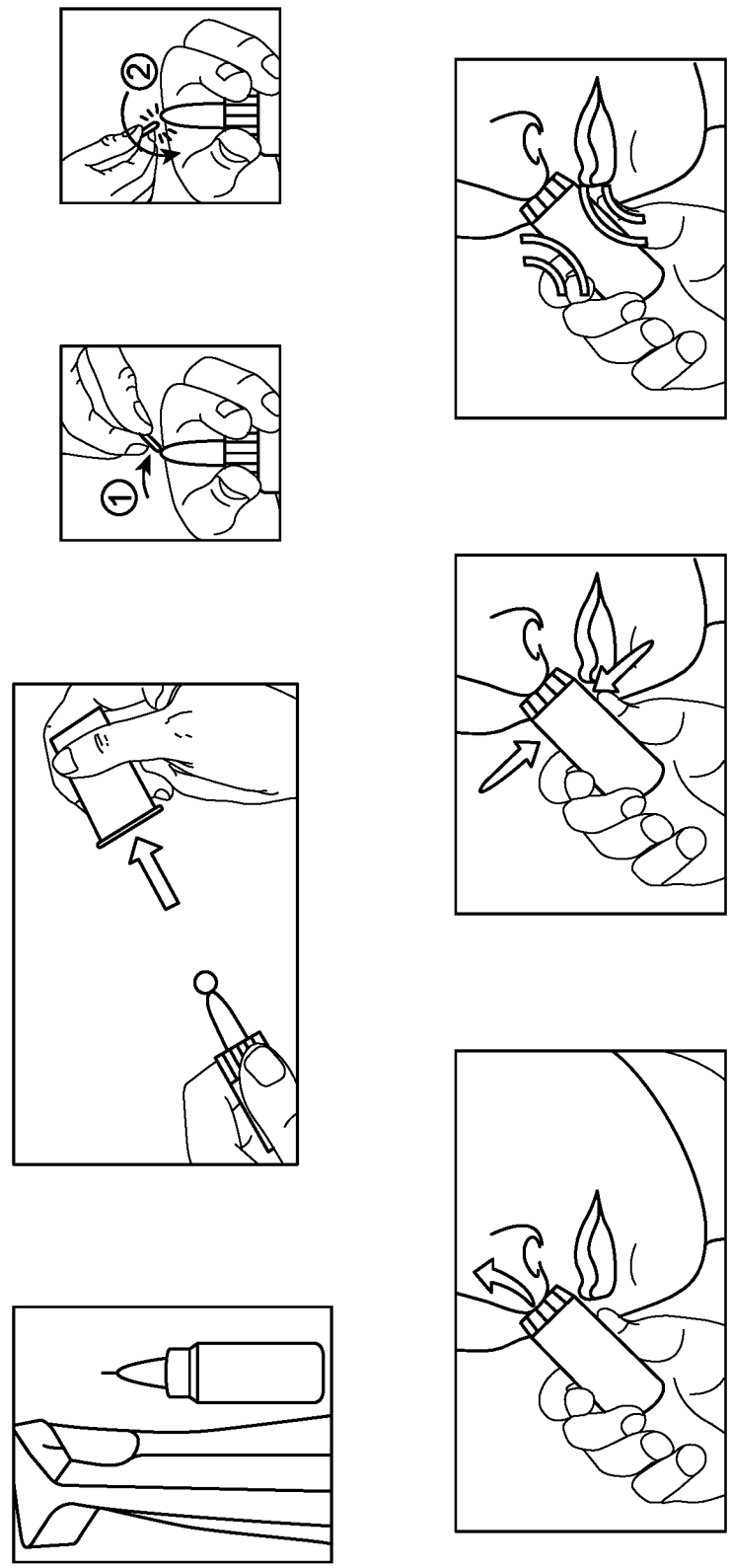
FIG. 3 shows an operation principle of an exemplary device for intranasal delivery, for example a dihydroergotamine mesylate intranasal powder. The device is optionally stored in a wrap, e.g., a foil wrap. The foil wrap is opened and the device is removed from the foil wrap. The device optionally has a protective cap, e.g., the protective cap is removed from the device before use. While the device is gripped in one hand, the tab is also gripped and bent back and forth or twisted to break it off. The nozzle is inserted into one nostril as far as it can comfortably go while avoiding squeezing the pump. Once the device is inserted into the nostril, the pump is quickly and completely squeezed between a finger and thumb until the sides of the pump are pressed into each other or close to one another. The squeezing step is repeated two times for a total of three squeezes into one nostril.

The dihydroergotamine mesylate intranasal powder devices are air driven and actuated manually. They are designed for intranasal delivery of powder formulations such as dihydroergotamine mesylate intranasal powder formulation. A drug-device combination product can contain a prefilled single-unit dose of the dihydroergotamine mesylate intranasal powder formulation. Patients do not need to fill the device, and the devices can be a single-use. The instruction for use for the devices is shown in FIG. 3.

A drawing of a suitable device is shown in FIG. 1A, and the 5 parts: Cap, Nozzle, Poppet, Retainer, and Pump are shown in FIG. 1B. The powder formulation is contained in the medicine reservoir located in the Nozzle. The Tab on the Nozzle is folded off immediately before dosing. The patient inserts the Nozzle into one nostril and squeezes the Pump, which forces air through the Nozzle and the powder formulation is expelled.

FIG. 2A illustrates a cross-sectional view of a single-use intranasal delivery device. The intranasal delivery device (100) can comprise air source, which can be a flexible vial (102). The flexible vial can function as a manual air pump (104). The flexible vial can comprise a flow inlet (not shown) and a flow outlet (106). Optionally, the flexible vial does not need to comprise a flow inlet. The flexible vial can comprise a throat (108) at the top of the flexible vial with a narrower diameter than the bottom of the flexible vial (110). The throat (108) can comprise an external thread (112) for attachment of a nozzle (114). A one way valve (116) can sit on a surface in the throat (108) of the flexible vial (102) and block the flow outlet (106) when the device is not activated (e.g., when the manual air pump is not compressed). Resting of the one way valve (116) on a surface in the throat (108) can prevent a powdered therapeutic composition (M) from entering the flexible vial (102) when the device is not activated. A one way valve (116) can comprise a top section (118), a first cylindrical section (120), a first shelf (122), a second cylindrical section (124), and a second shelf (126). One or more slits (128) can be in the surface of the first shelf. One or more slits (128) can permit flow of air or gas from the flexible vial (102) to the nozzle (114) when the manual air pump (104) is compressed.

An intranasal device (100) can further comprise a nozzle (114) that can comprise a nozzle pipe (130) which can be inserted or partially inserted into the nasal cavity or a nostril of a subject. The nozzle (114) can further comprise a nozzle hole (132), a removable or breakable cover (134), and a reservoir for a powdered therapeutic formulation (138). The reservoir for the powdered therapeutic formulation can comprise a powdered therapeutic formulation (M). The nozzle (114) can comprise a base (140) that can comprise an internal thread (142) for attachment to the throat (108) of the flexible vial (102). The internal thread of the nozzle base can mate with an external tread of the vial throat.

FIG. 2B illustrates a cross-sectional view of a single-use intranasal delivery device. The intranasal delivery device (900) can comprise air source, which can be a flexible vial (902). The flexible vial can function as a manual air pump (904). The flexible vial can comprise a flow outlet (906) and does not comprise a flow inlet when the removable or breakable cover (934) has not been removed. The flow inlet can comprise the nozzle hole (932), which can act as a flow inlet when the removable or breakable cover (934) has been removed. The flexible vial can comprise a throat (908) at the top of the flexible vial with a narrower diameter than the bottom of the flexible vial (910). The throat (908) can comprise an external thread (912) for attachment of a nozzle (914). A one way valve (916) can sit on a surface in the throat (908) of the flexible vial (902) and block the flow outlet (906) when the device is not activated (e.g., when the manual air pump is not compressed). Resting of the one way valve (916) on a surface in the throat (908) can prevent a powdered therapeutic composition (M) from entering the flexible vial (902) when the device is not activated. A one way valve (916) can comprise an inner inlet section (944), a valve cavity (946), a top section (918), a first cylindrical section (920), a first shelf (922), a second cylindrical section (924), and a second shelf (926). In some instances, the top section comprises the inner inlet section. In some instances, the valve does not comprise a top section. One or more slits (928) can be in the surface of the first shelf. One or more slits (928) can permit flow of air or gas from the flexible vial (902) to the nozzle (914) when the manual air pump (904) is compressed. An intranasal device (900) can further comprise a nozzle (914) that can comprise a nozzle pipe (930) which can be inserted or partially inserted into the nasal cavity or a nostril of a subject. The nozzle (914) can further comprise a removable or breakable cover (934), a nozzle hole (932), which can act as a flow inlet when the removable or breakable cover is removed, and a reservoir for a powdered therapeutic formulation (938). The reservoir for the powdered therapeutic formulation can comprise a powdered therapeutic formulation (M). The nozzle (914) can comprise a base (940) that can comprise an internal thread (942) for attachment to the throat (908) of the flexible vial (902). The internal thread of the nozzle base can mate with an external tread of the vial throat.

FIG. 2C illustrates another nasal spray applicator device that can be used to deliver a pharmaceutical composition described herein. A device (1) is comprised of a deformable volume (2) and a flow inlet (3b) which comprises a manual air pump (3). A device (1) is further comprised of a valve assembly (5) which comprises a check valve (11) which comprises a flow outlet (3a), a valve disk (15), a spring (14), a flow passage (7), and a poppet (16) which further comprises a deflecting surface (17). A poppet (16) is disposed within a flow passage (7) and a throat (12) which is in communication with a diffuser (13). A valve assembly further comprises one or more engaging holes (5a) for attachment to a nozzle (6). A device is further comprised of a nozzle (6) which comprises a nozzle pipe (4) which is adapted to be inserted or partially inserted into the nasal cavity or a nostril of a subject. The nozzle (6) further comprises a flow restrictor (21), a breakable cover (22), and a powdered therapeutic reservoir (23). The powdered medicine reservoir comprises a powdery therapeutic formulation (M). The nozzle (6) further comprises one or more ratchets (6a) for attachment to a valve assembly (5). The devices disclosed herein can be of any convenient dimensions for application of the therapeutic compositions contained therein, for example, a device could be between 1-6 inches in height, such as about 1 inch, about 1.5 inches, about 2 inches, about 2.5 inches, about 3 inches, about 3.5 inches, about 4 inches, about 4.5 inches, about 5 inches, about 5.5 inches, or about 6 inches in height. Dimensions for the device can be chosen based on the amount of therapeutic composition to be delivered, ease of use, ease of portability, or manufacturing convenience.

Example 2-Process of Making Dihydroergotamine Mesylate Intranasal Powder

Method 1. DHE mesylate was present in a crystalline or amorphous form (1.5, 3, and 6 mg DHE mesylate strength). The formulation contained a thickening agent (about 20% to about 25% w/w of DHE). A DHE powder formulation was prepared by grinding in a mortar DHE mesylate, the thickening agent, one or more sugar alcohols, and one or more microcrystalline celluloses. The thickening agent can be carboxymethylcellulose, polyvinylpyrrolidone, or hydroxypropyl methylcellulose. The sugar alcohol can be trehalose, galactitol, mannitol, sorbitol, or any combination thereof.

Method 2. DHE mesylate was present in a crystalline or amorphous form (1.5, 3, and 6 mg DHE mesylate strength). The formulation contained a thickening agent (about 20% to about 25% w/w of DHE). A DHE powder formulation was prepared by fluid bed granulation of DHE mesylate, the thickening agent, one or more sugar alcohols, and one or more microcrystalline celluloses. The thickening agent can be carboxymethylcellulose, polyvinylpyrrolidone, or hydroxypropyl methylcellulose. The sugar alcohol can be trehalose, galactitol, mannitol, sorbitol, or any combination thereof.

Method 3. DHE mesylate was present in in a crystalline or amorphous form (1.5, 3, and 6 mg DHE mesylate strength). A thin coating of DHE was present on MCC. The formulation contained a thickening agent (about 10% to about 15% w/w of DHE). DHE mesylate, the thickening agent, and one or more sugar alcohols, and one or more microcrystalline celluloses (at least one of which has an average particle size of about 23 microns) were added to a hydroxy-containing compound for a spray-drying process, which gave a spray dried dispersion. The spray dried dispersion was then mixed and blended with MCC and one or more sugar alcohols, resulting in a DHE powder formulation. The thickening agent can be carboxymethylcellulose, polyvinylpyrrolidone, hydroxypropyl methylcellulose, or any combination thereof. The sugar alcohol can be trehalose, galactitol, sorbitol, mannitol, or any combination thereof.

Method 4. DHE mesylate was present in a crystalline or amorphous form (1.5, 3, and 6 mg DHE mesylate strength). The formulation contained a thickening agent (about 5% to about 25% w/w of DHE). DHE mesylate, the thickening agent, one or more sugar alcohols, and one or more microcrystalline celluloses were mixed with vigorous shaking for about 10-60 minutes, optionally grinding in a mortar, and sieved through a mesh, resulting in a DHE powder formulation with an average particle diameter less than 100 μm. The thickening agent can be carboxymethylcellulose, polyvinylpyrrolidone, or hydroxypropyl methylcellulose. The sugar alcohol can be trehalose, galactitol, mannitol, sorbitol, or any combination thereof.

Example 3-Characterization of Dihydroergotamine Mesylate Intranasal Powder

In-vitro delivery characterization with a prefilled single-use device herein demonstrated an average delivered dose of about 96% with a relative standard deviation of 3.5%. The aerodynamic particle size analysis showed about 1.3% of delivered dose DHE particles with an aerodynamic particle size below 5 μm. The powder formulation showed greater than about 95% of the target amount was delivered even when lowering the actuation velocity to about 50% of the optimal value.

Example 4—Clinical Phase 1 Studies of Formulation and Device

A randomized, open-label, 2 part, 3-period crossover study was conducted to evaluate the pharmacokinetics, bioavailability, dose proportionality, safety, and tolerability of single doses of dihydroergotamine mesylate nasal powder, dihydroergotamine mesylate intramuscular injection and dihydroergotamine mesylate nasal spray in healthy adult subjects. This was a single-center, single-dose, open-label, 2-part, 3-period crossover (in each part), pharmacokinetic and safety study. Approximately thirty (30) healthy subjects (ages 18 to 50 years) received study medication. In Part 1, approximately 15 subjects received three ascending doses of dihydroergotamine mesylate intranasal powder in a 3-period crossover design. One dose strength of dihydroergotamine mesylate intranasal powder was selected for Part 2 in which approximately 15 subjects received dihydroergotamine mesylate intranasal powder, intranasal DHE spray and intramuscular DHE injection in a random order. The treatment sequences were as outlined in Table 2. The total duration of the study was approximately 4 weeks.

TABLE 2

Randomization Schedule

| Part | Number of Subjects | Period 1 Treatment | Period 2 Treatment | Period 3 Treatment |
|---|---|---|---|---|
| 1 | 15 | A | B | C |
| 2 | 5 | A or B or C* | D | E |
|  | 5 | D | E | A or B or C* |
|  | 5 | E | A or B or C* | D |

Treatment A = 1.5 mg DHE mesylate nasal powder
Treatment B = 3.0 mg DHE mesylate nasal powder
Treatment C = 6.0 mg DHE mesylate nasal powder
Treatment D = 1 mg DHE intramuscular injection (D.H.E. 45 ® or generic)
Treatment E = 2 mg DHE liquid nasal spray (Migranal ® or generic)
*One dose strength (Either A or B or C) was selected after Part 1

Sufficient numbers of volunteers were screened to enroll approximately 30 subjects in the study. Subjects who withdrew or were withdrawn from the study after dosing were not replaced. Subjects were selected from non-institutionalized members of the community at large. The screening period was up to 28 days. The treatment and follow-up period was approximately 22 days.

During each treatment period, subjects remained at the clinical research unit for approximately 48 hours. Subjects were admitted on the day before dosing in each treatment period and remained in the clinical research unit until approximately 24 hours post-dose. The study drug was administered in the morning, 60 minutes after a light standardized breakfast. Blood samples for pharmacokinetic analysis were collected at the following times with the allowed time deviation in parenthesis:
  0 (pre-dose)
  5, 10, 15 minutes (each ±2 minutes),
  30, 45, 60, 90 minutes (each ±5 minutes),
  2, 4, 6, 8 hours (each ±10 minutes),
  12, 24, 36, and 48 hours (each ±30 minutes) post-dose in each of the treatment periods.

A standardized lunch was provided approximately 4 hours after dosing. A standardized dinner was provided approximately 9-10 hours after dosing and a snack was provided approximately 12-13 hours after dosing. There was a minimum washout period of 7 (+1) days between each consecutive study drug administration. The duration of the washout period was measured from study drug administration time of the preceding period to dosing day of the subsequent period. A safety follow-up visit took place 7±2 days after the last treatment period.

Part 1 of the study was performed to select a dose level of dihydroergotamine mesylate intranasal powder for further evaluation in part 2. The secondary aims of the study were to describe the pharmacokinetics of dihydroergotamine following single dose administration of 1.5 mg, 3.0 mg and 6.0 mg of dihydroergotamine mesylate intranasal powder, to describe the pharmacokinetics of 8'hydroxy-dihydroergotamine (8'OH-DHE) following single dose administration of 1.5 mg, 3.0 mg and 6.0 mg of dihydroergotamine mesylate intranasal powder, to assess the safety and tolerability of single doses of 1.5 mg, 3.0 mg and 6.0 mg of dihydroergotamine mesylate intranasal powder.

4.1 Treatment Groups
Part 1, Periods 1, 2 and 3: DHE and 8'OH-DHE Concentration-Time Data In periods 1 and 2, 15 subjects received single intranasal inhalation doses of dihydroergotamine mesylate intranasal powder. The dose level in Period 1 was 1.5 mg dihydroergotamine mesylate intranasal powder and all subjects returned for Period 2 where they received a dose of 3.0 mg dihydroergotamine mesylate intranasal powder. In period 3, 14 subjects received a single intranasal inhalation dose of dihydroergotamine mesylate intranasal powder at a dose of 6.0 mg.

4.2 Parameters Measured

Blood samples were scheduled to be obtained before dosing and at 0.083, 0.167, 0.25, 0.5, 0.75, 1, 1.5, 2, 4, 6, 8, 12, 24, 36, and 48 hours after administration. Analysis of plasma concentration versus time data for calculation of standard pharmacokinetic (PK) parameters following nasal administration was conducted using Phoenix® WinNonlin version 6.3 or later using nominal blood sampling times. Concentration-time data for the 1.5 mg and 3.0 mg dose levels were available through 48 hours and data are available through 24 hours for the 6.0 mg dose.

4.3 Protocol of Administration

Intranasal Powder

The protocol of administration is shown in FIG. 3. A user was advised to clear his/her nose by fully blowing the nose before administration. The foil wrap was opened and a delivery device was removed from the packaging. The protective cap was removed from the device. While the device was gripped in one hand, e.g., by holding the nozzle's base, the tab was gripped by the other hand and bent back and forth to break it off. The nozzle was inserted into one nostril as far as it would comfortably go while avoiding squeezing the pump. While breathing in through a nose, the pump was quickly and fully squeezed, e.g., between a finger and thumb, until the sides of the pump were pressed into each other or the fingers touch. The squeezing step was optionally repeated two times for a total of three squeezes into each nostril.

Liquid Nasal Spray

Assembling of a medicine vial and a pump was required before use, e.g., for MIGRANAL. Administration of a full dose took more than 15 minutes, e.g., about 20 minutes. The tab was lifted back to bend the cover. In one piece the cover and metal seal were completely removed in a circular motion. The rubber stopper was removed while the vial was kept upright. The vial was then set aside. The plastic cover was removed from the bottom of the pump unit. The spray pump was inserted into the vial and turned clockwise until securely fastened. The cap was removed from the spray unit. While holding the vial away from any persons face the nasal sprayer was pumped four times before use. The spray unit was inserted into each nostril and sprayed once each time. After fifteen minutes, each nostril was sprayed again and the nasal spray pump with vial disposed of.

Intramuscular Liquid Injection

The hands of a user were washed thoroughly with soap and water. The dose of the medication was checked. The ampul was checked to see if any liquid was at the top of the ampul. If there was it was flicked with a finger to get all the liquid to the bottom portion of the ampul. The bottom of the ampul was held in one hand. The neck of the ampul was cleaned with an alcohol wipe using the other hand. The alcohol wipe was then placed against the neck of the ampul and the ampul broken open using pressure from a thumb. The subcutaneous injection was administered to the middle of the thigh of the patient, well above the knee.

4.4 Criteria for Evaluation

Pharmacokinetic Endpoints

1. Area under the concentration-time curves (AUC0-∞; AUC0-30min; AUC0-60min; AUC0-2 hr; AUC0-24 hr; AUC0-48 hr)
2. Maximum observed plasma concentration (Cmax)
3. Time to Cmax (Tmax)
4. Terminal phase half-life ($T_{1/2}$)
5. Terminal rate constant (kel)
6. Extrapolated residual area ((1-AUC0-t/AUC0-∞)*100)

Safety

The following assessment and measurements were conducted prior to dosing and/or at periodic intervals following dosing for up to 48 hours:

1. Physical examination
2. Vital signs and body weight
3. 12-lead ECG
4. Blood tests for hematology and biochemistry analysis
5. Urinalysis
6. Adverse events (AEs)
7. Review of concomitant medications
8. Subjective assessment of nasal irritation using a questionnaire, completed by the subject.
9. Objective assessment of nasal irritation using a structured examination of the nasal cavity and mucosal integrity.

Pharmacokinetics

The following pharmacokinetic parameters were calculated for both DHE and its major metabolite, 8'hydroxy-dihydroergotamine (8'OH-DHE), using standard noncompartmental analysis:

1. Area under the concentration-time curves (partial AUCs, AUC0-∞ and AUC0-t)
2. Maximum observed plasma concentration (Cmax)
3. Time to reach $C_{max}$ (Tmax)
4. Terminal phase half-life ($T_{1/2}$)
5. Terminal rate constant (kel)
6. Residual Area ((1-AUC0-t/AUC0-∞)*100)
7. CL/F
8. Vz/F
9. Metabolite/parent ratios for AUC and Cmax Plasma concentrations and pharmacokinetic parameters were summarized descriptively by treatment group and time point, where appropriate. All PK parameters were calculated using the actual post-dose blood sampling times. Each time point was evaluated separately relative to the baseline value. Descriptive statistics [N, arithmetic and geometric means, standard deviation (SD), minimum, median, maximum and coefficient of variation (CV)] were used to summarize the PK parameters for each treatment cohort.

The study variables were:

Part 1:

1. Pharmacokinetics of DHE following the administration of dihydroergotamine mesylate 1.5 mg, 3.0 mg and 6.0 mg intranasal powder (Treatments A, B and C).
2. Pharmacokinetics of 8'OH-DHE following the administration of dihydroergotamine mesylate 1.5 mg, 3.0 mg and 6.0 mg intranasal powder (Treatments A, B and C).
3. Dose proportionality of dihydroergotamine mesylate 1.5 mg, 3.0 mg and 6.0 mg intranasal powder was determined using the power model by comparing AUC0-∞, AUC0-t and Cmax as estimated from plasma DHE and 8'-β-OH-DHE concentration profiles (Treatments A, B and C).
4. Safety and tolerability of DHE in healthy adults following the administration of dihydroergotamine mesylate intranasal powder (Treatments A, B and C).

Part 2:

1. Pharmacokinetics of DHE following the administration of the selected dose level of dihydroergotamine mesylate intranasal powder (A or B or C).
2. Pharmacokinetics of DHE following the administration of 1 mg DHE intramuscular injection (Treatment D).

3. Pharmacokinetics of DHE following the administration of 2 mg DHE Migranal intranasal liquid spray (Treatment E).
4. Pharmacokinetics of 8'OH-DHE following the administration of the selected dose level of dihydroergotamine mesylate intranasal powder (A or B or C).
5. Pharmacokinetics of 8'OH-DHE following the administration of 1 mg DHE intramuscular injection (Treatment D).
6. Pharmacokinetics of 8'OH-DHE following the administration of 2 mg DHE Migranal intranasal liquid spray (Treatment E)

Relative bioavailability of the selected dose level of dihydroergotamine mesylate intranasal powder (A or B or C) was determined by comparing the dose-adjusted DHE values of AUC0t, AUC0-∞ and Cmax of dihydroergotamine mesylate intranasal powder to that of 1 mg DHE intramuscular injection (Treatment D) and 2 mg DHE Migranal intranasal liquid spray (Treatment E). Comparative bioavailability of the selected dose level of dihydroergotamine mesylate intranasal powder (A or B or C) was determined by comparing the DHE values of AUC0t, AUC0-∞ and Cmax of dihydroergotamine mesylate intranasal powder to that of the 1 mg DHE intramuscular injection (Treatment D) and 2 mg DHE Migranal intranasal liquid spray (Treatment E). Examination and reporting of all safety measures was performed (i.e. adverse events, vital signs and lab parameters) for all treatments in the study. The relative and comparative bioavailability of DHE following the administration of the dihydroergotamine mesylate intranasal powder vs. the IM DHE administration was determined by examining the 90% confidence interval (CI) for the selected dose strength mean, resulting from the analysis on the ln-transformed dose-adjusted AUC0t, AUC0-∞ and Cmax, relative to the reference group mean (Treatment D). The relative and comparative bioavailability of DHE following the administration of the dihydroergotamine mesylate intranasal powder vs. the IN DHE administration was determined by examining the 90% confidence interval (CI) for the selected dose strength mean, resulting from the analysis on the ln-transformed non dose-adjusted AUC0t, AUC0-∞ and Cmax, relative to the reference group mean (Treatments E). An analysis of the $T_{max}$ data was conducted using a nonparametric statistical test such as a wilcoxon test.

4.5 Results of Part 1 of the Clinical Study

The mean maximum concentration of DHE was 608 pg/mL for the 1.5 mg dihydroergotamine mesylate intranasal powder dose, 1140 pg/mL for the 3.0 mg dose, and increased to 1770 pg/mL for the 6.0 mg dose. For the 1.5 mg dose, the Tmax occurred at both 0.5 and 0.75 hours after dosing. For both the 3.0 mg and 6.0 mg doses, the Tmax was at 0.5 hour. Fourteen of fifteen subjects had measurable concentrations of DHE at 48 hours after dosing at 1.5 mg and the average concentration at that time was 12.1 pg/mL. All the fifteen subjects had measurable concentrations of DHE at 48 hours after dosing at 3.0 mg and the average concentration at that time was 19.9 pg/mL.

Figure 4B:
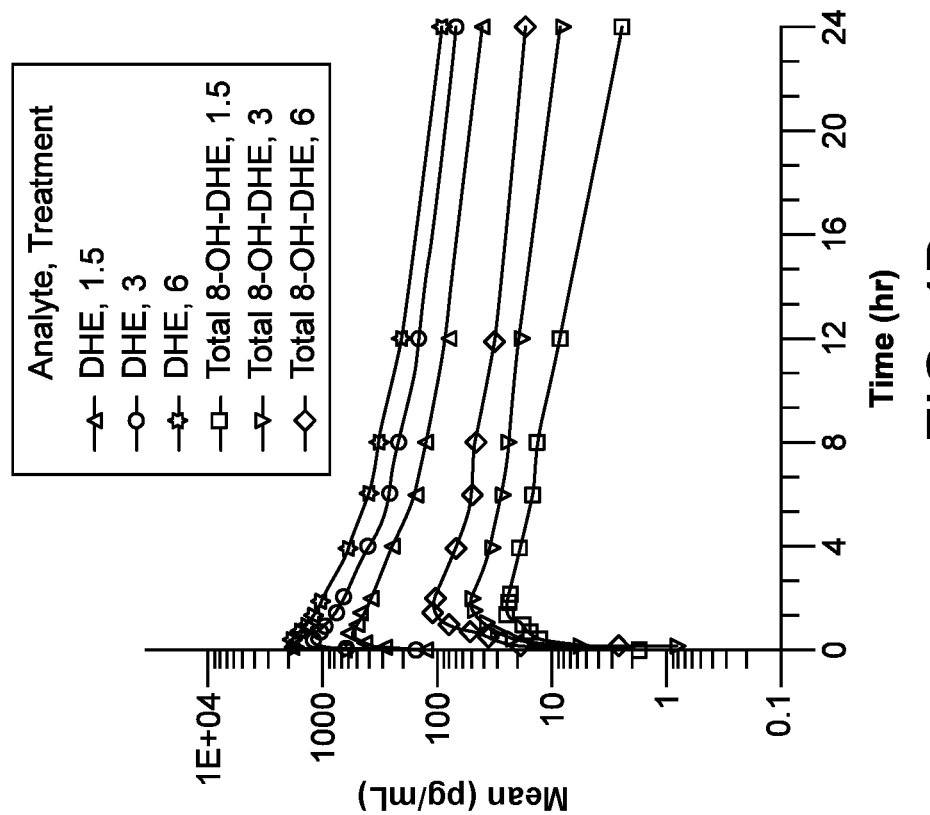
FIGS. 4A and 4B show mean dihydroergotamine mesylate (DHE) and a metabolite 8'-hydroxy dihydroergotamine (8'-OH-DHE) plasma concentrations over time in the treatments for Part 1 of the Clinical Phase 1 study described in Example 4, in a linear plot over 48 hours (FIG. 4A) and in a log-linear plot over 24 hours (FIG. 4B).
Figure 4A:
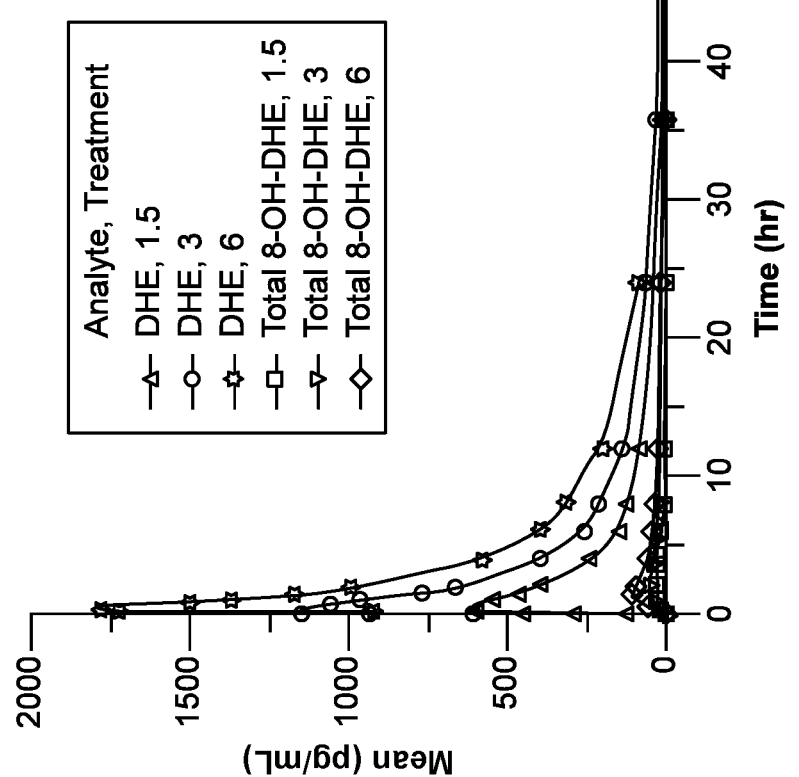

Linear and log-linear plots of the mean plasma DHE and 8'OH-DHE concentration-time data separated by treatment are displayed in FIGS. 4A and 4B, respectively. Concentrations of 8'-OH-DHE were much lower than those of the parent drug. The mean maximum concentration for 8'-OH-DHE following 1.5 mg dihydroergotamine mesylate intranasal powder was 24.5 pg/mL at a $T_{max}$ of 1.5 hours after dosing. For the 3.0 mg dose, the Tmax was at 2 hours with an average of 50.9 pg/mL. For the 6.0 mg dose, the Tmax was at 1.5 hours with an average of 108 pg/mL at that time. There was a lag time of 0.25 to 0.5 hour in the formation of 8'-OH-DHE in most subjects. For the 1.5 mg dihydroergotamine mesylate intranasal powder dose, one subject had no measurable concentrations, and another had a single measurable concentration of 8'-OH-DHE. Only 3 subjects had measurable concentrations at 24 hours after dosing and no measurable concentrations were observed at 36 or 48 hours. At the 3.0 mg dose level, 9 of 15 subjects had measurable concentrations at 24 hours. Four of the 15 subjects had measurable concentrations observed at 36 hours and only 1 subject had measurable concentrations observed at 48 hours. At the 6.0 mg dose level, 14 of the 15 subjects had measurable concentrations at 24 hours.

The Cmax for the 1.5 mg dose averaged 645 pg/mL, with a range of 111 to 2000 pg/mL, and the median Tmax was 0.75 hour. For the 3.0 mg dose, Cmax averaged 1240 pg/mL, with a range of 607 to 2950 pg/mL, and the median Tmax was 0.50 hour. The Cmax for the 6.0 mg dose averaged 1870 pg/mL, with a range of 725 to 3880 pg/mL, and the median Tmax was 0.5 hour and a mean $T_{max}$ of 23 minutes. Variability in Cmax continued to decrease from a CV % of 64.9% for the 1.5 mg dose to 46.3% for 3.0 mg to 44% for the 6.0 mg dose.

Plasma DHE concentrations displayed a bi-exponential decay profile and the average terminal phase half-life was 12.9 hours at the 1.5 mg dose, 12.6 hours at 3.0 mg, and was 8.87 hours at the 6.0 mg dose. The geometric mean AUCinf at 1.5 mg was 3840 h*pg/mL, 6640 h*pg/mL at 3.0 mg, and was 9060 h*pg/mL at 6.0 mg. Variability in AUCinf dropped from a % CV of 44.6% to 36.4% and slightly increased to 38.5% as the dose was increased from 1.5 to 3.0 mg to 6.0 mg.

Apparent clearance (CL/F) was high as evidenced by a geometric mean of 391 L/h for the 1.5 mg dose, 452 L/h at 3.0 mg, and 662 L/h at 6.0 mg. The calculated volumes of distribution (Vz/F) were large with geometric means of 7210, 8200, and 8350 L respectively.

The 8'-OH-DHE Cmax for the 1.5 mg dihydroergotamine mesylate intranasal powder dose averaged 27.8 pg/mL and for the 3.0 mg dose the average doubled to 60.5 pg/mL. The Cmax for the 6.0 mg dihydroergotamine mesylate intranasal powder dose average was 127 pg/mL which was nearly double that of the 3.0 mg dose. The median Tlag was 0.25 hour indicating a lag time for the formation of this metabolite. The median $T_{max}$ was 2 hours at dose levels 1.5 and 3.0 mg. The median $T_{max}$ was 1.5 hours at the 6.0 mg dose level. The average terminal phase half-life for the 1.5 mg dose was 13.4 hours, calculated from the available data in 11 of 15 subjects, 13.6 hours for the 3.0 mg dose using data from all subjects, and 12.3 hours for the 6.0 mg dose using data from all subjects. The geometric mean AUCinf was 454 h*pg/mL at the 1.5 mg dose, 675 h*pg/mL at the 3.0 mg dose, and 1170 h*pg/mL at the 6.0 mg dose.

The fraction of DHE converted to 8'OH-DHE was low and variable with an arithmetic mean of 0.0552 (5.52%) at 1.5 mg, 0.0821 (8.21%) at 3.0 mg, and 0.115 (11.5%) at 6.0 mg reflecting an increase in the percentage converted as the dose was increased.

The results reflected a proportional increase in Cmax with a slightly less than proportional increase in AUCinf as the dose was increased. The AUCinf/Dose result is reflected by a decrease in some subjects, but the results also reveal the decrease in variability at the higher dose level.

4.6 Results of Part 2 of the Clinical Study

In Part 2, Period 1, 27 subjects received a single intranasal inhalation dose of 6.0 mg dihydroergotamine mesylate intranasal powder (5.2 mg dihydroergotamine DHE), 25 subjects received 1 mg of intramuscular (IM) DHE, and 21 subjects received 2 mg of DHE administered as an intranasal liquid spray (Migranal). Blood samples were scheduled to be obtained before dosing and at 0.083, 0.167, 0.25, 0.5, 0.75, 1, 1.5, 2, 4, 6, 8, 12, 24, 36, and 48 hours after administration. Analysis of plasma concentration versus time data for calculation of standard pharmacokinetic (PK) parameters following nasal administration was conducted using Phoenix® WinNonlin version 6.3 or later using nominal blood sampling times.

The intranasal powder showed rapid absorption with DHE plasma concentrations of 1230 and 1850 pg/mL at 5 and 10 minutes after administration, respectively. In comparison to MIGRANAL, the intranasal powder showed approximately 2-fold higher $C_{max}$ (2180 vs 961 pg/mL), $AUC_{0-2h}$ (2980 vs 1320 h*pg/mL), and $AUC_{0-inf}$ (12000 vs 6360 h*pg/mL), respectively. The mean $AUC_{0-inf}$ of the intranasal powder was comparable to IM DHE (12000 vs 13600 h*pg/mL). The intranasal powder showed substantially lower variability compared to MIGRANAL for $C_{max}$(41% vs 76%), $AUC_{0-2h}$ (39% vs 75%), and $AUC_{0-inf}$ (39% vs 56%). The intranasal powder was well tolerated and treatment emergent AEs (TEAEs), all mild and transient, were reported in part 1 by 60%, 33% and 36% of the subjects after administration of the intranasal powder in strengths of 1.3, 2.6 and 5.2 mg (corresponding to 1.5, 3, and 6 mg DHE mesylate) respectively, and in part 2 by 41%, 15% and 19% of the subjects after administration of the exemplary intranasal DHE powder, IM DHE, and MIGRANAL, respectively.

The drug device combination here showed rapid absorption achieving effective DHE plasma concentrations within 5-10 minutes, substantially higher $C_{max}$, $AUC_{0-2h}$, $AUC_{0-inf}$ and lower variability compared to DHE nasal spray and $AUC_{0-inf}$ comparable to IM DHE. The drug device combination is a non-invasive acute migraine treatment expected to be well tolerated and to provide rapid and consistent freedom from pain and associated migraine symptoms without recurrence. Exemplary data are shown below.

Figure 6:
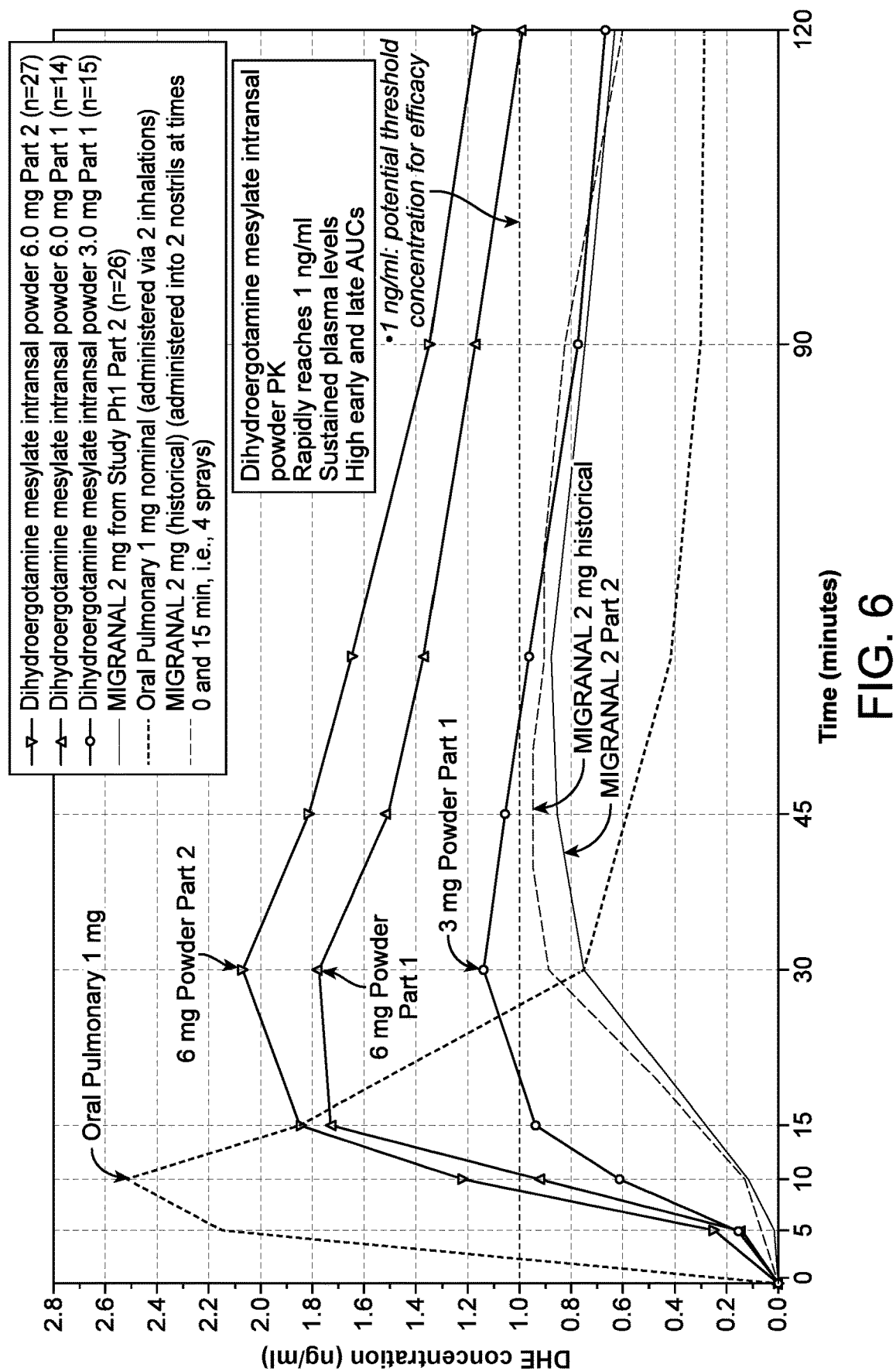
FIG. 6 shows Phase 1 study results of DHE plasma concentration of a dihydroergotamine mesylate intranasal powder formulation compared with other DHE dosage forms (0-2 hr data).

FIG. 6 shows DHE plasma concentration results of a dihydroergotamine mesylate intranasal powder Phase 1 study compared with other DHE dosage forms (0-2 hr data). Dihydroergotamine mesylate intranasal powder DHE plasma concentration profile is comparable or superior to other DHE dosage forms that have demonstrated efficacy.

Figure 7:
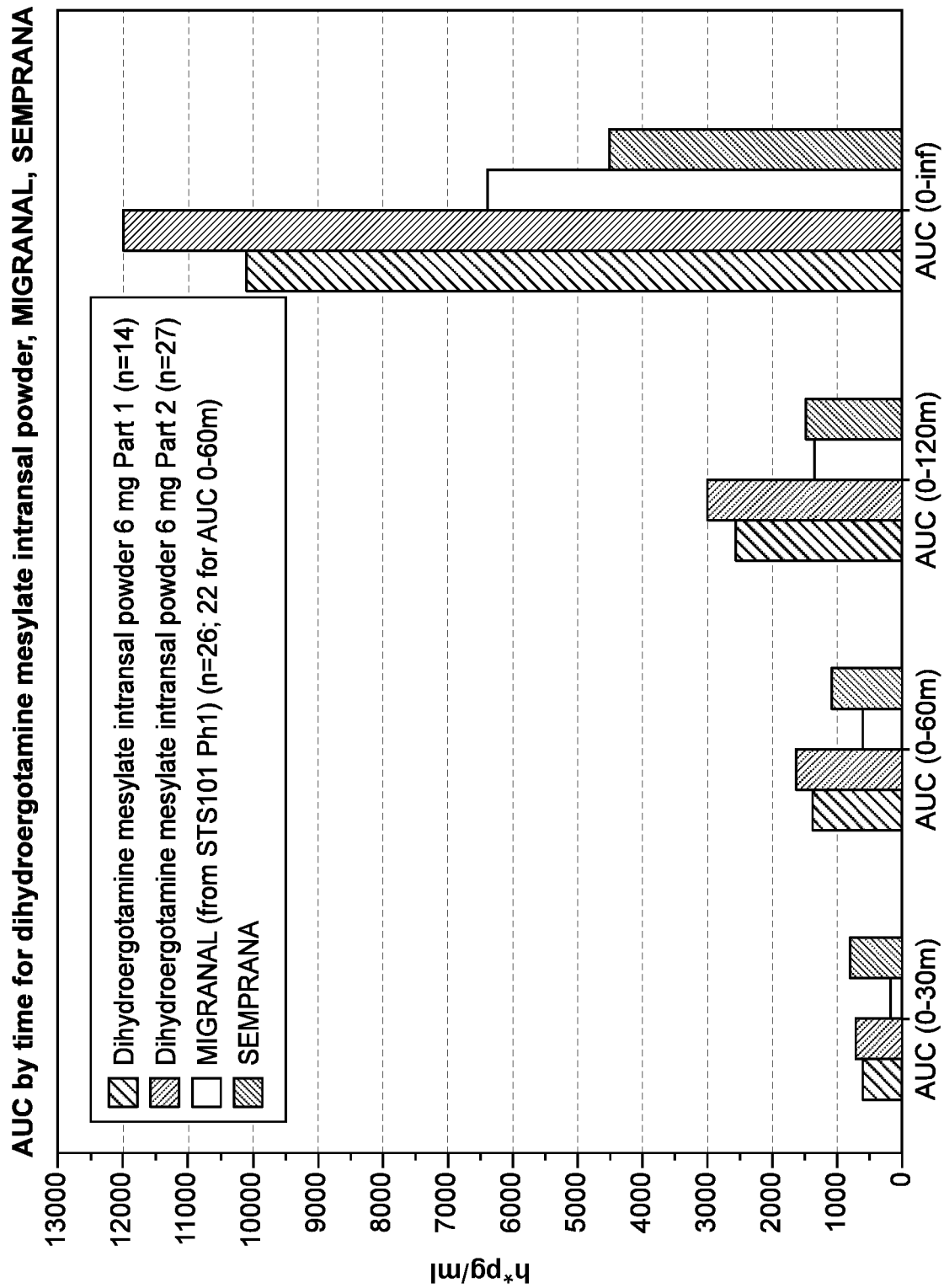
FIG. 7 shows an AUC-time profile comparison of dihydroergotamine mesylate (6 mg strength) intranasal powder, MIGRANAL (an intranasal liquid dihydroergotamine mesylate), and SEMPRANA (an oral pulmonary dihydroergotamine mesylate).

FIG. 7 shows an AUC-time profile comparison of dihydroergotamine mesylate intranasal powder, MIGRANAL (an intranasal liquid dihydroergotamine mesylate), and SEMPRANA (an oral pulmonary dihydroergotamine mesylate). Dihydroergotamine mesylate intranasal powder AUC-time profile predicts strong efficacy profile superior to MIGRANAL, and comparable to or superior to SEMPRANA. The intranasal powder and SEMPRANA are comparable in AUC values by 30-40 minutes, which can be translated as an efficacy onset within about 30 minutes as expected clinical benefit. The intranasal powder has an $AUC_{0-2h}$ that is about 2 times high as that of SEMPRANA, which can be translated as efficacy at 2 hours (time point for 1° endpoint). The intranasal powder has an $AUC_{0-inf}$ that is about 2.7 times high as that of SEMPRANA, which can be translated as sustained efficacy at beyond 2 hours to 24-48 hours.

Figure 8:
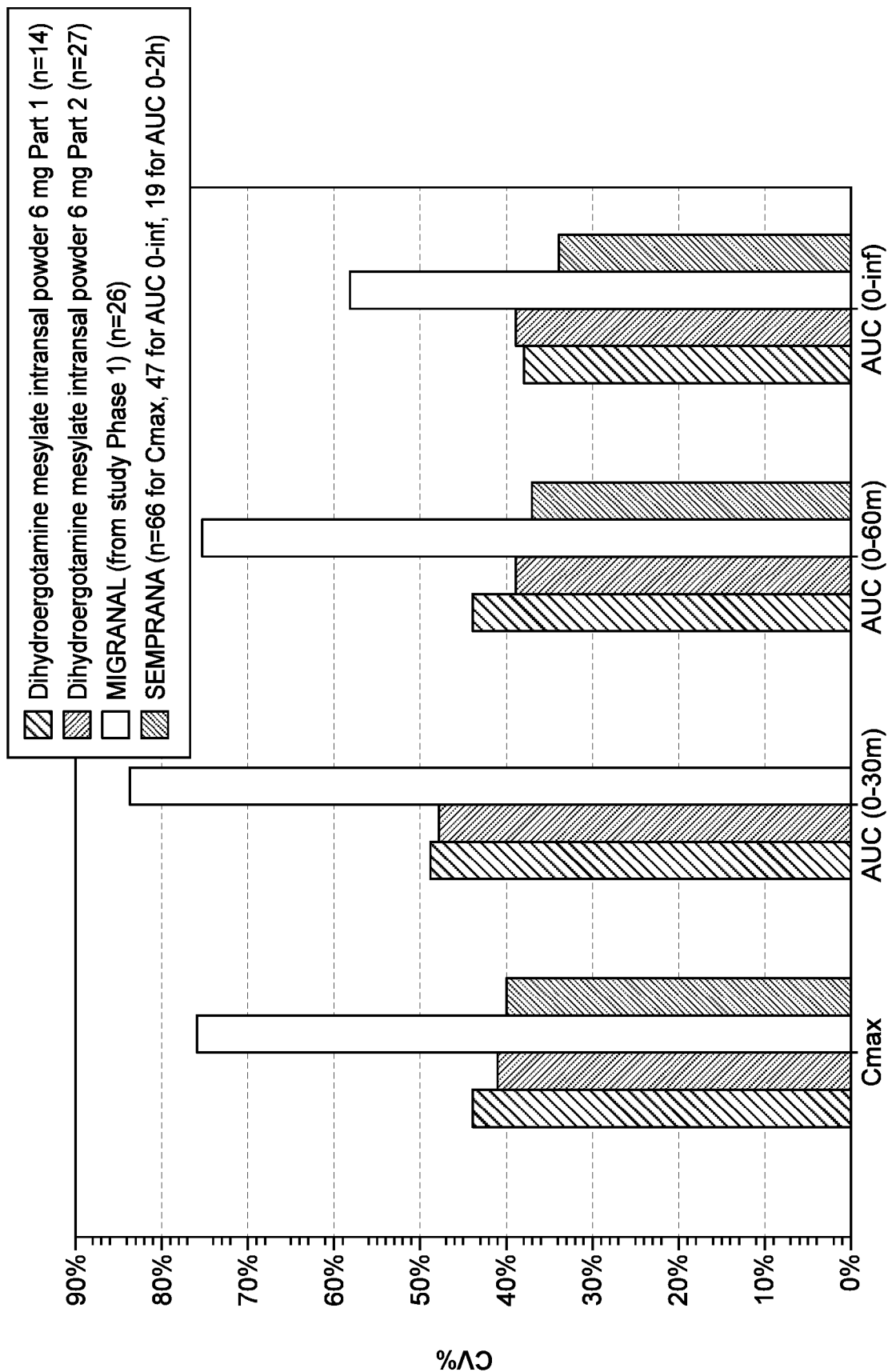
FIG. 8 shows a comparison in CV % (variability) for $C_{max}$ and AUC results of dihydroergotamine mesylate (6 mg strength) intranasal powder compared to other DHE dosage forms.

FIG. 8 shows a comparison in CV % (variability) for $C_{max}$ and AUC results of dihydroergotamine mesylate intranasal powder at 6.0 mg compared to other DHE dosage forms. Dihydroergotamine mesylate intranasal powder CV % for Cmax & AUC are superior to DHE liquid nasal spray (MIGRANAL) and comparable to oral pulmonary DHE (SEMPRANA). Such low variability predicts consistent and dependable clinical efficacy.

Table 3 shows superior unexpected pharmacokinetics of the present dihydroergotamine mesylate powder formulation compared with MIGRANAL liquid spray. For example, the powder formulation provided a 2-fold higher $AUC_{0-inf}$ and 2.8-fold higher $C_{max}$ based on geometric mean comparison with the MIGRANAL liquid spray.

TABLE 3

Comparative bioavailability evaluation comparing the present powder formulation to MIGRANAL liquid spray

| Parameter | Treatment | N | Geometric LS Means | Treatment Comparisons (Test/Reference) | Ratio of Geometric LS Means | 90% CI of the Ratio |
|---|---|---|---|---|---|---|
| $AUC_{inf}$ | E | 25 | 5402 | C/E | 2.053 | 1.688, |
| (h*pg/mL) | C | 27 | 11090 | | | 2.498 |
| $AUC_{last}$ | E | 26 | 4873 | C/E | 2.170 | 1.775, |
| (h*pg/mL) | C | 27 | 10580 | | | 2.654 |
| $C_{max}$ | E | 26 | 698.55 | C/E | 2.83 | 2.22, |
| (pg/mL) | C | 27 | 1973.70 | | | 3.59 |

Treatment:

C = 6.0 mg dihydroergotamine mesylate intranasal powder,

D = 1 mg DHE (intramuscular injection),

E = 2 mg DHE (MIGRANAL intranasal liquid spray)

LS = Least squares;

CI = Confidence Interval

A linear mixed model on the natural logarithms of AUCinf, AUClast, and Cmax was performed with sequence, period, and treatment as fixed factors, and subject within sequence as a random effect.

Table 4 shows that pharmacokinetics of the present dihydroergotamine mesylate powder formulation are comparable with vs intramuscular liquid injection. For example, Table 4 shows that $AUC_{0-inf}$ is about 83% based on geometric mean comparison.

TABLE 4

Comparative bioavailability evaluation comparing the present powder formulation to intramuscular liquid injection

| Parameter | Treatment | N | Geometric LS Means | Treatment Comparisons (Test/Reference) | Ratio of Geometric LS Means | 90% CI of the Ratio |
|---|---|---|---|---|---|---|
| $AUC_{inf}$ (h* pg/mL) | D | 26 | 13410 | C/D | 0.8273 | 0.6815, 1.004 |
|  | C | 27 | 11090 |  |  |  |
| $AUC_{last}$ (h*pg/mL) | D | 26 | 13030 | C/D | 0.8119 | 0.6638, 0.9929 |
|  | C | 27 | 10580 |  |  |  |
| $C_{max}$ (pg/mL) | D | 26 | 3253.36 | C/D | 0.61 | 0.48, 0.77 |
|  | C | 27 | 1973.70 |  |  |  |

Treatment:
C = 6.0 mg dihydroergotamine mesylate intranasal powder,
D = 1 mg DHE (intramuscular injection),
E = 2 mg DHE (Migranal intranasal liquid spray)
LS = Least squares;
CI = Confidence Interval A linear mixed model on the natural logarithms of AUCinf, AUClast, and Cmax was performed with sequence, period, and treatment as fixed factors, and subject within sequence as a random effect.

Concentration-time data for 8'-OH-DHE in Part 2 by Treatment are summarized in FIGS. 5 A to 5D. FIG. 5A displays grouped, individual subject plots of the 8'-OH-DHE concentration-time data from Part 2 by Treatment on a linear scale. FIG. 5B contains the data from Part 2 on a log-linear scale. FIGS. 5C and 5D display the 8'-OH-DHE concentration-time data from Part 2 plotted from 0-4 hours after dosing on a linear and log-linear scale, respectively. Concentrations of 8'-OH-DHE were much lower than those of parent drug. The mean maximum concentration $C_{max}$ for 8'-OH-DHE in Part 2 following 1 mg intramuscular (IM) DHE was 65.8 pg/mL-68.84 pg/mL at a mean $T_{max}$ of 1-1.14 hour after dosing. For the 2.0 mg liquid nasal spray dose, the mean $T_{max}$ was at 2-2.29 hours with a mean maximum concentration Cmax of 34.92-36.4 pg/mL for 8'-OH-DHE. For the 6.0 mg dihydroergotamine mesylate intranasal powder dose, the mean $T_{max}$ was at 2-2.02 hours with a mean maximum concentration $C_{max}$ of 110-125.98 pg/mL at that time for 8'-OH-DHE, an almost 2 times that for the IM group, and about 3 times that for the liquid spray group. In addition, there was a lag time of 0.25 to 0.5 hour in the formation of 8'-OH-DHE in most subjects. For subjects receiving 1 mg IM DHE, only 4 subjects had measurable concentrations at 48 hours after dosing. At the 2.0 mg DHE nasal spray dose level, 5 of 21 subjects had measurable concentrations at 48 hours. At the 6.0 mg dihydroergotamine mesylate intranasal powder dose level, 16 of the 21 subjects had measurable concentrations at 48 hours. The 8'-OH-DHE Cmax for the 1 mg IM DHE dose averaged 69.3 pg/mL and for the 2.0 mg DHE nasal spray dose the average decreased to 37.7 pg/mL. The $C_{max}$ for the 6.0 mg dihydroergotamine mesylate intranasal powder dose averaged 126 pg/mL which was nearly double that of the 1 mg IM DHE dose. The median Tmax was 1 and 2 hours for the 1 mg IM DHE and 2.0 mg DHE nasal spray treatments, respectively. The median Tmax was 2 hours at the 6.0 mg dihydroergotamine mesylate intranasal powder dose level.

The average terminal phase half-life for the 1 mg IM DHE dose was 16.7 hours, 22.1 hours for the 2.0 mg DHE nasal spray dose, and 19.2 hours for the 6.0 mg dihydroergotamine mesylate intranasal powder dose. The geometric mean AUCinf was 934 h*pg/mL at the 1 mg IM DHE dose, 847 h*pg/mL at the 2.0 mg DHE nasal spray dose, and 1570 h*pg/mL at the 6.0 mg dihydroergotamine mesylate intranasal powder dose.

Table 5 summarizes statistics for plasma DHE concentrations (pg/mL) by scheduled times by treatment group for the Part 2 Pharmacokinetic population. Table 6 summarizes statistics for plasma DHE pharmacokinetic parameters by the three treatment groups for the part 2 pharmacokinetic population. For example, Table 6 shows that $AUC_{0-24h}$ is about 82% of intramuscular liquid injection.

TABLE 5

Summary Statistics for Plasma DHE Concentrations (pg/mL) by Scheduled Times by Treatment Group - Part 2 Pharmacokinetic population

| Visit | Statistics | Treatment C (N = 27) | D (N = 26) | E (N = 26) |
|---|---|---|---|---|
| Predose | n | 27 | 26 | 26 |
|  | Mean | 0.000 | 0.000 | 0.000 |
|  | SD | 0.0000 | 0.0000 | 0.0000 |
|  | % CV | 0.0 | 0.0 | 0.0 |
|  | Median | 0.000 | 0.000 | 0.000 |
|  | Min, Max | 0.00, 0.00 | 0.00, 0.00 | 0.00, 0.00 |
| 0.08 Hours | n | 27 | 26 | 26 |
|  | Mean | 250.834 | 2672.398 | 12.589 |
|  | SD | 221.0782 | 977.7632 | 11.8921 |
|  | % CV | 88.1 | 36.6 | 94.5 |
|  | Median | 199.590 | 2517.900 | 12.920 |
|  | Min, Max | 18.63, 952.80 | 1127.25, 4583.03 | 0.00, 31.96 |
| 0.17 Hours | n | 27 | 26 | 26 |
|  | Mean | 1229.402 | 3008.540 | 116.520 |
|  | SD | 813.8559 | 1009.1626 | 122.5241 |
|  | % CV | 66.2 | 33.5 | 105.2 |
|  | Median | 1013.240 | 2819.180 | 69.015 |
|  | Min, Max | 221.51, 3185.04 | 1118.69, 4917.43 | 0.00, 555.41 |
| 0.25 Hours | n | 27 | 26 | 26 |
|  | Mean | 1849.121 | 3020.330 | 264.041 |
|  | SD | 917.0757 | 905.1778 | 225.2885 |
|  | % CV | 49.6 | 30.0 | 85.3 |
|  | Median | 1701.900 | 3092.240 | 211.005 |
|  | Min, Max | 412.60, 3650.65 | 1153.27, 4700.60 | 0.00, 827.98 |
| 0.5 Hours | n | 27 | 25 | 26 |
|  | Mean | 2074.486 | 3039.222 | 757.055 |
|  | SD | 872.4930 | 828.0762 | 633.2128 |
|  | % CV | 42.1 | 27.2 | 83.6 |
|  | Median | 2208.580 | 3210.160 | 600.030 |

TABLE 5-continued

Summary Statistics for Plasma DHE Concentrations (pg/mL) by Scheduled Times by Treatment Group - Part 2 Pharmacokinetic population

| Visit Predose | Statistics | Treatment C (N = 27) | D (N = 26) | E (N = 26) |
|---|---|---|---|---|
| | Min, Max | 583.90, 3590.89 | 1282.67, 4788.26 | 46.85, 1977.20 |
| 0.75 Hours | n | 27 | 26 | 26 |
| | Mean | 1810.242 | 2702.729 | 854.183 |
| | SD | 728.9172 | 596.9501 | 706.6438 |
| | % CV | 40.3 | 22.1 | 82.7 |
| | Median | 1815.730 | 2705.320 | 596.470 |

Treatment:
C = 6.0 mg dihydroergotamine mesylate intranasal powder,
D = 1 mg DHE (intramuscular injection),
E = 2 mg DHE (Migranal intranasal liquid spray)

TABLE 6

Summary Statistics for Plasma DHE Pharmacokinetic Parameters by Treatment Group - Part 2 Pharmacokinetic Population

| Parameter | Statistics | Treatment C (N = 27) | D (N = 26) | E (N = 26) |
|---|---|---|---|---|
| $AUC_{0-0.5\,h}$ (h*pg/mL) | N | 27 | 26 | 26 |
| | Mean | 686.0 | 1357 | 152.0 |
| | SD | 326.0 | 388.6 | 130.6 |
| | % CV | 47.5 | 28.6 | 85.9 |
| | Median | 661.9 | 1373 | 135.1 |
| | Min, Max | 181.7, 1305 | 539.7, 2058 | 7.710, 498.7 |
| | Geometric Mean | 602.2 | 1297 | 96.13 |
| | % CV for Geometric Mean | 59.8 | 33.1 | 150.8 |
| $AUC_{0-0.75\,h}$ (h*pg/mL) | N | 27 | 26 | 26 |
| | Mean | 1170 | 2075 | 353.5 |
| | SD | 513.5 | 550.1 | 293.5 |
| | % CV | 43.9 | 26.5 | 83.0 |
| | Median | 1178 | 2109 | 287.6 |
| | Min, Max | 321.5, 2061 | 848.8, 2986 | 40.26, 997.7 |
| | Geometric Mean | 1044 | 1996 | 234.8 |
| | % CV for Geometric Mean | 55.5 | 30.5 | 130.4 |
| $AUC_{0-1\,h}$ (h*pg/mL) | N | 27 | 26 | 26 |
| | Mean | 1603 | 2735 | 569.3 |
| | SD | 675.3 | 664.8 | 458.9 |
| | % CV | 42.1 | 24.3 | 80.6 |
| | Median | 1606 | 2784 | 454.4 |
| | Min, Max | 463.6, 2703 | 1191, 3885 | 70.92, 1576 |
| | Geometric Mean | 1443 | 2647 | 393.3 |
| | % CV for Geometric Mean | 52.8 | 27.7 | 118.5 |
| $AUC_{0-2\,h}$ (h*pg/mL) | N | 27 | 26 | 26 |
| | Mean | 2979 | 4791 | 1316 |
| | SD | 1147 | 907.5 | 989.5 |
| | % CV | 38.5 | 18.9 | 75.2 |
| | Median | 2989 | 4941 | 1078 |
| | Min, Max | 1006, 5003 | 2585, 6532 | 179.8, 3947 |
| | Geometric Mean | 2730 | 4701 | 970.9 |
| | % CV for Geometric Mean | 47.7 | 20.7 | 101.9 |
| $AUC_{0-24\,h}$ (h*pg/mL) | N | 27 | 26 | 26 |
| | Mean | 10020 | 12150 | 5139 |
| | SD | 3705 | 1833 | 2999 |
| | % CV | 37.0 | 15.1 | 58.3 |
| | Median | 10680 | 12330 | 4689 |

TABLE 6-continued

Summary Statistics for Plasma DHE Pharmacokinetic Parameters by Treatment Group - Part 2 Pharmacokinetic Population

| Parameter | Statistics | Treatment C (N = 27) | D (N = 26) | E (N = 26) |
|---|---|---|---|---|
| | Min, Max | 3630, 17640 | 8306, 14810 | 873.2, 12330 |
| | Geometric Mean | 9287 | 12010 | 4210 |
| | % CV for Geometric Mean | 43.7 | 16.2 | 79.0 |
| $AUC_{0-48\,h}$ (h*pg/mL) | N | 27 | 26 | 26 |
| | Mean | 11440 | 13240 | 5988 |
| | SD | 4357 | 2022 | 3390 |
| | % CV | 38.1 | 15.3 | 56.6 |
| | Median | 11860 | 13430 | 5583 |
| | Min, Max | 4108, 20730 | 9082, 16520 | 957.0, 13780 |
| | Geometric Mean | 10580 | 13080 | 4956 |
| | % CV for Geometric Mean | 44.2 | 16.3 | 76.6 |
| $AUC_{last}$ (h*pg/mL) | N | 27 | 26 | 26 |
| | Mean | 11440 | 13240 | 5973 |
| | SD | 4357 | 2022 | 3409 |
| | % CV | 38.1 | 15.3 | 57.1 |
| | Median | 11860 | 13430 | 5582 |
| | Min, Max | 4108, 20730 | 9082, 16520 | 873.2, 13780 |
| | Geometric Mean | 10580 | 13080 | 4908 |
| | % CV for Geometric Mean | 44.2 | 16.3 | 79.3 |
| $AUC_{inf}$ (h*pg/mL) | N | 27 | 26 | 25 |
| | Mean | 12030 | 13650 | 6498 |
| | SD | 4716 | 2143 | 3551 |
| | % CV | 39.2 | 15.7 | 54.7 |
| | Median | 12320 | 13840 | 6083 |
| | Min, Max | 4305, 22690 | 9349, 17650 | 969.0, 14390 |
| | Geometric Mean | 11090 | 13480 | 5418 |
| | % CV for Geometric Mean | 44.6 | 16.7 | 76.0 |

Treatment:
C = 6.0 mg dihydroergotamine mesylate intranasal powder,
D = 1 mg DHE (intramuscular injection),
E = 2 mg DHE (Migranal intranasal liquid spray)

4.7 Safety Analysis

A safety analyses was included for all subjects who received at least one dose of study medication. All adverse events and serious adverse events were collected starting with the time of first admission to the clinical site (Period 1; Day-1) until the end of the study, or last study visit if the subject discontinued early from the study, and were recorded on the CRFs (including the time of the occurrence of the adverse effect-AE). All adverse events reported or observed were listed, documenting course, severity, start and stop date, possible relationship to study medication, action taken, and outcome. Verbatim terms were classified to preferred terms and related system organ class using the MedDRA dictionary. The preferred terms and system organ classes were tabulated by treatment group. All reported adverse events were summarized by the number of volunteers reporting adverse events, system organ class, preferred term, severity, and relationship to study drug. Safety labs included complete blood count (CBC), chemistry and urinalysis tabulated using descriptive statistics. A tabulation of by-volunteer abnormal/out-of-range findings and changes from pre-dose to post-dose in all laboratory variables was provided. Vital signs, evaluations of nasal irritation and nasal mucosa integrity and standard 12-lead ECGs were tabulated using descriptive statistics. A tabulation of by-volunteer abnormal/out-of-range findings and changes from pre-dose to post-dose variables were provided. The study was designed to rigorously assess nasal safety and tolerability. Frequent AE collection was combined with subjective nasal irritation/symptom assessments and nasal exams at multiple timepoints.

Subjective Evaluation of Nasal Symptoms

Participants were asked to rate nasal symptoms:
1) Nasal discomfort
2) Nasal burning
3) Nasal itching
4) Nasal pain
5) Nasal blockage or obstruction
6) Abnormal or altered taste
7) Runny nose
8) Sneezing, and
9) possibly additional symptoms such as eye disorder (e.g., increased lacrimation), gastrointestinal disorder (e.g., abdominal pain), headache, vessel puncture/injection site reactions, and nervous system disorder.

Symptoms were rated by the participants on a visual analog scale (VAS) from 0-100 millimeters, with 0 being equivalent to "none", and 100 being equivalent to "worst imaginable". Each study subject answered the questions at five time points following each dosing: 5 min, 15 min, 1 hr, 4 hrs and 24 hrs. The questionnaire used is shown in FIG. 9.

Figure 10:
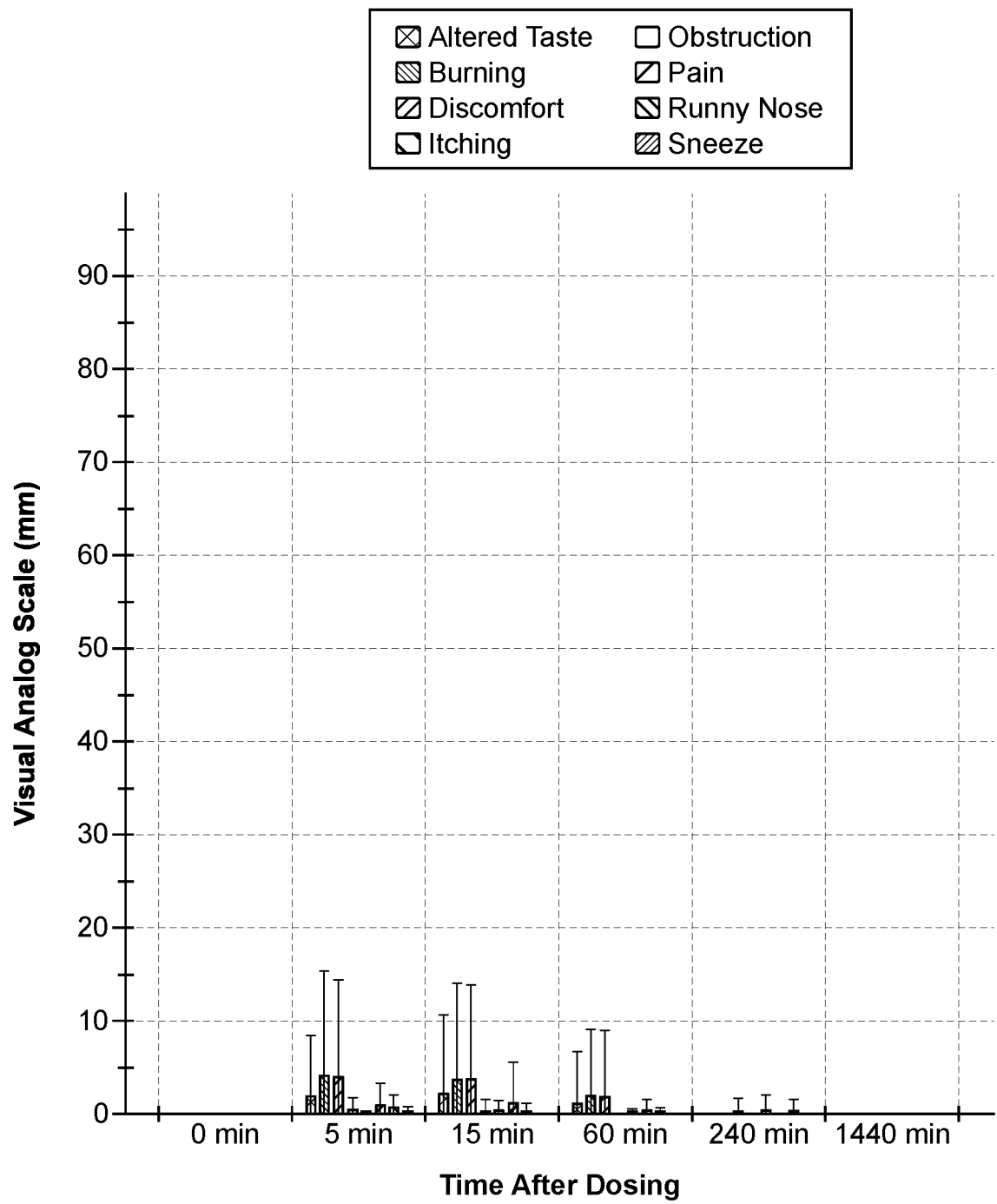
FIG. 10 shows mean VAS scores for all subjects dosed with an intranasal powder formulation comprising 6 mg dihydroergotamine mesylate (Parts 1 &2, n=41).
Figure 11:
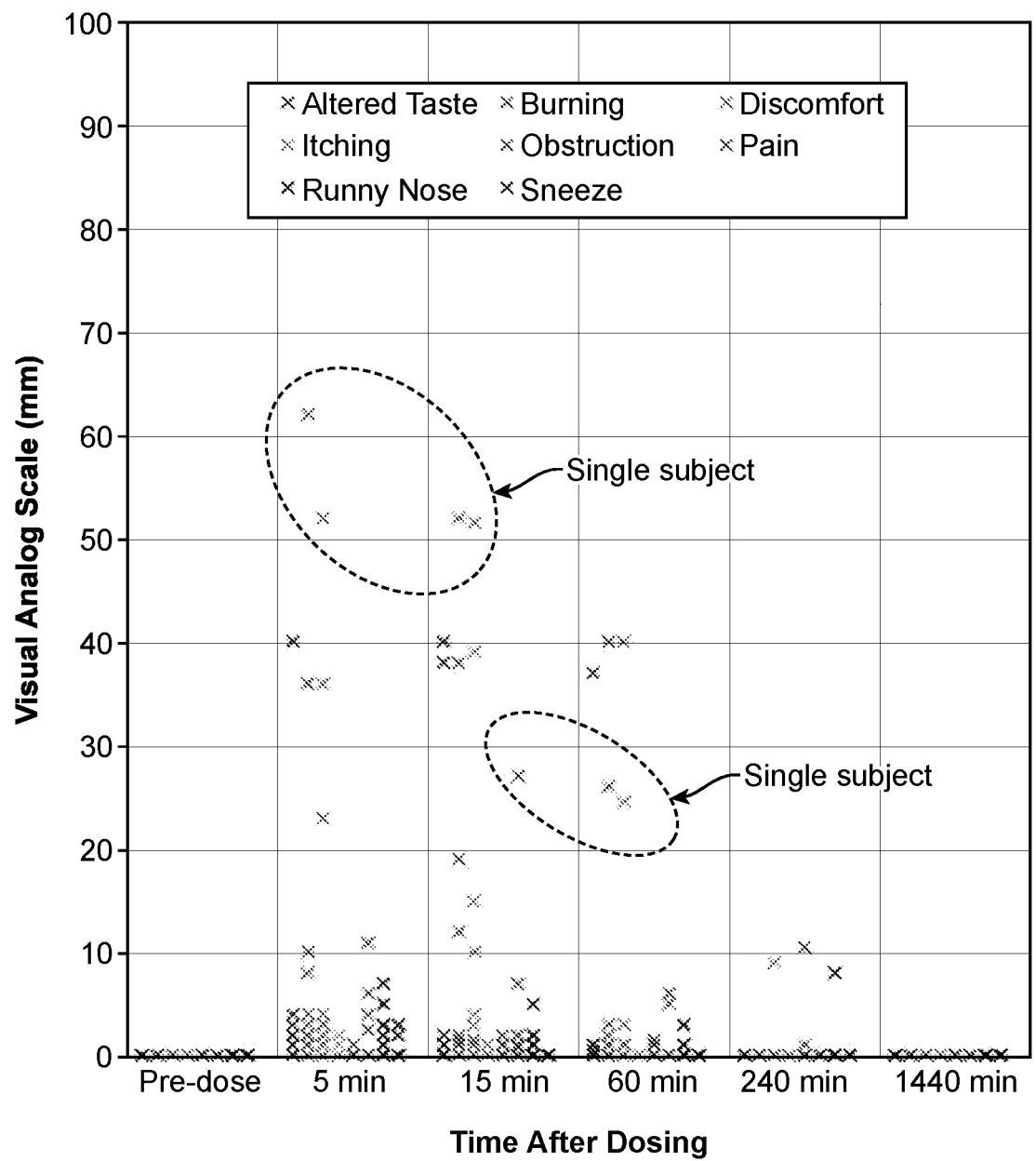
FIG. 11 shows individual VAS scores (including those for abnormal or altered taste) for all subjects reporting local or nasally related adverse effects (AEs), including dysgeusia, and dosed with an intranasal powder formulation comprising 6 mg dihydroergotamine mesylate (n=12).

The results of the safety study are shown in FIG. 10 and Table 7. 92% of scores were reported as zero, 98.4% of scores were less than 10, and 90% of all 41 subjects reported all scores as less than 20. FIG. 11 shows that subjects with local AEs tended to report higher symptom scores. 96% of all AE subject scores were less than 20. Only 4 scores were greater than 50 (in a single subject). Only one "Pain" score was more than 20 (27) at a single time point. Overall the subjective evaluation of nasal symptoms visual analog score data underscored a favorable safety and tolerability profile for the dihydroergotamine mesylate intranasal powder.

All dihydroergotamine mesylate intranasal powder adverse events were mild, transient and deemed not clinically relevant. No unexpected adverse events were reported. No nausea or "triptan-sensation" adverse events were reported. There were no clinically relevant findings made in nasal exams.

Example 5. Cluster Headache PK Escalation Study

The goals of this example are 1) to evaluate safety and pharmacokinetics (PK) of dosing a pharmaceutical composition disclosed herein into both nostrils at same time to support potential cluster headache indication, and 2) to evaluate safety and PK of dosing a pharmaceutical composition disclosed herein into both nostrils with 2 hour interval.

A certain pharmaceutical composition disclosed herein is found to be bioequivalent in both $C_{max}$ and AUC to a liquid dosage form for injection approved for cluster headache indication (e.g., D.H.E. 45).

Figure 12:
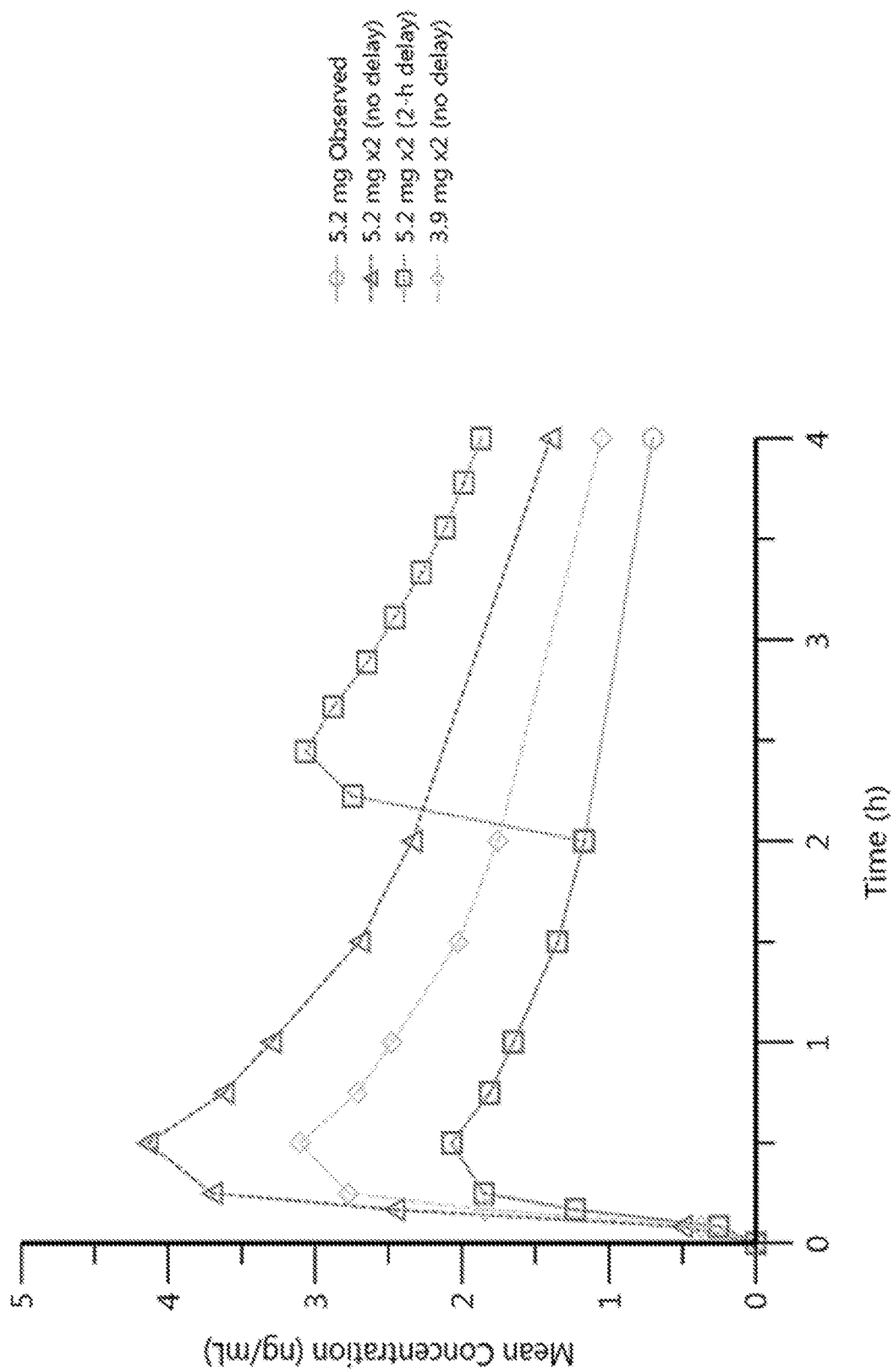
FIG. 12 shows a pharmacokinetic data model of a pharmaceutical composition disclosed herein in different strengths comprising dihydroergotamine in 3.9 mg or 5.2 mg (freebase weight) administered in a single dose, or 2 doses without delay or 2-hour delay.

FIG. 12 shows a pharmacokinetic data model of a pharmaceutical composition disclosed herein in different strengths comprising dihydroergotamine in 3.9 mg or 5.2 mg (freebase weight) administered in a single dose, or 2 doses without delay or 2-hour delay.

This clinical trial is a 4 period, cross over study, having one-week washout between treatments shown in Table 8 below. The objectives are the following:

Evaluate pharmacokinetics after administration to both nostrils at the same time Evaluate pharmacokinetics a after administration to both nostrils with 2 hour interval Compare single dose pharmacokinetics with intramuscular DHE Evaluate tolerability and safety after administration to both nostrils

TABLE 7

Drug-related adverse effects for differing doses of dihydroergotamine mesylate intranasal powder, and other DHE drug delivery methods and compositions. Incidents of adverse effects occurred in at least 2 participants in any treatment group.

| Treatment Emergent AE | Present Pharmaceutical Composition | | | Migranal Nasal spray | IM DHE |
|---|---|---|---|---|---|
| | 1.3 mg (n = 15) | 2.6 mg (n = 15) | 5.2 mg (n = 41) | (n = 27) | (n = 26) |
| Any treatment emergent AEs | 9 (60.0%) | 5 (33.3%) | 16 (39.0%) | 5 (18.5%) | 4 (15.4%) |
| Eye disorders | | | | | |
| Lacrimation increased | | | 3 (7.3%) | | |
| Gastrointestinal disorders | | | | | |
| Abdominal pain | | | 2 (4.9%) | | |
| General disorders and administration site conditions | | | | | |
| Vessel puncture/injection site reactions | 3 (20.0%) | 3 (20.0%) | | | 1 (3.8%) |
| Nervous system disorders | | | | | |
| Dysgeusia (abnormal/altered taste) | 1 (6.7%) | 1 (6.7%) | 9 (22.0%) | 2 (7.4%) | |
| Headache | 2 (13.3%) | 1 (3.8%) | | 1 (3.7%) | 1 (3.8%) |
| Respiratory, thoracic and mediastinal disorders | | | | | |
| Nasal congestion/blockage/obstruction | 2 (13.3%) | | 5 (12.2%) | | |
| Nasal discomfort | 4 (26.7%) | 3 (20.0%) | 14 (34.1%) | 2 (7.4%) | |
| Nasal pruritus (itching) | | | 3 (7.3%) | | |
| Rhinalgia (nasal pain) | | | 5 (12.2%) | 1 (3.7%) | |
| Rhinorrhea (running nose) | 1 (6.7%) | 1 (6.7%) | 6 (14.6%) | | |
| Sneezing | | | 2 (4.9%) | | |

TABLE 8

| | | The clinical design. | | |
|---|---|---|---|---|
| Number of Subjects | Period 1 Treatment | Period 2 Treatment | Period 3 Treatment | Period 4 Treatment |
| 8 | A | B | C | D |
| 8 | B | C | D | A |
| 8 | C | D | A | B |
| 8 | D | A | B | C |

Treatment A: 2 × 3.9 mg Present Pharmaceutical Composition (one in each nostril; delivered into both nostrils without delay)
Treatment B: 2 × 5.2 mg Present Pharmaceutical Composition (one in each nostril; delivered into both nostrils without delay)
Treatment C: 5.2 mg Present Pharmaceutical Composition + 5.2 mg Present Pharmaceutical Composition (one in each nostril; delivered into both nostrils with 2 hour interval)
Treatment D: 1 mg DHE intramuscular injection (D.H.E. 45)

The endpoints measured include plasma levels of DHE and metabolite (8'OH-DHE), $C_{max}$, $t_{max}$, $AUC_{0-30min}$, $AUC_{0-2}$, $AUC_{0-24}$, $AUC_{0-48}$, $AUC_{0-inf}$, and $t_{1/2}$, and adverse effects.

The examples and instances described herein are for illustrative purposes only and various modifications or changes suggested to persons skilled in the art are to be included within the spirit and purview of this application and scope of the appended claims.

What is claimed is:

1. A method of treatment or prevention of a headache, comprising administering to a human subject a powdery pharmaceutical composition that comprises an active agent, wherein said active agent is present in 4.5 mg to about 6 mg in a unit dose of said pharmaceutical composition and is selected from the group consisting of a compound having a formula of

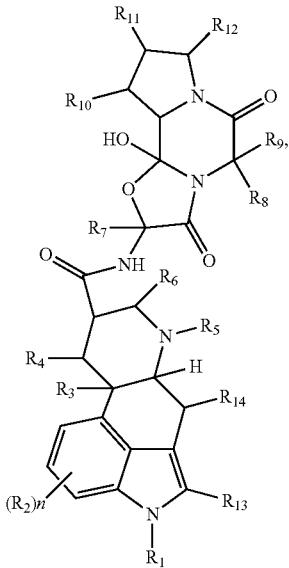

Formula (I)

a pharmaceutically acceptable salt thereof, a complex thereof, a chelate thereof, and an ion pair thereof, wherein $R_{12}$ is hydrogen or halogen in said formula, wherein said administering results in a time to reach a peak plasma concentration ($T_{max}$) of 90 minutes or longer for a metabolite of said active agent, when determined from measurement of a human plasma concentration of said metabolite by liquid chromatography-tandem mass spectrometry with automated extraction, wherein said metabolite is of Formula (I) in which $R_{12}$ is —OH, and wherein:
$R_1$ is hydrogen, ($C_1$-$C_4$) alkyl, or ($C_1$-$C_4$) perfluoroalkyl;
each $R_2$ is independently hydrogen, halogen, alkyl, acyl, heteroalkyl, —NO$_2$, —N$_3$, —OH, —OR$_{101}$, —NR$_{102}$R$_{103}$, —CONR$_{104}$R$_{105}$, or —CO$_2$R$_{106}$;
$R_3$ and $R_4$ are independently hydrogen, deuterium, halogen, hydroxy, or methoxy;
$R_5$, $R_6$, and $R_7$ are independently hydrogen, ($C_1$-$C_3$) alkyl, or ($C_1$-$C_3$) perfluoroalkyl;
$R_8$ and $R_9$ are independently hydrogen, ($C_1$-$C_4$) alkyl, or benzyl;
$R_{10}$, $R_{11}$, and $R_{14}$ are independently hydrogen, halogen, —OH, ($C_1$-$C_4$) alkyl, —CO$_2$R$_{108}$, or —CONR$_{109}$R$_{110}$;
$R_{13}$ is hydrogen or halogen;
$R_{101}$, $R_{102}$, $R_{103}$, $R_{104}$, $R_{105}$, $R_{106}$, $R_{108}$, $R_{109}$, and $R_{110}$ are independently hydrogen, halogen, alkyl, acyl, aryl, arylalkyl, heteroalkyl, heteroaryl, or heteroarylalkyl; and
n is 0, 1, 2, or 3.

2. The method of claim 1, wherein said $T_{max}$ is at least about 2 hours.

3. The method of claim 1, wherein a peak plasma concentration ($C_{max}$) of said metabolite is less than about 250 pg/ml.

4. The method of claim 1, wherein a peak plasma concentration ($C_{max}$) of said metabolite is less than about 15% of a $C_{max}$ of said active agent measured following said administration to said human subject.

5. The method of claim 1, wherein a plasma concentration of said metabolite is less than about 5% of a plasma concentration of said active agent measured within about 30 minutes following said administration to said human subject, or wherein a plasma concentration of said metabolite is less than about 2% of a plasma concentration of said active agent measured within about 15 minutes following said administration to said human subject.

6. The method of claim 1, wherein a reduced presence of said metabolite results in a reduced pharmacological effect from said metabolite in said human subject, and wherein said reduced pharmacological effect is less than 20% binding activity at an adrenergic, dopaminergic, or 5-HT receptor or receptor subtype as measured by a radioligand competitive binding assay.

7. The method of claim 1, wherein a reduced presence of said metabolite results in a reduced pharmacological effect from said metabolite in said human subject, and wherein said reduced pharmacological effect in said human subject is manifested by a reduced transcutaneous partial O$_2$ pressure as measured at the back of a foot, a reduced venous constrictive effect as determined using a venous occlusion mercury strain gauge, a less decreased diameter or compliance of a brachial artery wall, a decreased constrictive effect on a human coronary artery, meningeal artery, or saphenous vein, a less decreased venous diameter at a fixed occlusion pressure, a change in peripheral circulatory capacitance, or any combination thereof.

8. A method of treatment or prevention of a headache, comprising administering to a human subject a pharmaceutical composition that comprises an active agent, wherein said active agent is present in 4.5 mg to about 6 mg in a unit dose of said pharmaceutical composition and is selected from the group consisting of a compound having a formula of Formula (I)

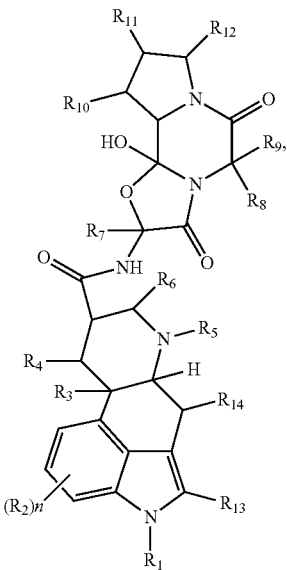

a pharmaceutically acceptable salt thereof, a complex thereof, a chelate thereof, and an ion pair thereof,
wherein said administering results in:
1) a $C_{max}$ of about 1 to about 2.5 ng/ml, or a plasma concentration of at least 1 ng/mL at about 10 minutes or shorter,
2) a $T_{max}$ of about 30 minutes or less, and
3) an AUC value selected from the group consisting of an $AUC_{0-30min}$ of about 500 to about 1000 h*pg/ml, an $AUC_{0-60min}$ of about 1000 to about 2000 h*pg/ml, an $AUC_{0-120min}$ of about 2000 to about 3000 h*pg/ml, and an $AUC_{0-inf}$ of about 10000 to about 12000 h*pg/ml,
when determined from measurement of a human plasma concentration of said active agent by liquid chromatography-tandem mass spectrometry with automated extraction, and
wherein:
$R_1$ is hydrogen, $(C_1-C_4)$ alkyl, or $(C_1-C_4)$ perfluoroalkyl;
each $R_2$ is independently hydrogen, halogen, alkyl, acyl, heteroalkyl, $-NO_2$, $-N_3$, $-OH$, $-OR_{101}$, $-NR_{102}R_{103}$, $-CONR_{104}R_{105}$, or $-CO_2R_{106}$;
$R_3$ and $R_4$ are independently hydrogen, deuterium, halogen, hydroxy, or methoxy;
$R_5$, $R_6$, and $R_7$ are independently hydrogen, $(C_1-C_3)$ alkyl, or $(C_1-C_3)$ perfluoroalkyl;
$R_8$ and $R_9$ are independently hydrogen, $(C_1-C_4)$ alkyl, or benzyl;
$R_{10}$, $R_{11}$, $R_{12}$, and $R_{14}$ are independently hydrogen, halogen, $-OH$, $(C_1-C_4)$ alkyl, $-CO_2R_{108}$, or $-CONR_{109}R_{110}$;
$R_{13}$ is hydrogen or halogen;
$R_{101}$, $R_{102}$, $R_{103}$, $R_{104}$, $R_{105}$, $R_{106}$, $R_{108}$, $R_{109}$, and $R_{110}$ are independently hydrogen, halogen, alkyl, acyl, aryl, arylalkyl, heteroalkyl, heteroaryl, or heteroarylalkyl; and
n is 0, 1, 2, or 3.

9. The method of claim 8, further providing a half-life of said active agent from about 12 hours to about 13 hours.

10. The method of claim 8, wherein said administering results in a time to reach a peak plasma concentration ($T_{max}$) of 90 minutes or longer for a metabolite of said active agent, when determined from measurement of a human plasma concentration of said metabolite by liquid chromatography-tandem mass spectrometry with automated extraction, wherein $R_{12}$ is hydrogen or halogen in said formula of said active agent, and wherein said metabolite is of Formula (I) in which $R_{12}$ is $-OH$.

11. A method of treatment or prevention of a headache, comprising administering to a human subject a pharmaceutical composition that comprises an active agent, wherein said active agent is present in 4.5 mg to about 6 mg in a unit dose of said pharmaceutical composition and is selected from the group consisting of a compound having a formula of Formula (I)

a pharmaceutically acceptable salt thereof, a complex thereof, a chelate thereof, and an ion pair thereof,
wherein said administering results in an apparent clearance (CL/F) value of said active agent from about 100 L/hr to about 1000 L/hr, and
wherein:
$R_1$ is hydrogen, $(C_1-C_4)$ alkyl, or $(C_1-C_4)$ perfluoroalkyl;
each $R_2$ is independently hydrogen, halogen, alkyl, acyl, heteroalkyl, $-NO_2$, $-N_3$, $-OH$, $-OR_{101}$, $-NR_{102}R_{103}$, $-CONR_{104}R_{105}$, or $-CO_2R_{106}$;
$R_3$ and $R_4$ are independently hydrogen, deuterium, halogen, hydroxy, or methoxy;
$R_5$, $R_6$, and $R_7$ are independently hydrogen, $(C_1-C_3)$ alkyl, or $(C_1-C_3)$ perfluoroalkyl;
$R_8$ and $R_9$ are independently hydrogen, $(C_1-C_4)$ alkyl, or benzyl;
$R_{10}$, $R_{11}$, $R_{12}$, and $R_{14}$ are independently hydrogen, halogen, $-OH$, $(C_1-C_4)$ alkyl, $-CO_2R_{108}$, or $-CONR_{109}R_{110}$;
$R_{13}$ is hydrogen or halogen;
$R_{101}$, $R_{102}$, $R_{103}$, $R_{104}$, $R_{105}$, $R_{106}$, $R_{108}$, $R_{109}$, and $R_{110}$ are independently hydrogen, halogen, alkyl, acyl, aryl, arylalkyl, heteroalkyl, heteroaryl, or heteroarylalkyl; and
n is 0, 1, 2, or 3.

12. The method of claim 1, wherein said $R_3$ and said $R_4$ are both hydrogen.

13. The method of claim 12, wherein said active agent comprises dihydroergotamine or a pharmaceutically acceptable salt thereof.

14. The method of claim 1, wherein said metabolite is 8'-hydroxy dihydroergotamine.

15. The method of claim 1, wherein said pharmaceutical composition further comprises about 6 mg to about 7 mg of a sugar alcohol.

16. The method of claim 1, wherein said active agent is in an amorphous form.

17. The method of claim 1, wherein said headache is a migraine.

18. The method of claim 1, wherein said headache comprises a migraine headache with aura, a migraine headache without aura, cluster headache, post-traumatic headache, hemiplegic migraine, basilar migraine, episodic migraine, chronic migraine, refractory migraine, migraine attack when treatment is initiated at least 1-24 hours after an onset of attack, migraine attack when treatment is initiated at the earliest premonitory sign or symptom, pediatric migraine, status migraine, chronic daily headache, a migraine attack with allodynia, menstrually-associated migraine, menstrual migraine, migraine-upon-awakening, rapid-onset migraine, or any combination thereof.

19. The method of claim 1, wherein said administration comprises delivering two or more doses of said pharmaceutical composition in two or more devices to said human subject.

20. The method of claim 19, wherein a first dose and a second dose of said two or more doses are separated by about 2 hours or longer.

21. The method of claim 1, wherein said pharmaceutical composition further comprises a carrier that is at least partially adhesive to mucus.

22. The method of claim 1, wherein said pharmaceutical composition further comprises a carrier, and wherein the carrier is at least partially adhesive to mucus and present in an amount at least partially effective to result in said Tmax.

23. The method of claim 1, wherein said pharmaceutical composition further comprises a carrier, and wherein the carrier is at least partially adhesive to mucus and present in at least 12 mg in a unit dose of said pharmaceutical composition.

24. The method of claim 1, wherein said administering comprises delivering said pharmaceutical composition in a delivery device that comprises a poppet valve and a retainer that holds the poppet valve.

25. The method of claim 1, wherein said active agent comprises a pharmaceutically acceptable salt of dihydroergotamine.

26. The method of claim 1, wherein said active agent comprises dihydroergotamine mesylate.

27. The method of claim 26, wherein at least one of the following applies:
    said $T_{max}$ is at least about 2 hours;
    a peak plasma concentration ($C_{max}$) of said metabolite is less than about 250 pg/ml;
    a peak plasma concentration ($C_{max}$) of said metabolite is less than about 15% of a $C_{max}$ of said active agent measured following said administration to said human subject;
    a plasma concentration of said metabolite is less than about 5% of a plasma concentration of said active agent measured within about 30 minutes following said administration to said human subject, or wherein a plasma concentration of said metabolite is less than about 2% of a plasma concentration of said active agent measured within about 15 minutes following said administration to said human subject;
    a reduced presence of said metabolite results in a reduced pharmacological effect from said metabolite in said human subject, and wherein said reduced pharmacological effect is less than 20% binding activity at an adrenergic, dopaminergic, or 5-HT receptor or receptor subtype as measured by a radioligand competitive binding assay; or
    a reduced presence of said metabolite results in a reduced pharmacological effect from said metabolite in said human subject, and wherein said reduced pharmacological effect in said human subject is manifested by a reduced transcutaneous partial $O_2$ pressure as measured at the back of a foot, a reduced venous constrictive effect as determined using a venous occlusion mercury strain gauge, a less decreased diameter or compliance of a brachial artery wall, a decreased constrictive effect on a human coronary artery, meningeal artery, or saphenous vein, a less decreased venous diameter at a fixed occlusion pressure, a change in peripheral circulatory capacitance, or any combination thereof.

28. The method of claim 8, wherein said active agent comprises dihydroergotamine mesylate.

29. The method of claim 28, further providing a half-life of said active agent from about 12 hours to about 13 hours, or wherein said administering results in a time to reach a peak plasma concentration ($T_{max}$) of 90 minutes or longer for a metabolite of said active agent, when determined from measurement of a human plasma concentration of said metabolite by liquid chromatography-tandem mass spectrometry with automated extraction, wherein $R_{12}$ is hydrogen or halogen in said formula of said active agent, and wherein said metabolite is of Formula (I) in which $R_{12}$ is —OH.

30. The method of claim 11, wherein said active agent comprises dihydroergotamine mesylate.

31. The method of claim 1, wherein said active agent is dihydroergotamine mesylate, and wherein said metabolite comprise 8'-hydroxy dihydroergotamine.

32. The method of claim 1, wherein said $T_{max}$ is a mean value from a human clinical study.

33. The method of claim 2, wherein said $T_{max}$ is a mean value from a human clinical study.

34. The method of claim 8, wherein said $C_{max}$, $T_{max}$ and AUC value are mean values from a human clinical study.

35. The method of claim 11, wherein said CL/F value is a mean value from a human clinical study.

* * * * *